US009533973B2

(12) United States Patent
Zhou et al.

(10) Patent No.: US 9,533,973 B2
(45) Date of Patent: Jan. 3, 2017

(54) ALLOSTERIC MODULATORS OF 5-HYDROXYTRYPTAMINE 2C RECEPTOR (5-HT2CR)

(71) Applicant: THE BOARD OF REGENTS OF THE UNIVERSITY OF TEXAS SYSTEM, Austin, TX (US)

(72) Inventors: Jia Zhou, League City, TX (US); Chunyong Ding, Galveston, TX (US); Kathryn A. Cunningham, Galveston, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 14/363,141

(22) PCT Filed: Dec. 7, 2012

(86) PCT No.: PCT/US2012/068360
§ 371 (c)(1),
(2) Date: Jun. 5, 2014

(87) PCT Pub. No.: WO2013/086266
PCT Pub. Date: Jun. 13, 2013

(65) Prior Publication Data
US 2014/0336375 A1 Nov. 13, 2014

Related U.S. Application Data

(60) Provisional application No. 61/568,526, filed on Dec. 8, 2011.

(51) Int. Cl.
| | | |
|---|---|---|
| *C07D 211/32* | (2006.01) | |
| *C07D 405/12* | (2006.01) | |
| *C07D 223/16* | (2006.01) | |
| *C07D 241/04* | (2006.01) | |
| *C07D 211/34* | (2006.01) | |
| *C07D 211/60* | (2006.01) | |
| *C07H 15/14* | (2006.01) | |
| *C07H 15/16* | (2006.01) | |
| *C07D 309/10* | (2006.01) | |

(52) U.S. Cl.
CPC .......... *C07D 405/12* (2013.01); *C07D 211/32* (2013.01); *C07D 211/34* (2013.01); *C07D 211/60* (2013.01); *C07D 223/16* (2013.01); *C07D 241/04* (2013.01); *C07D 309/10* (2013.01); *C07H 15/14* (2013.01); *C07H 15/16* (2013.01)

(58) Field of Classification Search
CPC ... C07D 405/12; C07D 241/04; C07D 223/16; C07D 211/32; C07D 309/10
USPC ......... 540/594; 544/130, 374, 390; 546/207, 546/245
See application file for complete search history.

(56) References Cited

U.S. PATENT DOCUMENTS

| | | | | |
|---|---|---|---|---|
| 4,278,789 A | * | 7/1981 | Birkenmeyer | C07H 15/16 536/16.3 |
| 5,106,982 A | * | 4/1992 | Ita et al. | 546/208 |
| 6,333,339 B1 | | 12/2001 | Boettcher et al. | 514/323 |
| 7,164,011 B2 | * | 1/2007 | Lewis | C07H 17/00 536/16.2 |
| 7,199,106 B2 | * | 4/2007 | Lewis | C07D 405/12 514/24 |
| 7,256,177 B2 | * | 8/2007 | Lewis | C07H 13/10 514/24 |
| 7,871,982 B2 | * | 1/2011 | Umemura | C07H 15/16 514/24 |
| 2004/0230046 A1 | | 11/2004 | Lewis et al. | 536/18.7 |
| 2009/0042943 A1 | | 2/2009 | Gobbi et al. | 514/330 |

FOREIGN PATENT DOCUMENTS

| | | |
|---|---|---|
| EP | 0682015 | 4/1995 |
| EP | 1958631 | 8/2008 |
| EP | 1970377 | 9/2008 |
| EP | 2166015 | 3/2010 |
| WO | WO/2004/016632 | 2/2004 |

OTHER PUBLICATIONS

Birkenmeyer et al J. Med. Chem. 1984, 27, 216-223.*
Melis et al Journal of Physical Chemistry B 2009, 113, 12148-12153—abstract.*
Hada et al Reaction Kinetics and Catalysis Letters 2001, 73, 109-115—abstract.*
Allosteric Regulation, Wikipedia p. 1-6 (2015).*
Bin et al. "Positive allosteric . . . " Molecular Pharm. 64:78084 (2003).*
Conn et al. "Allosteric modulators . . . " Nature review 8:41-54 (2009).*
Ding et al. "Exploration of synthetic . . . " ACS chemical neurosci. 3:538-545 (2012).*
Lassalle et al. "2-phenylsulfonyl . . . " CA130:196652 (1999).*
Lazareo "Determination of allosteric . . . " Recptor signal transduction protocols (2004) p. 29-47.*
Lewis et al. "Preparation of lincomycin . . . " CA145:124813 (2006).*
Umemura et al. "Preparation of lincomycin . . . " CA147:72978 (2007).*
Birkenmeyer "Analog of lincomycin . . . " CA95:98236 (1981).*
International Search Report and Written Opinion in International Application No. PCT/US2012/068360 dated May 31, 2013.
Im, et al., "Positive Allosteric Modulator of the Human 5-HT2C Receptor" Mol Pharmacol. 64:78-84, 2003.
Extended European Search Report in European Application No. 12855886.3 dated May 19, 2015.
Birkenmeyer, et al., "Synthesis and antimicrobial activity of clindamycin analogues: pirlimycin, a potent antibacterial agent" J Med Chem. 27(2): 216-223, 1984.
* cited by examiner

*Primary Examiner* — Celia Chang
(74) *Attorney, Agent, or Firm* — Norton Rose Fulbright US LLP

(57) ABSTRACT

The disclosure is directed to compounds identified as allosteric modulators of 5-HT 2CR, as well as pharmaceutical compositions and methods using the same. Certain embodiments also include methods of identifying and methods of synthesizing the compounds. Optimization and development of allosteric 5-HT 2CR modulators that bind sites other than the primary ligand binding site generate novel, highly selective, and potent ligands of 5-HT2CR. Such molecules can be used as small molecule probes for the nervous system and as effective therapeutics for a variety of diseases.

4 Claims, 14 Drawing Sheets

ALLOSTERIC MODULATORS OF 5-HYDROXYTRYPTAMINE 2C RECEPTOR (5-HT2CR)

This application is a National Stage Application of and claims priority to PCT/US2012/068360 filed Dec. 7, 2012, which claims priority to U.S. Provisional Patent Application No. 61/568,526 filed Dec. 8, 2011. This application claims priority to the above reference applications and incorporates each referenced application herein by reference in their entirety.

STATEMENT REGARDING FEDERALLY FUNDED RESEARCH

This invention was made with government support under grants P30 (DA028821) and R21 (MH093844) awarded by National Institutes of Health (NIH). The government has certain rights in the invention.

FIELD

Embodiments are directed to psychiatry, neurology, and medicinal chemistry.

BACKGROUND

The 5-hydroxytryptamine 2C receptor (5-$HT_{2C}R$) is involved in a diversity of physiological functions, such as nociception, motor behavior, endocrine secretion, thermoregulation, appetite modulation, and the control of exchanges between the central nervous system and the cerebrospinal fluid (Iwamoto et al., *RNA Biol.*, 6, 248-53, 2009; Bubar et al., *Prog. Brain Res.* 172, 319-346, 2008; Berg et al., *Neuropharmacology* 55, 969-76, 2008; Di Giovanni, *Curr. Top. Med. Chem.* 6, 1909-25, 2006; Di Giovanni, *Curr. Med. Chem.* 13, 3069-81, 2006; Fone et al., *Br. J. Pharmacol.* 123, 8, 1998). This receptor has also been implicated in numerous pathologies, and the modulation of 5-$HT_{2C}R$ function holds a tremendous amount of therapeutic promise for the treatment of diseases such as addiction, anxiety, depression, obesity/eating disorders, Parkinson's disease, and schizophrenia (Leggio et al., *Neuropharmacology* 56, 507-13, 2009; Nic Dhonnchadha et al., *Behav. Brain Res.* 195, 39-53, 2008; Bubar et al., *Prog. Brain Res.* 172, 319-346, 2008; Maillet, et al., *Prog. Brain Res.* 172, 407-20, 2008; McCreary et al., *Neuropsychopharmacology* 20, 6, 1999; Miller, *Mol. Interv.* 5, 5, 2005; Di Giovanni, *Curr. Top. Med. Chem.* 6, 1909-25, 2006; Di Giovanni, *Curr. Med. Chem.* 13, 3069-81, 2006). Successful development of 5-$HT_{2C}R$ ligands requires selectivity over the highly homologous 5-$HT_{2A}R$ and 5-$HT_{2B}R$ because activity at these receptors can result in significant adverse CNS and cardiovascular events.

Traditional screening for ligands has been optimized to detect standard orthosteric agonists and antagonists. Conversely, with increasing emphasis on cellular functional screens, more allosteric ligands are being discovered as potential medications. Allosteric modulators of the 5-$HT_{2C}R$ present a novel drug design strategy to augment the response to endogenous 5-HT in a site- and event-specific manner (Conn et al., *Nature Reviews Drug Discovery* 8, 41-54, 2009). In addition, there are theoretical reasons that allosteric ligands may be preferred therapeutic chemical targets including the prospects for increased selectivity, better control of physiological systems, as well as separate control of affinity and efficacy (Kenakin, *J. Biomol. Screen.* 15 (2), 119-130, 2010). To date, PNU-69176E, identified via a chemical library screen, is the only synthetic compound that has been reported as a selective allosteric modulator of 5-$HT_{2C}R$ (Im et al., *Mol. Pharmacol.* 64, 78-84, 2003; Ding et al., *ACS Chem. Neurosci.* 3, 538-545, 2012); however, the relevant structure-activity relationship (SAR) studies are sparse, and thus knowledge in this regard is quite limited.

Thus, there remains a need for additional specific allosteric modulators of 5-$HT_{2C}R$.

SUMMARY

Embodiments of the invention are directed to compounds identified as allosteric modulators of 5-$HT_{2C}R$, as well as pharmaceutical compositions and methods using the same. Certain embodiments also include methods of identifying and methods of synthesizing the compounds. Optimization and development of allosteric 5-$HT_{2C}R$ modulators that bind sites other than the primary ligand binding site generate novel, highly selective, and potent ligands of 5-$HT_{2C}R$. Such molecules can be used as small molecule probes for the nervous system and as effective therapeutics for a variety of diseases. The inventors have designed and/or synthesized a series of piperidine-, piperazine-, and benzazepine-based small molecule 5-$HT_{2C}R$ allosteric modulators. The inventors have demonstrated the functional activity of compounds described herein providing in vivo evidence of 5-$HT_{2C}R$ allosteric modulation (Ding et al., *ACS Chem. Neurosci.* 3, 538-545, 2012).

Certain embodiments are directed to the compounds having the general formula of Formula I.

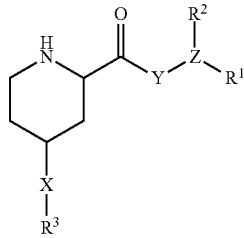

Formula I

In certain aspects, Y is —NH—, piperidine, pyrrolidine, or piperazine.

In a further aspect Z is a linear or branched, saturated or unsaturated, $C_1$, $C_2$, $C_3$, $C_4$, $C_5$, $C_6$, $C_7$, $C_8$, $C_9$, or $C_{10}$ alkyl or heteroalkyl; or a carbonyl. In one embodiment, Z is —CH—. When Z comprises more than one carbon, $R^1$ and $R^2$ can be, but need not be attached to the same carbon atom. In some embodiments, Z is a linear or branched, saturated or unsaturated, $C_1$, $C_2$, $C_3$, or $C_4$ alkyl.

Alternatively, in certain aspects, Y and Z together form a guanidino group, where $R^1$ and $R^2$ are attached to the terminal nitrogen, i.e., —N=C($NH_2$)—$NR^1R^2$.

In certain aspects, $R^1$ and $R^2$ are independently selected from: hydrogen, halogen, nitro, cyano, hydroxy, amino, mercapto, formyl, carboxy, oxo, carbamoyl, substituted or unsubstituted alkyl, substituted or unsubstituted heteroalkyl, alkoxy, alkylthio, alkylamino, (alkyl)$_2$-amino, alkylsulfinyl, alkylsulfonyl, arylsulfonyl, substituted or unsubstituted cycloalkyl, substituted or unsubstituted heterocyclyl, substituted or unsubstituted aryl, substituted or unsubstituted phenyl, and substituted or unsubstituted heteroaryl.

In some embodiments, $R^2$ is hydrogen, hydroxy, halo, oxo, substituted or unsubstituted alkyl, or amino. In one embodiment, $R^2$ is hydrogen or hydroxy. In certain embodiments $R^2$ is hydrogen.

In some embodiments, $R^1$ is hydrogen, hydroxy, halogen, substituted or unsubstituted alkyl, substituted or unsubstituted heteroalkyl, alkoxy, alkylthio, amino, alkylamino, $(alkyl)_2$-amino, alkylsulfinyl, alkylsulfonyl, arylsulfonyl, substituted or unsubstituted cycloalkyl, substituted or unsubstituted heterocyclyl, substituted or unsubstituted aryl, or substituted or unsubstituted heteroaryl. In some embodiments, $R^1$ is hydroxyl, substituted or unsubstituted heterocyclyl, substituted or unsubstituted aryl, or substituted or unsubstituted heteroaryl. In some embodiments, $R^1$ is a substituted or unsubstituted phenyl or a substituted or unsubstituted 5- or 6-membered heterocycle containing 1 or 2 heteroatoms selected from nitrogen and oxygen.

In certain aspects, X is a direct bond, or a linear or branched, saturated or unsaturated, $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, or $C_{15}$ alkyl.

In certain aspects, $R^3$ is hydrogen, or an optionally substituted: alkyl, heteroalkyl, cycloalkyl, heterocyclyl, aryl, or heteroaryl. In certain aspects, $R^3$ can be optionally substituted as described below.

In some embodiments, X is a linear, saturated or unsaturated $C_{7-12}$ alkyl, and $R^3$ is H. In some embodiments, X is a linear, saturated $C_{10-15}$, preferably $C_{11}$, alkyl, and $R^3$ is H (as in Formula II below). In other embodiments, X is a direct bond or a linear, saturated or unsaturated $C_{1-4}$ alkyl, and $R^3$ is a substituted or unsubstituted cycloalkyl, substituted or unsubstituted heterocyclyl, substituted or unsubstituted aryl, or substituted or unsubstituted heteroaryl. In another embodiment, X is a linear, saturated $C_{1-4}$ alkyl, and $R^3$ is a substituted or unsubstituted aryl, or a substituted or unsubstituted cycloalkyl.

The substituents are selected such that the compound is not PNU-69176E or its isomer. PNU-69176E or its isomer can be specifically excluded from the claimed invention. But in some embodiments, one or more substituents, but not all of the substituents, are selected to mimic the polar functionality (Y, Z, $R^1$, $R^2$) and/or membrane anchoring (X, $R^3$) of PNU-69176E.

Certain aspects are directed to compounds having the general formula of Formula II.

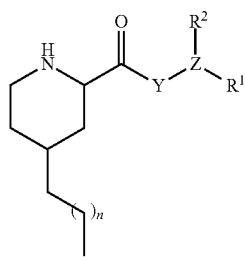

Formula II

In certain aspects, Y, Z, $R^1$, and $R^2$ are as described above with respect to Formula I. In certain aspects, n is 2, 3, 4, 5, 6, 7, 8, 9, 10, 11, 12, 13, 14, or 15. In a particular aspect, n is 9. In certain aspects of Formula II, Y is —NH— or piperazine. In certain aspects of Formula II, Z is $C_{1-4}$ alkyl, heteroalkyl, or carbonyl. In certain aspects of Formula II, when Y is —NH—, Z is $C_{1-4}$ alkyl. In others, when Y is piperazine, Z is carbonyl.

In certain aspects of Formula II, $R^1$ is hydroxy; $C_{1-4}$hydroxyalkyl; $C_{1-4}$alkoxy; aminosulfite; unsubstituted monosaccharide; substituted monosaccharide, wherein the saccharide is substituted with S, Cl, or thioalkyl at position 1, 2, 3, or 4; phenyl; benzyl; substituted benzyl or phenyl, wherein the benzyl or phenyl is substituted individually and independently with 1, 2, 3, 4, or 5 hydroxy, linear or branched $C_{1-4}$alkyl, or $C_{1-2}$alkoxy; $C_{5-6}$heterocyclic; substituted $C_{5-6}$heterocyclic, wherein the ring comprises 1 or 2 nitrogens, 1 or 2 oxygens, or a nitrogen and oxygen, and the ring is optionally substituted with hydroxyl, oxo, $C_{1-4}$alkyl, $C_{1-4}$alkoxy, carboxymethyl, or methylsulfonyl; or secondary or tertiary methyl or ethyl amine. In certain aspects of Formula II, $R^1$ is a substituted or unsubstituted alkyl, substituted or unsubstituted aryl, or substituted or unsubstituted heterocyclyl group.

In certain aspects of Formula II, $R^2$ is hydrogen; hydroxy; linear or branched $C_{1-4}$alkyl; linear or branched $C_{1-4}$alkoxy; phenyl substituted $C_{1-4}$alkyl; oxo; phenyl; substituted phenyl wherein the phenyl is substituted with one or more of halide, hydroxy, $C_{1-4}$hydroxyalkyl, $C_{1-4}$alkylsulfonyl, $C_{1-4}$alkylthio, $C_{1-4}$alkyl, or $C_{1-4}$alkoxy; benzyl; or substituted benzyl wherein the phenyl is substituted with halide, hydroxy, $C_{1-4}$alkyl, or $C_{1-4}$alkoxy.

In certain aspects of Formula II, Z is —CH—, R1 is hydroxymethyl, and R2 is hydroxymethyl phenyl.

Certain aspects are directed to compounds having a general formula of Formula III.

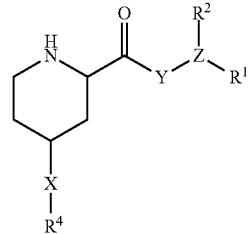

Formula III

In certain aspects, X, Y, Z, $R^1$, and $R^2$ are as defined above with respect to Formula I. For some embodiments of Formula III, Y is —NH—, and Z is —CH—. For some embodiments of Formula III, $R^2$ is ethyl substituted with halogen or hydroxy, and $R^1$ is hydroxy; $C_{1-4}$alkoxy; aminosulfite; unsubstituted monosaccharide; substituted monosaccharide, wherein the saccharide is substituted with S, Cl, or thioalkyl at position 1, 2, 3, or 4; phenyl; benzyl; substituted benzyl or phenyl, wherein the benzyl or phenyl is substituted individually and independently with 1, 2, 3, 4, or 5 hydroxy, linear or branched $C_{1-4}$alkyl, or $C_{1-2}$alkoxy; $C_{5-6}$heterocylic; substituted $C_{5-6}$heterocyclic, wherein the ring comprises 1 or 2 nitrogens, 1 or 2 oxygens, or a nitrogen and oxygen, and the ring is optionally substituted with hydroxyl, oxo, $C_{1-4}$alkyl, $C_{1-4}$alkoxy, carboxymethyl, or methylsulfonyl; or secondary or tertiary methyl or ethyl amine. For some embodiments of Formula III, X is a direct bond or a linear, saturated or unsaturated $C_{1-4}$ alkyl (e.g., —$CH_2$—$CH_2$—). In some embodiments of Formula III, X is a direct bond.

In certain aspects, $R^4$ is substituted or unsubstituted cycloalkyl, substituted or unsubstituted heterocyclyl, substituted or unsubstituted aryl, or substituted or unsubstituted heteroaryl. In certain aspects, $R^4$ is substituted or unsubstituted phenyl, or substituted or unsubstituted cyclohexane. In some embodiments, $R^4$ is phenyl substituted with one or more of: halogen, $CF_3$, $C_{1-4}$ alkoxy, methoxy, $C_{1-8}$ alkyl, methyl, amino, and phenyl.

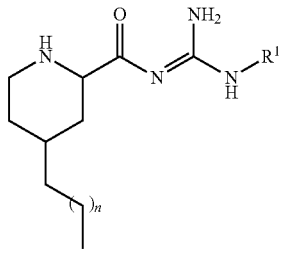

Formula IIa

In Formula IIa Y and Z together form a guanidino group, and $R^2$ is hydrogen. In certain embodiments of the guanidine compounds, $R^1$ is hydrogen, substituted or unsubstituted benzyl, substituted or unsubstituted phenyl. In some embodiments, $R^1$ is benzyl optionally substituted with, e.g., halogen, hydroxy, or nitro.

Certain aspects are directed to compounds having a formula of Formula IV.

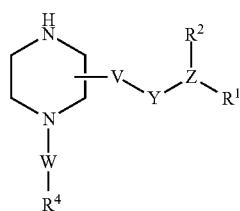

Formula IV

In certain aspects, Y, Z, $R^1$, and $R^2$ are as defined above with respect to Formula I. In certain embodiments of Formula IV, Y, Z, $R^1$, and $R^2$ are as defined above with respect to Formula III. $R^4$ is as defined with respect to Formula III above. In certain embodiments of Formula IV, R4 is substituted or unsubstituted aryl, e.g., unsubstituted phenyl, or substituted or unsubstituted heteroaryl.

In certain aspects, V is carbonyl, amino, or $(CH_2)_n$ wherein n is 1, 2, 3, 4, 5, or 6. In some aspects, V is carbonyl. In a further aspect, when Z is a —CH—, Y and V constitute a direct bond, and $R^2$ is hydrogen, $R^1$ can be an unsubstituted or substituted piperazine, or substituted or unsubstituted piperidine.

W is a direct bond; —$CH_2$—; sulfonyl; carbonyl; or linear or branched, saturated or unsaturated $C_2$, $C_3$, $C_4$, $C_5$, $C_6$, $C_7$, $C_8$, $C_9$, $C_{10}$, $C_{11}$, $C_{12}$, $C_{13}$, $C_{14}$, or $C_{15}$ alkyl. In certain embodiments, W is a direct bond.

Certain aspects are directed to compounds having a general formula of Formula V.

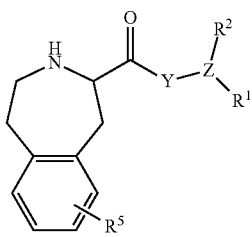

Formula V

In certain aspects, Y, Z, $R^1$, and $R^2$ are as defined above with respect to Formula I. For some embodiments of Formula V, Y is —NH—, and Z is linear or branched, saturated $C_{1-4}$ alkyl. For some embodiments of Formula V, $R^2$ is hydrogen, hydroxyl, or $C_{1-4}$ alkoxy. For some embodiments of Formula V, $R^1$ is hydroxyl, halo, substituted or unsubstituted aryl, or substituted or unsubstituted heterocyclyl. For some embodiments of Formula V, $R^1$ is substituted or unsubstituted 5- or 6-membered heterocycle containing 1 or 2 heteroatoms selected from nitrogen and oxygen, e.g., piperidine, pyrrolidine, piperazine, or morpholine. The optional substituent on the heterocycle can be, e.g., hydroxymethyl.

In certain aspects, $R^5$ is hydrogen or any of the optional substituents, which may be further optionally substituted, as described below. In certain aspects, $R^5$ is hydrogen.

Certain aspects are directed to compounds having a general formula of Formula VI.

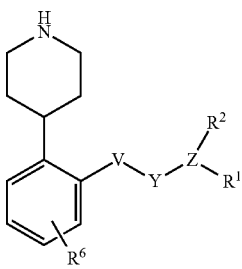

Formula VI

In certain aspects, Y, Z, $R^1$ and $R^2$ are as defined above with respect to Formula I. V is as defined above with respect to Formula IV. In certain embodiments of Formula VI, Y is —NH—, and Z is linear or branched, saturated $C_{1-4}$ alkyl. For some embodiments of Formula VI, $R^2$ is hydrogen, hydroxyl, or $C_{1-4}$ alkoxy. For some embodiments of Formula VI, $R^1$ is hydroxyl, halo, substituted or unsubstituted aryl (e.g., phenyl), or substituted or unsubstituted heterocyclyl. For some embodiments of Formula V, $R^1$ is substituted or unsubstituted 5- or 6-membered heterocycle containing 1 or 2 heteroatoms selected from nitrogen and oxygen, e.g., piperidine or morpholine. The optional substituent on the heterocycle can be, e.g., hydroxyl or hydroxymethyl.

In certain aspects, V is carbonyl, amino, or $(CH_2)_n$ wherein n is 1, 2, 3, 4, 5, or 6. In some aspects, V is carbonyl.

In certain aspects, $R^6$ is hydrogen or any of the optional substituents, which may be further optionally substituted, as described below. In certain aspects, $R^6$ is hydrogen.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention.

Throughout this application, the term "about" is used to indicate that a value includes the inherent variation of error for the device, the method being employed to determine the value, or the variation that exists among the study subjects.

The terms "comprise," "have," and "include" are open-ended linking verbs. Any forms or tenses of one or more of these verbs, such as "comprises," "comprising," "has," "having," "includes," and "including," are also open-ended.

For example, any method that "comprises," "has," or "includes" one or more steps is not limited to possessing only those one or more steps and also covers other unlisted steps.

As used herein, the term "$IC_{50}$" refers to an inhibitory dose that results in 50% of the maximum response obtained.

The term half maximal effective concentration ($EC_{50}$) refers to the concentration of a drug that presents a response halfway between the baseline and the maximum response after some specified exposure time.

The terms "inhibiting," "reducing," or "prevention," or any variation of these terms, when used in the claims and/or the specification includes any measurable decrease or complete inhibition to achieve a desired result.

The use of the term "or" in the claims is used to mean "and/or" unless explicitly indicated to refer to alternatives only or the alternatives are mutually exclusive, although the disclosure supports a definition that refers to only alternatives and "and/or."

As used herein, the term "patient" or "subject" refers to a living mammalian organism, such as a human, monkey, cow, sheep, goat, dogs, cat, mouse, rat, guinea pig, or species thereof. In certain embodiments, the patient or subject is a primate. Non-limiting examples of human subjects are adults, juveniles, infants and fetuses.

The use of the word "a" or "an" when used in conjunction with the term "comprising" in the claims and/or the specification may mean "one," but it is also consistent with the meaning of "one or more," "at least one," and "one or more than one."

BRIEF DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

FIG. 10A shows exemplary compounds of Formula I and II. FIG. 10B shows exemplary compounds of Formula I and III. FIG. 10C shows exemplary compounds of Formula I and IIIa. FIG. 10D shows exemplary compounds of Formula IV. FIG. 10E shows exemplary compounds of Formula V. FIG. 10F shows exemplary compounds of Formula VI.

DESCRIPTION

Figure 1:
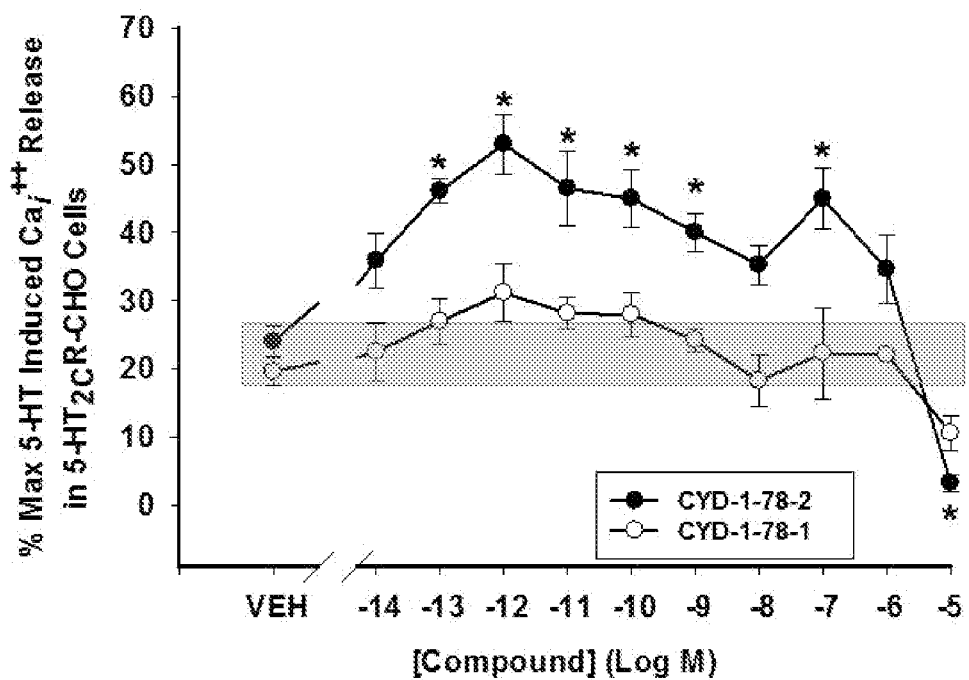
FIG. 1. Assessment of target molecules using a 5-HT induced intracellular calcium ($Ca_i^{++}$) release assay. In vitro $Ca_i^{++}$ release assay in live 5-$HT_{2C}$R—CHO cells. CYD-1-78-2 (PNU-69176E; ●) potentiated 5-HT (0.3 nM)-induced $Ca_i^{++}$ release in 5-$HT_{2C}$R—CHO cells, while its diastereomer CYD-1-78-1 (2; ○) had no effect. Data represent mean±SEM of four wells per concentration over at least three independent experiments and are expressed as % 5-$HT_{max}$ $Ca_i^{++}$ response determined at 1 μM 5-HT. *p<0.05 versus vehicle (VEH). Shaded area indicates the range of VEH response.

In recent years, multiple allosteric modulators of G-protein-coupled receptors (GPCRs) have been developed and predicted to have robust effects in a variety of CNS disorders (May et al., *Annu. Rev. Pharmacol. Toxicol.*, 47:1-51, 2007).

The recent preclinical indications of efficacy, coupled with the launch of cinacalcet and maraviroc as the first marketed GPCR allosteric modulators, validate the clinical utility of both positive and negative allosteric modulators (Conn et al., *Nature Reviews Drug Discovery*, 8:41-54, 2009). The studies reported to date provide proof of concept that will fuel the discovery of highly selective ligands for other GPCRs. Targeting allosteric modulation of the 5-HT$_{2C}$R to identify novel CNS probes with the potential for therapeutic application offers pharmacological advantages to a direct agonist or antagonist approach.

5-HT$_{2C}$R is a member of the serotonin receptor or 5-hydroxytryptamine receptor (5-HTR) family. The 5-HTRs are a group of G protein-coupled receptors (GPCRs) and ligand-gated ion channels (LGICs) found in the central and peripheral nervous systems that mediate both excitatory and inhibitory neurotransmission. The 5-HTR family includes 5-HT$_1$ to 5-HT$_7$ with each type having numerous receptor subtypes.

The 5-HTRs modulate the release of many neurotransmitters, including glutamate, GABA, dopamine, epinephrine/norepinephrine, and acetylcholine, as well as many hormones, including oxytocin, prolactin, vasopressin, cortisol, corticotropin, and substance P. The 5-HTRs influence various biological and neurological processes such as aggression, anxiety, appetite, cognition, learning, memory, mood, nausea, sleep, and thermoregulation; and are the target of a variety of pharmaceutical and illicit drugs, including many antidepressants, antipsychotics, anorectics, antiemetics, gastroprokinetic agents, antimigraine agents, hallucinogens, and entactogens.

The inventors have designed new molecules having improved c Log P values (an indicator of hydrophobicity) (c Log P less than 5) and therefore the potential for better drug-like properties. The compounds were designed to contain, for example, one or more of (a) an optimized polar head domain, (b) an optimized lipophilic binding domain, and/or (c) an optimized scaffold. Several highly potent ligands (nanomolar EC$_{50}$) are identified as selective allosteric modulators of 5-HT$_{2C}$R with positive, negative, or neutral allosteric modulator activity. Some of these compounds demonstrate >100 fold selectivity vs. 5-HT$_{2A}$R and 5-HT$_{2B}$R, or other receptors. Neutral allosteric ligand refers to an allosteric modulator that binds to the allosteric site but has no effects on the response to the orthosteric ligand.

I. ALLOSTERIC MODULATORS OF 5-HT$_{2C}$R

In biochemistry, allosteric regulation is the regulation of an enzyme or other protein by binding an effector molecule at the protein's allosteric site (that is, a site other than the protein's active site). Effectors that enhance the protein's activity are referred to as allosteric activators, whereas those that decrease the protein's activity are called allosteric inhibitors. Thus, a regulatory site of an allosteric protein is physically distinct from its active site. The compounds described herein are 5-HT$_{2C}$R allosteric modulators that are potential novel small molecules for modulating 5-HT$_{2C}$R activity. The compounds can be probes for the nervous system and/or therapeutics for the treatment of diseases, including, but not limited to addiction, anxiety, depression, obesity, eating disorders, Parkinson's disease, and schizophrenia. Examples of such compounds are provided in FIG. 10 and in the Examples section below. The compounds CYD-1-79, CYD-1-82 and CYD-1-84 demonstrate an EC$_{50}$ of 12.0±2.0 μM, 8.0±4.0 nM or 10.3±2.8 nM, respectively.

TABLE 1

List of some representative compounds.

| Compound Code | Structure | M.W. (g/mol) | Amount (mg) | Solubility |
|---|---|---|---|---|
| CYD-1-82 | 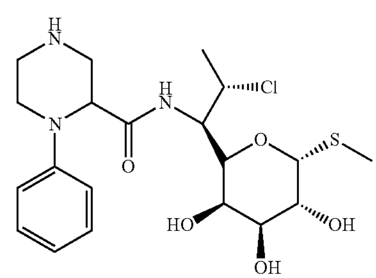 [SMILES: CS[C@H]1OC([C@@H](NC(=O)C2CNCCN2c2ccccc2)[C@H](C)Cl)[C@H](O)[C@H](O)[C@H]1O] | 459.9873 | 21 | EtOH, DMSO |
| CYD-1-84 | 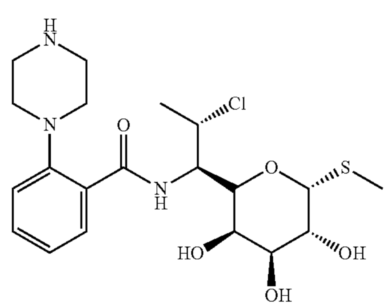 [SMILES: CS[C@H]1OC([C@@H](NC(=O)c2ccccc2N2CCNCC2)[C@H](C)Cl)[C@H](O)[C@H](O)[C@H]1O] | 458.9992 | 13 | H$_2$O, EtOH, DMSO |

TABLE 1-continued

List of some representative compounds.

| Compound Code | Structure | M.W. (g/mol) | Amount (mg) | Solubility |
|---|---|---|---|---|
| CYD-1-45 | 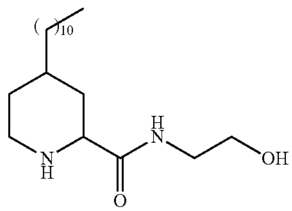 | 326.5172 | 35 | EtOH, DMSO |
| CYD-1-46 | 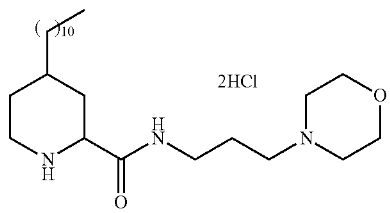 | 482.5708 | 100 | H₂O, EtOH, DMSO |
| CYD-1-79 | 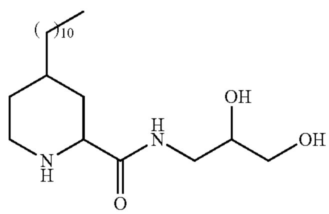 | 356.5432 | 23 | EtOH, DMSO |
| CYD-3-27 | 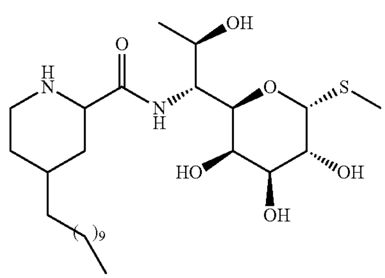 | 518.7500 | 30 | EtOH, DMSO |
| CYD-3-21 | 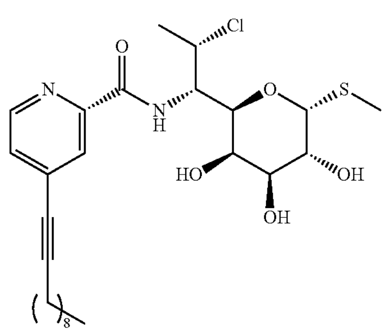 | 527.1163 | 20 | EtOH, DMSO |
| CYD-3-31 | 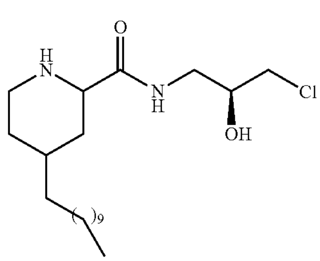 | 374.9889 | 35 | EtOH, DMSO |

TABLE 1-continued

List of some representative compounds.

| Compound Code | Structure | M.W. (g/mol) | Amount (mg) | Solubility |
|---|---|---|---|---|
| CYD-3-30 | 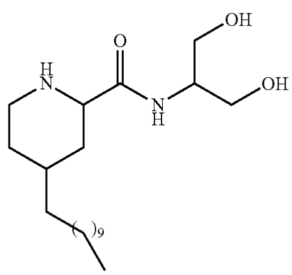 | 356.5432 | 35 | EtOH, DMSO |
| CYD-3-47-1 | 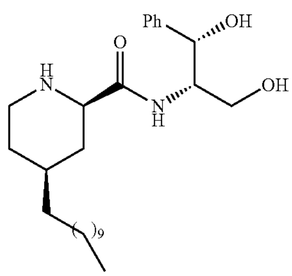 | 432.6392 | 14 | EtOH, DMSO |
| CYD-3-47-2 | 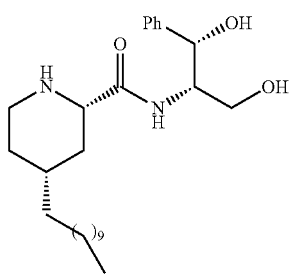 | 432.6392 | 15 | EtOH, DMSO |
| CYD-3-33 | 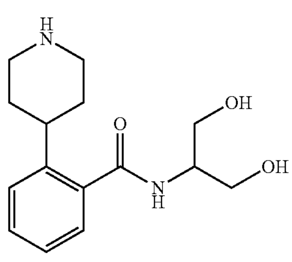 [SMILES: O=C(NC(CO)CO)c1ccccc1C1CCNCC1] | 278.3468 | 20 | EtOH, DMSO H2O |
| CYD-3-35 | 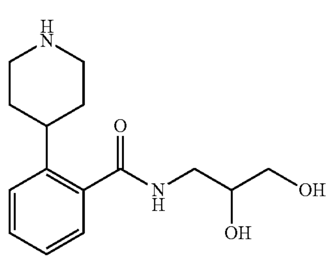 [SMILES: O=C(NCC(O)CO)c1ccccc1C1CCNCC1] | 278.3468 | 35 | EtOH, DMSO, H2O |

TABLE 1-continued
List of some representative compounds.
| Compound Code | Structure | M.W. (g/mol) | Amount (mg) | Solubility |
|---|---|---|---|---|
| CYD-3-49 | 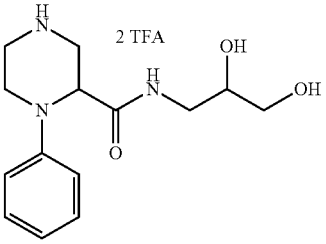 [SMILES: O=C(NCC(O)CO)C1CNCCN1c1ccccc1] | 507.3815 | 70 | EtOH, DMSO, H2O |
| CYD-3-50 | 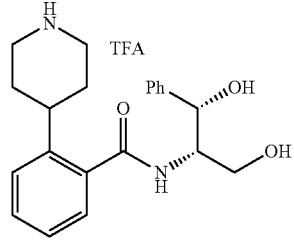 [SMILES: O=C(N[C@@H](CO)[C@@H](O)c1ccccc1)c1ccccc1C1CCNCC1] | 468.4661 | 65 | EtOH, DMSO, H2O |
| CYD-3-61 | 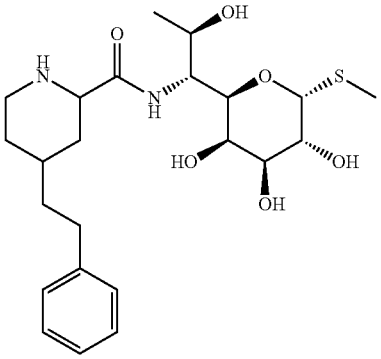 [SMILES: CS[C@H]1O[C@H]([C@H](NC(=O)C2CC(CCc3ccccc3)CCN2)[C@@H](C)O)[C@H](O)[C@H](O)[C@H]1O] | 468.6067 | 60 | EtOH, DMSO |
| CYD-3-62 | 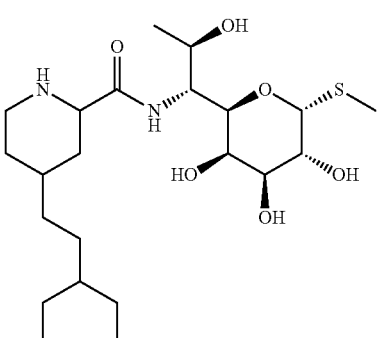 | 474.6544 | 40 | EtOH, DMSO |
| CYD-5-68-1 | 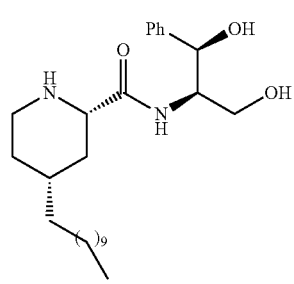 | 432.6392 | 25 | EtOH, DMSO |

TABLE 1-continued

List of some representative compounds.

| Compound Code | Structure | M.W. (g/mol) | Amount (mg) | Solubility |
|---|---|---|---|---|
| CYD-5-68-2 | 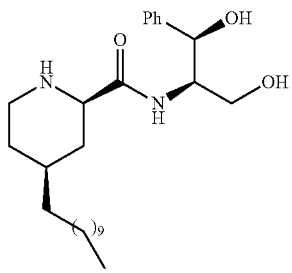 | 432.6392 | 25 | EtOH, DMSO |
| CYD-5-69 | 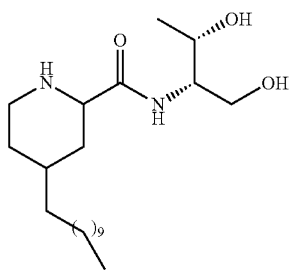 | 370.5698 | 25 | EtOH, DMSO |
| CYD-5-73 | 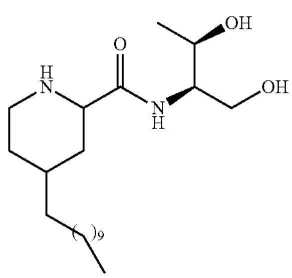 | 370.5698 | 30 | EtOH, DMSO |
| CYD-5-77-1 | 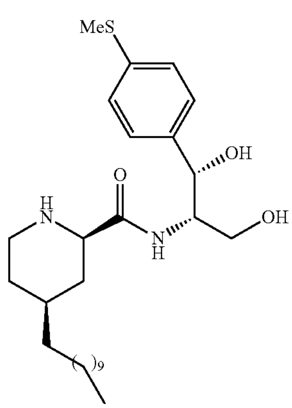 | 478.7307 | 25 | EtOH, DMSO |

TABLE 1-continued
List of some representative compounds.
| Compound Code | Structure | M.W. (g/mol) | Amount (mg) | Solubility |
|---|---|---|---|---|
| CYD-5-77-2 | 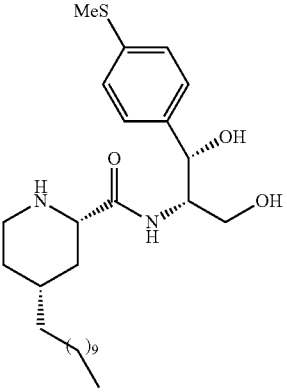 | 478.7307 | 30 | EtOH, DMSO |
| CYD-5-80-1 | 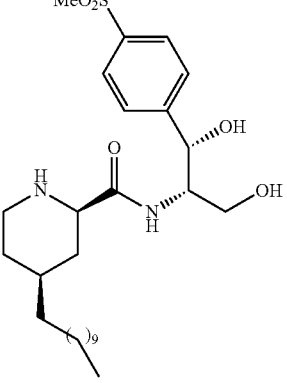 | 510.7295 | 25 | EtOH, DMSO |
| CYD-5-80-2 | 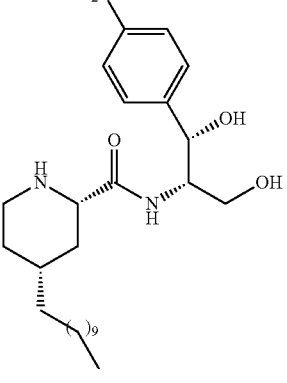 | 510.7295 | 25 | EtOH, DMSO |
| CYD-5-100-1 | 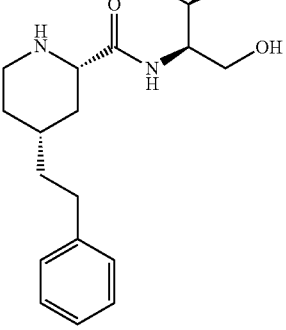 | 382.4959 | 28 | EtOH, DMSO |

TABLE 1-continued

List of some representative compounds.

| Compound Code | Structure | M.W. (g/mol) | Amount (mg) | Solubility |
|---|---|---|---|---|
| CYD-5-100-2 | 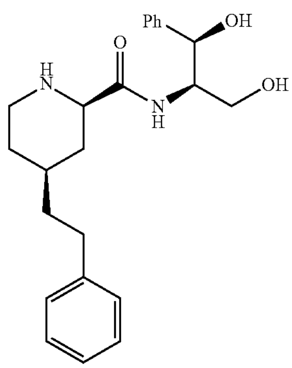 [SMILES: O=C(N[C@H](CO)[C@H](O)c1ccccc1)[C@H]1C[C@@H](CCc2ccccc2)CCN1] | 382.4959 | 30 | EtOH, DMSO |
| CYD-6-1-1 | 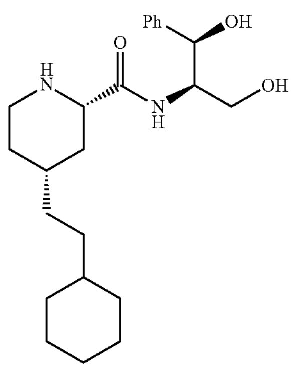 [SMILES: O=C(N[C@H](CO)[C@H](O)c1ccccc1)[C@@H]1C[C@H](CCC2CCCCC2)CCN1] | 388.5435 | 30 | EtOH, DMSO |
| CYD-6-1-2 | 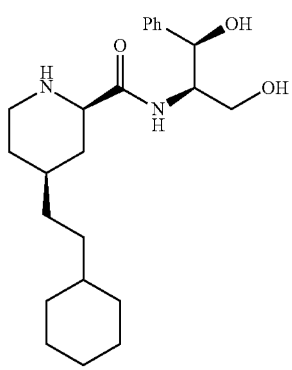 [SMILES: O=C(N[C@H](CO)[C@H](O)c1ccccc1)[C@H]1C[C@@H](CCC2CCCCC2)CCN1] | 388.5435 | 32 | EtOH, DMSO |
| CYD-6-2-1 | 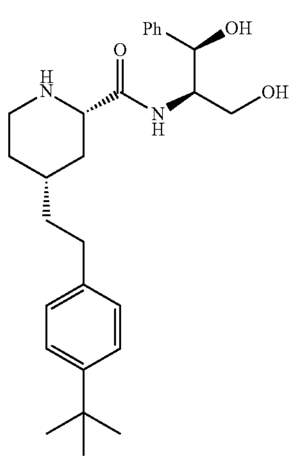 [SMILES: CC(C)(C)c1ccc(CC[C@@H]2CCN[C@H](C(=O)N[C@H](CO)[C@H](O)c3ccccc3)C2)cc1] | 438.6022 | 35 | EtOH, DMSO |

TABLE 1-continued
List of some representative compounds.
| Compound Code | Structure | M.W. (g/mol) | Amount (mg) | Solubility |
|---|---|---|---|---|
| CYD-6-2-2 | 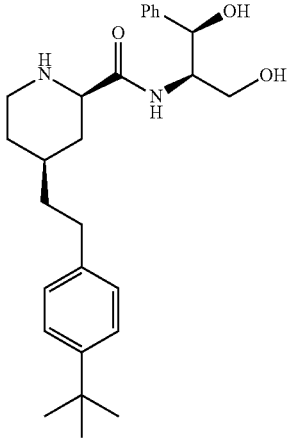 [SMILES: CC(C)(C)c1ccc(CC[C@H]2CCN[C@@H](C(=O)N[C@H](CO)[C@H](O)c3ccccc3)C2)cc1] | 438.6022 | 35 | EtOH, DMSO |
| CYD-6-9-1 | 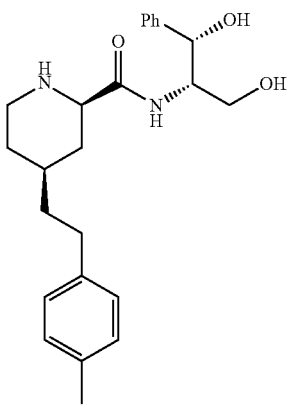 [SMILES: Cc1ccc(CC[C@H]2CCN[C@@H](C(=O)N[C@@H](CO)[C@@H](O)c3ccccc3)C2)cc1] | 396.5225 | 22 | EtOH, DMSO |
| CYD-6-9-2 | 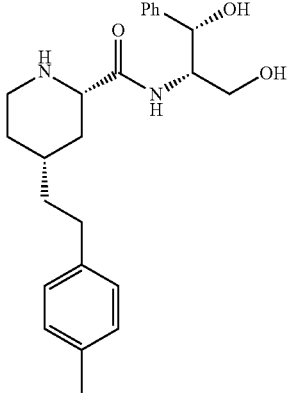 [SMILES: Cc1ccc(CC[C@@H]2CCN[C@H](C(=O)N[C@@H](CO)[C@@H](O)c3ccccc3)C2)cc1] | 396.5225 | 23 | EtOH, DMSO |

TABLE 1-continued
List of some representative compounds.
| Compound Code | Structure | M.W. (g/mol) | Amount (mg) | Solubility |
|---|---|---|---|---|
| CYD-6-10-1 | 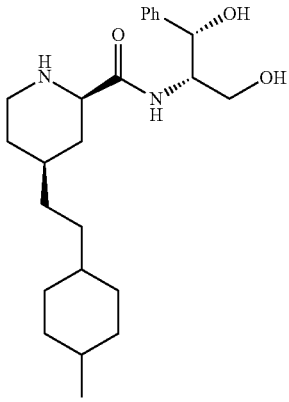 [SMILES: CC1CCC(CC[C@H]2CCN[C@@H](C(=O)N[C@@H](CO)[C@@H](O)c3ccccc3)C2)CC1] | 402.5701 | 24 | EtOH, DMSO |
| CYD-6-10-2 | 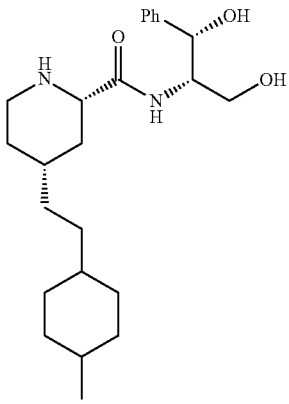 [SMILES: CC1CCC(CC[C@@H]2CCN[C@H](C(=O)N[C@@H](CO)[C@@H](O)c3ccccc3)C2)CC1] | 402.5701 | 25 | EtOH, DMSO |
| CYD-6-15-1 | 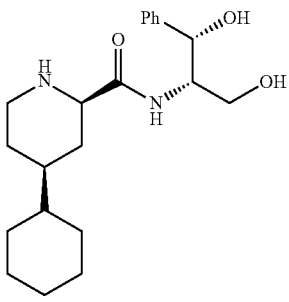 [SMILES: O=C(N[C@@H](CO)[C@@H](O)c1ccccc1)[C@H]1C[C@@H](C2CCCCC2)CCN1] | 360.4904 | 12 | EtOH, DMSO |
| CYD-6-15-2 | 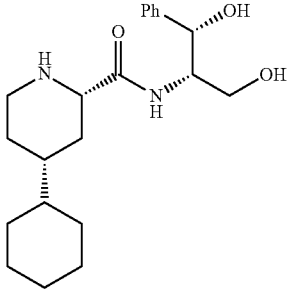 [SMILES: O=C(N[C@@H](CO)[C@@H](O)c1ccccc1)[C@@H]1C[C@H](C2CCCCC2)CCN1] | 360.4904 | 14 | EtOH, DMSO |

TABLE 1-continued

List of some representative compounds.

| Compound Code | Structure | M.W. (g/mol) | Amount (mg) | Solubility |
|---|---|---|---|---|
| CYD-6-16-1 | 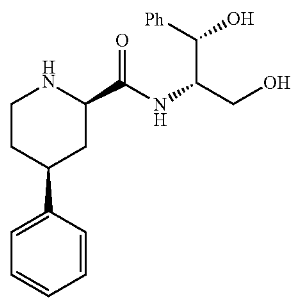 [SMILES: O=C(N[C@@H](CO)[C@@H](O)c1ccccc1)[C@H]1C[C@@H](c2ccccc2)CCN1] | 354.4427 | 18 | EtOH, DMSO |
| CYD-6-16-2 | 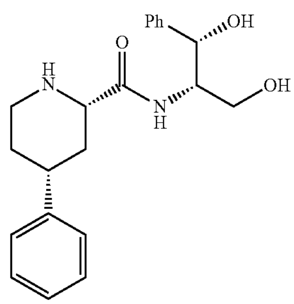 [SMILES: O=C(N[C@@H](CO)[C@@H](O)c1ccccc1)[C@@H]1C[C@H](c2ccccc2)CCN1] | 354.4427 | 19 | EtOH, DMSO |
| JZ-1-34 | 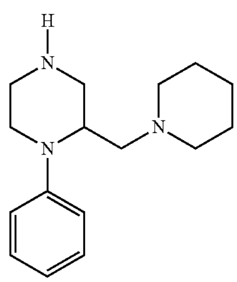 [SMILES: c1ccc(N2CCNCC2CN2CCCCC2)cc1] | 259.3898 | 110 | EtOH, DMSO |
| JZ-1-35 | 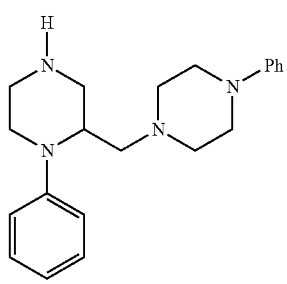 [SMILES: c1ccc(N2CCN(CC3CNCCN3c3ccccc3)CC2)cc1] | 336.4738 | 100 | EtOH, DMSO |

II. CHEMICAL DEFINITIONS

Various chemical definitions related to such compounds are provided as follows.

As used herein, "predominantly one enantiomer" means that the compound contains at least 85% of one enantiomer, or more preferably at least 90% of one enantiomer, or even more preferably at least 95% of one enantiomer, or most preferably at least 99% of one enantiomer. Similarly, the phrase "substantially free from other optical isomers" means that the composition contains at most 5% of another enantiomer or diastereomer, more preferably 2% of another enantiomer or diastereomer, and most preferably 1% of another enantiomer or diastereomer.

As used herein, the term "water soluble" means that the compound dissolves in water at least to the extent of 0.010 mole/liter or is classified as soluble according to literature precedence.

As used herein, the term "nitro" means —$NO_2$; the term "halo" designates —F, —Cl, —Br or —I; the term "mercapto" means —SH; the term "cyano" means —CN; the term "azido" means —$N_3$; the term "silyl" means —$SiH_3$, and the term "hydroxy" means —OH.

The term "alkyl," by itself or as part of another substituent, means, unless otherwise stated, a linear (i.e. unbranched) or branched carbon chain, which may be fully saturated, mono- or polyunsaturated. An unsaturated alkyl group is one having one or more double bonds or triple bonds. Saturated alkyl groups include those having one or more carbon-carbon double bonds (alkenyl) and those having one or more carbon-carbon triple bonds (alkenyl). The groups, —CH$_3$ (Me), —CH$_2$CH$_3$ (Et), —CH$_2$CH$_2$CH$_3$ (n-Pr), —CH(CH$_3$)$_2$ (iso-Pr), —CH$_2$CH$_2$CH$_2$CH$_3$ (n-Bu), —CH(CH$_3$)CH$_2$CH$_3$ (sec-butyl), —CH$_2$CH(CH$_3$)$_2$ (iso-butyl), —C(CH$_3$)$_3$ (tert-butyl), —CH$_2$C(CH$_3$)$_3$ (neo-pentyl), are all non-limiting examples of alkyl groups.

The term "heteroalkyl," by itself or in combination with another term, means, unless otherwise stated, a linear or branched chain having at least one carbon atom and at least one heteroatom selected from the group consisting of O, N, S, P, and Si. In certain embodiments, the heteroatoms are selected from the group consisting of O and N. The heteroatom(s) may be placed at any interior position of the heteroalkyl group or at the position at which the alkyl group is attached to the remainder of the molecule. Up to two heteroatoms may be consecutive. The following groups are all non-limiting examples of heteroalkyl groups: trifluoromethyl, —CH$_2$F, —CH$_2$Cl, —CH$_2$Br, —CH$_2$OH, —CH$_2$OCH$_3$, —CH$_2$ OCH$_2$CF$_3$, —CH$_2$OC(O)CH$_3$, —CH$_2$NH$_2$, —CH$_2$NHCH$_3$, —CH$_2$N(CH$_3$)$_2$, —CH$_2$CH$_2$Cl, —CH$_2$CH$_2$OH, CH$_2$CH$_2$OC(O)CH$_3$, —CH$_2$CH$_2$NHCO$_2$C(CH$_3$)$_3$, and —CH$_2$Si(CH$_3$)$_3$.

The terms "cycloalkyl" and "heterocyclyl," by themselves or in combination with other terms, means cyclic versions of "alkyl" and "heteroalkyl", respectively. Additionally, for heterocyclyl, a heteroatom can occupy the position at which the heterocycle is attached to the remainder of the molecule.

The term "aryl" means a polyunsaturated, aromatic, hydrocarbon substituent. Aryl groups can be monocyclic or polycyclic (e.g., 2 to 3 rings that are fused together or linked covalently). The term "heteroaryl" refers to an aryl group that contains one to four heteroatoms selected from N, O, and S. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

Various groups are described herein as substituted or unsubstituted (i.e., optionally substituted). Optionally substituted groups may include one or more substituents independently selected from: halogen, nitro, cyano, hydroxy, amino, mercapto, formyl, carboxy, oxo, carbamoyl, substituted or unsubstituted alkyl, substituted or unsubstituted heteroalkyl, alkoxy (e.g., methoxy), hydroxyalkyl (e.g., hydroxymethyl), alkylthio (e.g., methylthio), alkylamino, (alkyl)$_2$amino, alkylsulfinyl, alkylsulfonyl (e.g., methylsulfonyl), arylsulfonyl, substituted or unsubstituted cycloalkyl, substituted or unsubstituted heterocyclyl, substituted or unsubstituted aryl, and substituted or unsubstituted heteroaryl. In certain aspects the optional substituents may be further substituted with one or more substituents independently selected from: halogen, nitro, cyano, hydroxy, amino, mercapto, formyl, carboxy, carbamoyl, unsubstituted alkyl, unsubstituted heteroalkyl, alkoxy, alkylthio, alkylamino, (alkyl)$_2$-amino, alkylsulfinyl, alkylsulfonyl, arylsulfonyl, unsubstituted cycloalkyl, unsubstituted heterocyclyl, unsubstituted aryl, or unsubstituted heteroaryl. Exemplary optional substituents include, but are not limited to: —OH, oxo (=O), —Cl, —F, Br, C$_{1-4}$alkyl, phenyl, benzyl, —NH$_2$, —NH(C$_{1-4}$alkyl), —N(C$_{1-4}$alkyl)$_2$, —NO$_2$, —S(C$_{1-4}$alkyl), —SO$_2$(C$_{1-4}$alkyl), —CO$_2$(C$_{1-4}$alkyl), and —O(C$_{1-4}$alkyl).

The term "alkoxy" means a group having the structure —OR', where R' is an optionally substituted alkyl or cycloalkyl group. The term "heteroalkoxy" similarly means a group having the structure —OR, where R is a heteroalkyl or heterocyclyl.

The term "amino" means a group having the structure —NR'R", where R' and R" are independently hydrogen or an optionally substituted alkyl, heteroalkyl, cycloalkyl, or heterocyclyl group. The term "amino" includes primary, secondary, and tertiary amines.

The term "oxo" as used herein means an oxygen that is double bonded to a carbon atom.

The term "alkylsulfonyl" as used herein means a moiety having the formula —S(O$_2$)—R', where R' is an alkyl group. R' may have a specified number of carbons (e.g. "C$_{1-4}$ alkylsulfonyl")

The term "monosaccharide" refers to a cyclized monomer unit based on a compound having a chemical structure H(CHOH)$_n$C(=O)(CHOH)$_m$H wherein n+m is 4 or 5. Thus, monosaccharides include, but are not limited to, aldohexoses, aldopentoses, ketohexoses, and ketopentoses such as arabinose, lyxose, ribose, xylose, ribulose, xylulose, allose, altrose, galactose, glucose, gulose, idose, mannose, talose, fructose, psicose, sorbose, and tagatose.

The term "pharmaceutically acceptable salts," as used herein, refers to salts of compounds of this invention that are substantially non-toxic to living organisms. Typical pharmaceutically acceptable salts include those salts prepared by reaction of a compound of this invention with an inorganic or organic acid, or an organic base, depending on the substituents present on the compounds of the invention.

Non-limiting examples of inorganic acids which may be used to prepare pharmaceutically acceptable salts include: hydrochloric acid, phosphoric acid, sulfuric acid, hydrobromic acid, hydroiodic acid, phosphorous acid and the like. Examples of organic acids which may be used to prepare pharmaceutically acceptable salts include: aliphatic mono- and dicarboxylic acids, such as oxalic acid, carbonic acid, citric acid, succinic acid, phenyl-heteroatom-substituted alkanoic acids, aliphatic and aromatic sulfuric acids and the like. Pharmaceutically acceptable salts prepared from inorganic or organic acids thus include hydrochloride, hydrobromide, nitrate, sulfate, pyrosulfate, bisulfate, sulfite, bisulfate, phosphate, monohydrogenphosphate, dihydrogenphosphate, metaphosphate, pyrophosphate, hydroiodide, hydro fluoride, acetate, propionate, formate, oxalate, citrate, lactate, p-toluenesulfonate, methanesulfonate, maleate, and the like.

Suitable pharmaceutically acceptable salts may also be formed by reacting the agents of the invention with an organic base such as methylamine, ethylamine, ethanolamine, lysine, ornithine and the like. Pharmaceutically acceptable salts include the salts formed between carboxylate or sulfonate groups found on some of the compounds of this invention and inorganic cations, such as sodium, potassium, ammonium, or calcium, or such organic cations as isopropylammonium, trimethylammonium, tetramethylammonium, and imidazolium.

It should be recognized that the particular anion or cation forming a part of any salt of this invention is not critical, so long as the salt, as a whole, is pharmacologically acceptable.

Additional examples of pharmaceutically acceptable salts and their methods of preparation and use are presented in Handbook of Pharmaceutical Salts: Properties, Selection and Use (2002), which is incorporated herein by reference.

An "isomer" of a first compound is a separate compound in which each molecule contains the same constituent atoms as the first compound, but where the configuration of those atoms in three dimensions differs. Unless otherwise specified, the compounds described herein are meant to encompass their isomers as well. A "stereoisomer" is an isomer in which the same atoms are bonded to the same other atoms, but where the configuration of those atoms in three dimensions differs. "Enantiomers" are stereoisomers that are mirror images of each other, like left and right hands. "Diastereomers" are stereoisomers that are not enantiomers.

It is contemplated that any embodiment discussed in this specification can be implemented with respect to any method or composition of the invention, and vice versa. Furthermore, compositions of the invention can be used to achieve methods of the invention.

III. EXAMPLES

The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

A. Results

Figure 2:
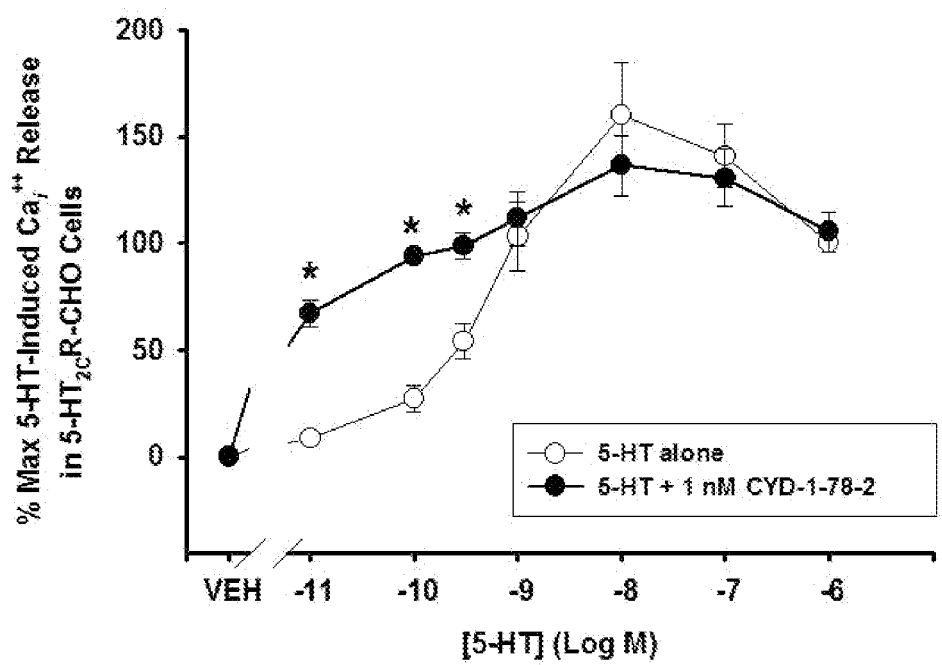
FIG. 2. Assessment of target molecules using a 5-HT induction of intracellular calcium ($Ca_i^{++}$) release assay. In vitro $Ca_i^{++}$ release assay in live 5-$HT_{2C}$R—CHO cells. CYD-1-78-2 (PNU-69176E; ●) (1 nM) enhanced the $Ca_i^{++}$ release induced by low concentrations of 5-HT (○). Data represent mean±SEM of four wells per concentration over at least three independent experiments and are expressed as % 5-$HT_{max}$ $Ca_i^{++}$ response determined at 1 μM 5-HT. *p<0.05 versus 5-HT alone.
Figure 3:
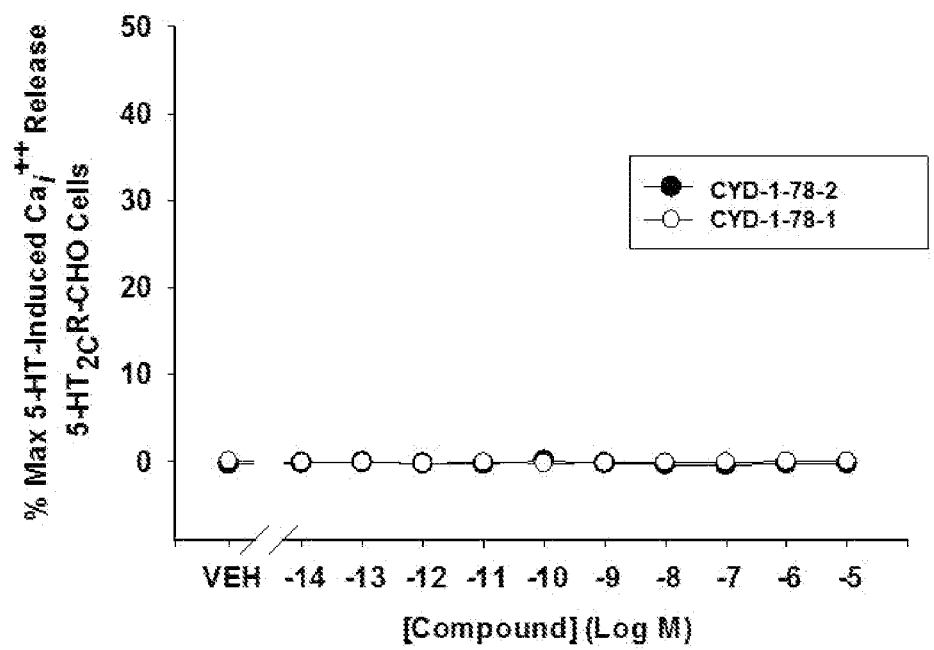
FIG. 3. Assessment of target molecules using a 5-HT induction of intracellular calcium ($Ca_i^{++}$) release assay. In vitro $Ca_i^{++}$ release assay in live 5-$HT_{2C}$R—CHO cells. In the absence of 5-HT, neither CYD-1-78-2 (PNU-69176E; ●) nor its diastereomer CYD-1-78-1 (2; ○) affected $Ca_i^{++}$ release in 5-$HT_{2C}$R—CHO cells. Data represent mean±SEM of four wells per concentration over at least three independent experiments and are expressed as % 5-$HT_{max}$ $Ca_i^{++}$ response determined at 1 μM 5-HT.
Figure 4:
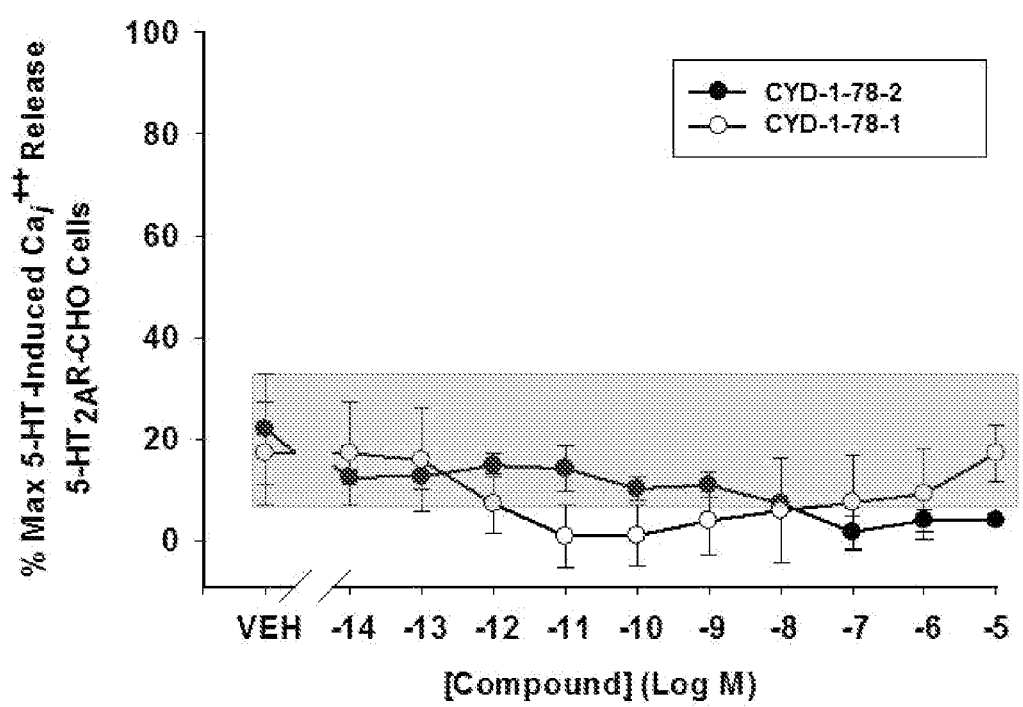
FIG. 4. Assessment of target molecules using a 5-HT induction of intracellular calcium ($Ca_i^{++}$) release assay. In vitro $Ca_i^{++}$ release assay in live 5-$HT_{2A}$R—CHO cells. Neither CYD-1-78-2 (PNU-69176E; ●) nor its diastereomer CYD-1-78-1 (2; ○) altered 5-HT-induced $Ca_i^{++}$ release in 5-$HT_{2A}$R—CHO cells. Data represent mean±SEM of four wells per concentration over at least three independent experiments and are expressed as % 5-$HT_{max}$ $Ca_i^{++}$ response determined at 1 μM 5-HT. Shaded area indicates the range of VEH response.

Selected results for the biological characterization of the synthesized compounds can be found in Ding et al., *ACS Chem. Neurosci.*, 3, 538-545, 2012, and also described herein. The biological activity is assessed using an intracellular calcium ($Ca_i^{++}$) release assay. The best-characterized intracellular signaling pathway of the 5-$HT_{2C}R$ is the activation of phospholipase C (PLCβ) via Gαq/11 proteins and the production of diacylglycerol (DAG) and inositol-1,4,5-trisphosphate (IP3), leading to increased $Ca_i^{++}$ release from intracellular stores (Berg et al., *Neuropharmacology* 55, 969-76, 2008). Functional characterization of our synthetic PNU-69176E (CYD-1-78-2) and its diastereomer CYD-1-78-1 was determined by utilizing an $Ca_i^{++}$ release assay in live cells in which $Ca_i^{++}$ levels can be regarded as an outcome measure of activation of the 5-$HT_{2C}R$ signaling pathway (Berg et al., *Neuropharmacology* 55, 969-76, 2008). Biological analyses conducted in Chinese hamster ovary cells (CHO) stably expressing physiological levels of the human 5-$HT_{2C}R$ (5-$HT_{2C}R$—CHO) showed that compound CYD-1-78-2 potentiated the $Ca_i^{++}$ release induced by 0.3 nM 5-HT (~5-HT $EC_{20}$) from 23.9% of a maximal 5-HT-induced $Ca_i^{++}$ release (5-$HT_{max}$; determined at 1 μM 5-HT) to 48.5% of 5-$HT_{max}$ [$F_{(10,51)}$=9.01, p<0.01; FIG. 1]. A priori comparisons using Dunnett's procedure revealed that compound CYD-1-78-2 significantly enhanced $Ca_i^{++}$ release above that of 0.3 nM 5-HT alone at concentrations in the range of $10^{-13}$-$10^{-7}$ M and reduced $Ca_i^{++}$ release at the highest concentration utilized ($10^{-5}$ M) (p<0.05). In addition, 1 nM of compound CYD-1-78-2 enhanced the $Ca_i^{++}$ response at low concentrations of 5-HT [$10^{11}$-3×$10^{-10}$ M; $F_{(15,55)}$=16.73, p<0.01; FIG. 2]. In contrast, the diastereomer CYD-1-78-1 did not alter $Ca_i^{++}$ release evoked by 0.3 nM 5-HT [$F_{(9,32)}$=2.04, n.s.; FIG. 1]. Neither compound CYD-1-78-2 [$F_{(10,68)}$=0.81, n.s.] nor the diastereomer CYD-1-78-1 [$F_{(10,34)}$=0.76, n.s.] in concentrations up to $10^{-5}$ M induced $Ca_i^{++}$ release in the 5-$HT_{2C}R$—CHO cells in the absence of 5-HT (FIG. 3). This profile for compounds CYD-1-78-2 and -1 in 5-$HT_{2C}R$—CHO cells was distinguished from that seen in 5-$HT_{2A}R$—CHO cells in which neither compound alone or in the presence of 5-HT (compound CYD-1-78-1, $F_{(10,43)}$=0.78; compound CYD-1-78-2, $F_{(10,55)}$=1.27; FIG. 4) altered $Ca_i^{++}$ release (Ding et al., *ACS Chem. Neurosci.* 3, 538-545, 2012).

Multiple allosteric modulators of G-protein-coupled receptors have been developed and predicted to have robust effects in a variety of CNS disorders. Preliminary data with the lead compound CYD-1-78-2 demonstrate the ability to detect positive, and perhaps negative, allosteric activity (FIG. 1) selectively at the 5-$HT_{2C}R$ versus the highly homologous 5-$HT_{2A}R$. Compound CYD-1-78-2 produced the anticipated characteristics based upon a previous study (Im et al., *Mol. Pharmacol.* 64, 78-84, 2003) which identified positive allosteric modulation by PNU-69176E in the presence of 5-HT at concentrations less than 10 μM and negative allosteric modulation at higher concentrations. These investigators also detected intrinsic activation of GTPγS binding and inositol 1,4,5-triphosphate (IP3) release/ [³H]IP accumulation by PNU-69176E in the absence of 5-HT; in contrast, the inventors did not detect intrinsic agonist activity for compound CYD-1-78-2 in the 5-$HT_{2C}R$ induced $Ca_i^{++}$ release assay (FIG. 3). Such differences may be attributable to the choice of expression system and the protein expression level for the 5-$HT_{2C}R$. In the present studies, the inventors employed a stably transfected CHO cell line (~250 fmol/mg protein) which expresses vastly lower levels of the 5-$HT_{2C}R$ protein relative to the stably transfected HEK293 cell line (~45 pmol/mg protein) used in the previous report (Im et al., *Mol. Pharmacol.* 64, 78-84, 2003). These technical aspects highlight the nuances that have hampered GPCR allosteric modulator drug discovery in the past, but also present new prospects for preclinical lead discovery.

Figure 5:
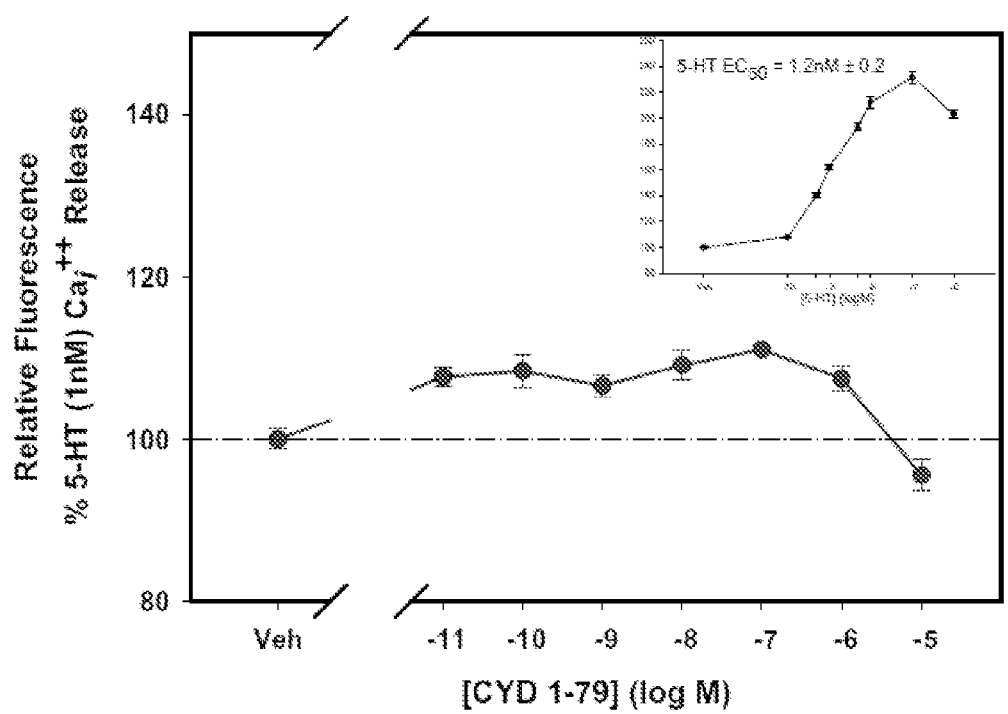
FIG. 5. Assessment of target molecules using a 5-HT induction of intracellular calcium ($Ca_i^{++}$) release assay. In vitro $Ca_i^{++}$ release assay in live 5-$HT_{2C}$R—CHO cells. CYD-1-79 potentiated 5-HT-induced $Ca_i^{++}$ release in 5-$HT_{2C}$R—CHO cells.
Figure 6:
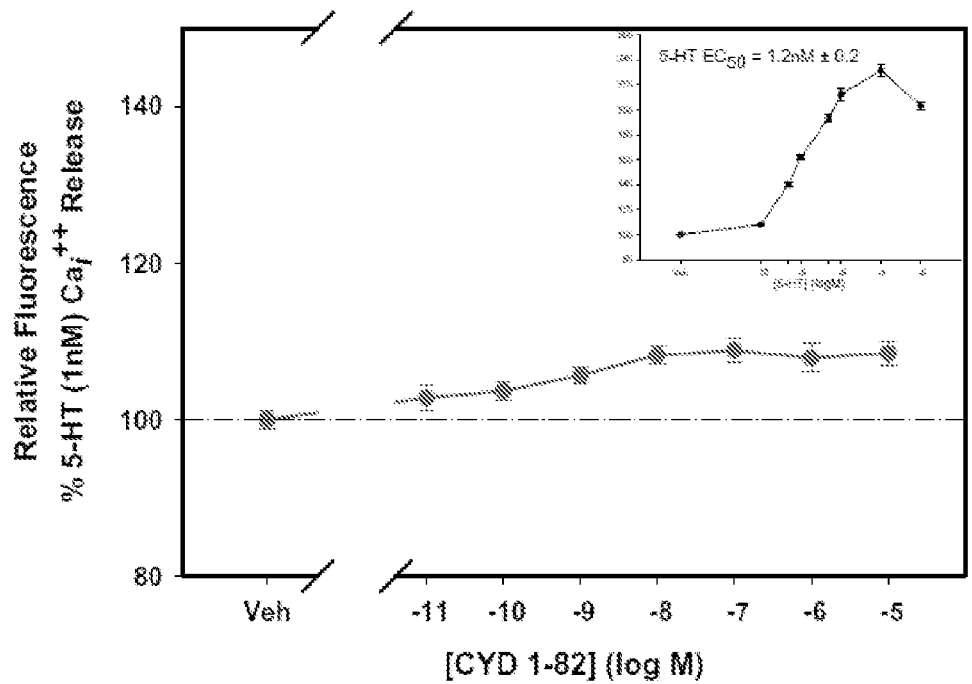
FIG. 6. Assessment of target molecules using a 5-HT induction of intracellular calcium ($Ca_i^{++}$) release assay. In vitro $Ca_i^{++}$ release assay in live 5-$HT_{2C}$R—CHO cells. CYD-1-82 potentiated 5-HT-induced $Ca_i^{++}$ release in 5-$HT_{2C}$R—CHO cells.
Figure 7:
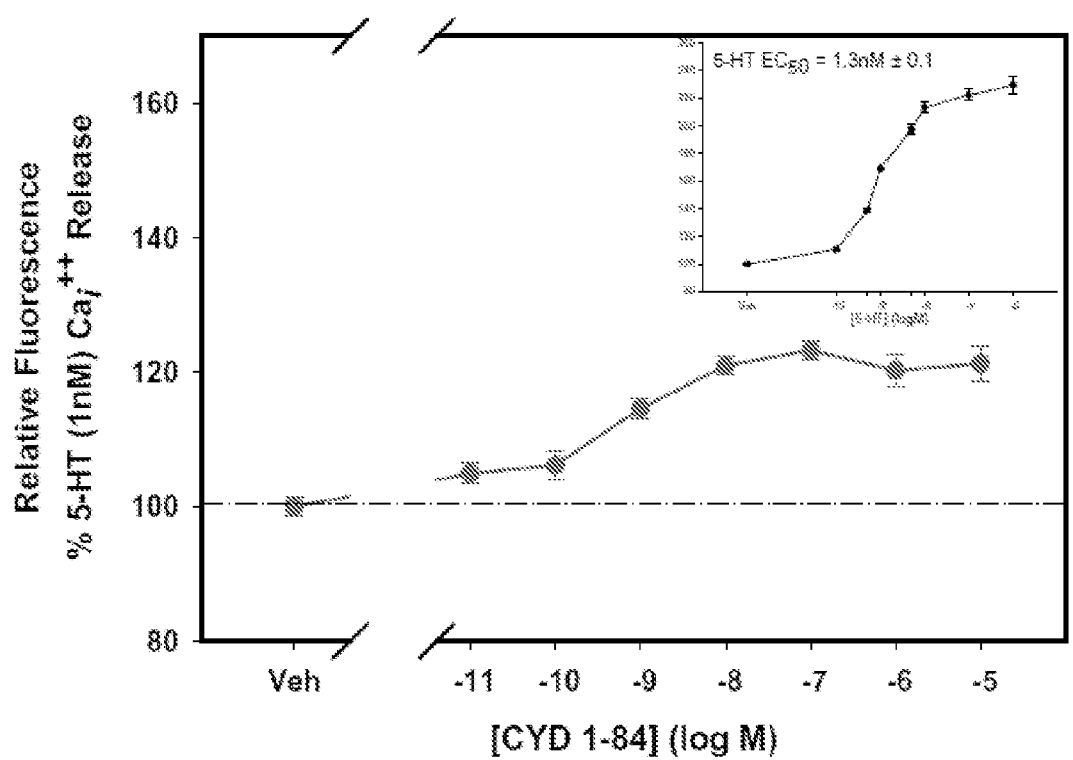
FIG. 7. Assessment of target molecules using a 5-HT induction of intracellular calcium ($Ca_i^{++}$) release assay. In vitro $Ca_i^{++}$ release assay in live 5-$HT_{2C}$R—CHO cells. CYD-1-84 potentiated 5-HT-induced $Ca_i^{++}$ release in 5-$HT_{2C}$R—CHO cells.

Three additional derivatives evaluated (CYD-1-79, -82, and -84) also enhanced 5-HT-induced $Ca_i^{++}$ release (FIGS. 5, 6, and 7), indicating these new molecules act as positive allosteric modulators for 5-HT-induced intracellular calcium release in these cells.

Figure 8A:
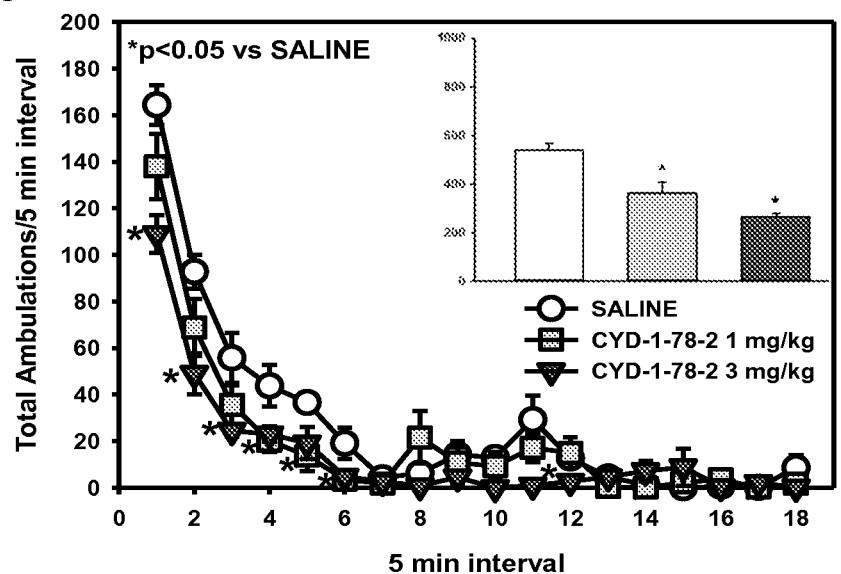
FIG. 8. In vivo locomotor activity studies for CYD-1-78-2. The 5-$HT_{2C}$R positive allosteric modulator CYD-1-78-2 (PNU-69176E) suppresses motor activity alone (A) and in combination with the 5-$HT_{2C}$R agonist WAY163909 (B). In vivo locomotor activity studies in unhabituated animals. A) CYD-1-78-2 (1; 1 and 3 mg/kg, i.p.) dose-dependently decreases total ambulations. The combination of low doses of CYD-1-78-2 (1; 0.5 mg/kg, i.p.) plus the 5-$HT_{2C}$R agonist WAY163909 (1 mg/kg, i.p.) reduces total ambulations at doses that do not alter total ambulations on their own. Unhabituated animals were injected with CYD-1-78-2 or WAY163909 alone or in combination and immediately placed in locomotor chambers. Total ambulations were recorded over 90 minutes. Data are presented in 5 minute intervals (time course) or as total counts over the entire 90 minute session (inset bar graph).
Figures 9A, 9B:
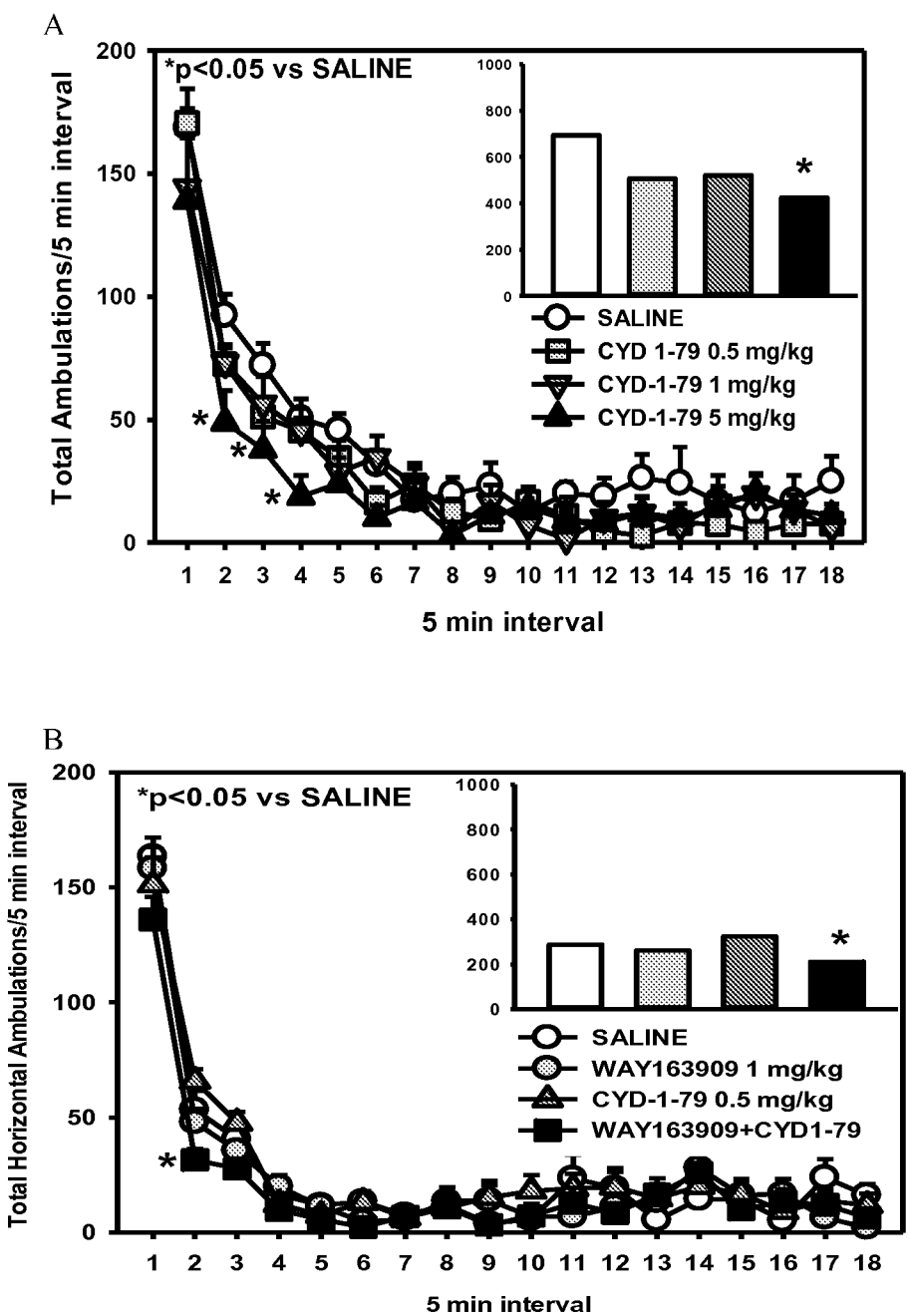
FIGS. 9A-9B. In vivo locomotor activity studies for CYD-1-79. (A) Unhabituated animals were treated with a single dose of CYD-1-79 immediately prior to start of locomotor assessment. n=7-8/group. (B) Using a within-subjects repeated-measures design, habituated animals were treated with WAY 163909 (1 mg/kg) or saline immediately prior to CYD-1-79 (0.5 mg/kg) or saline treatment. Locomotor assessment began immediately following second injection. Animals received each treatment combination for a total of 4 tests. N=10.
Figure 10A:
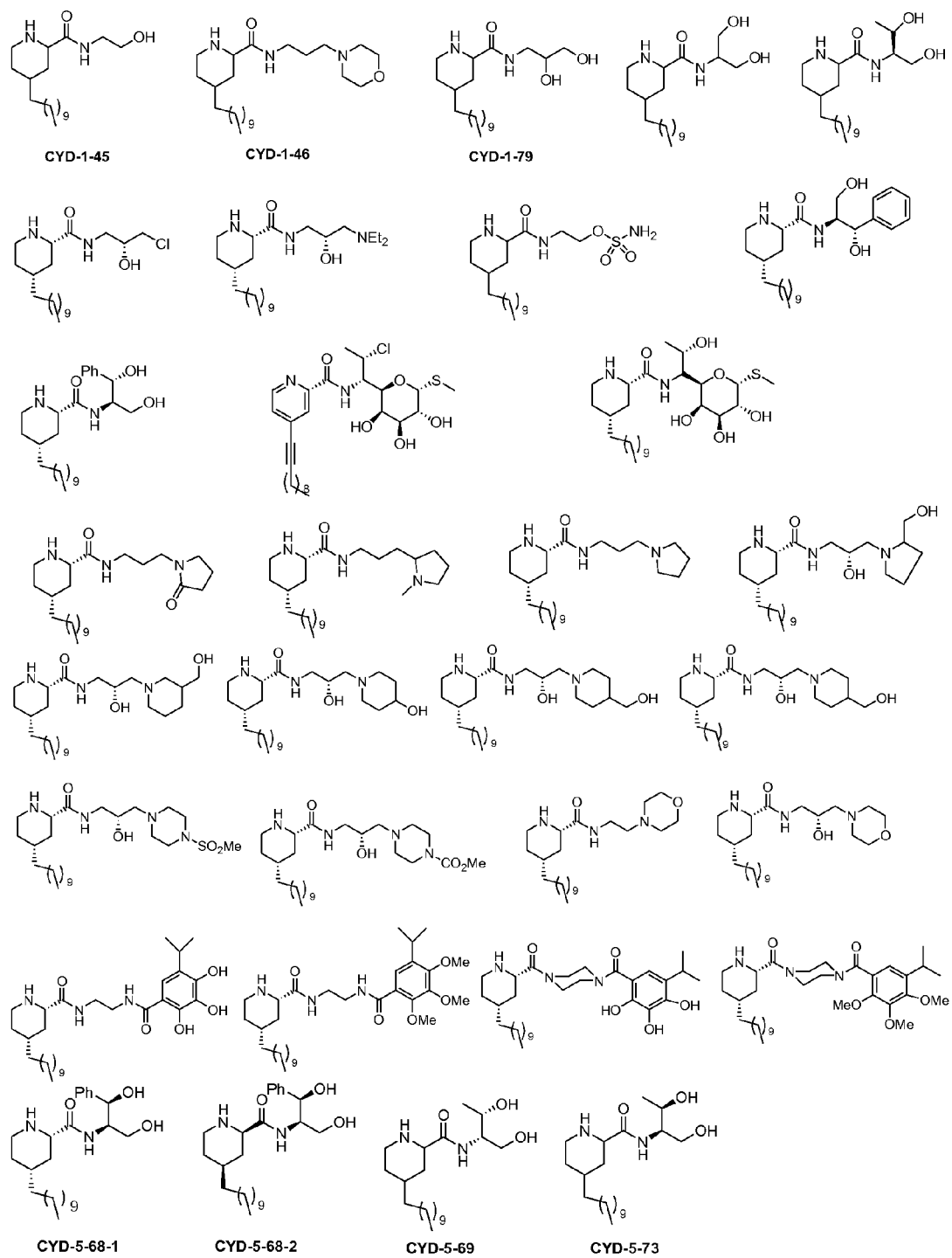
FIGS. 10A-10F. Chemical structures of 5-$HT_{2C}$R modulator family of compounds.
Figure 10A:
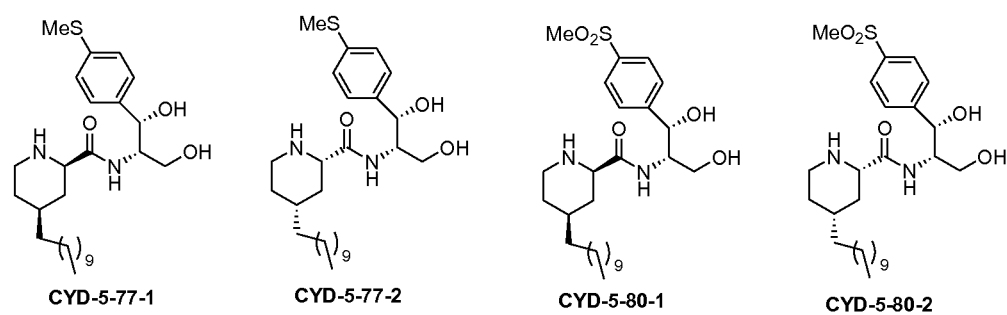
Figure 10B:
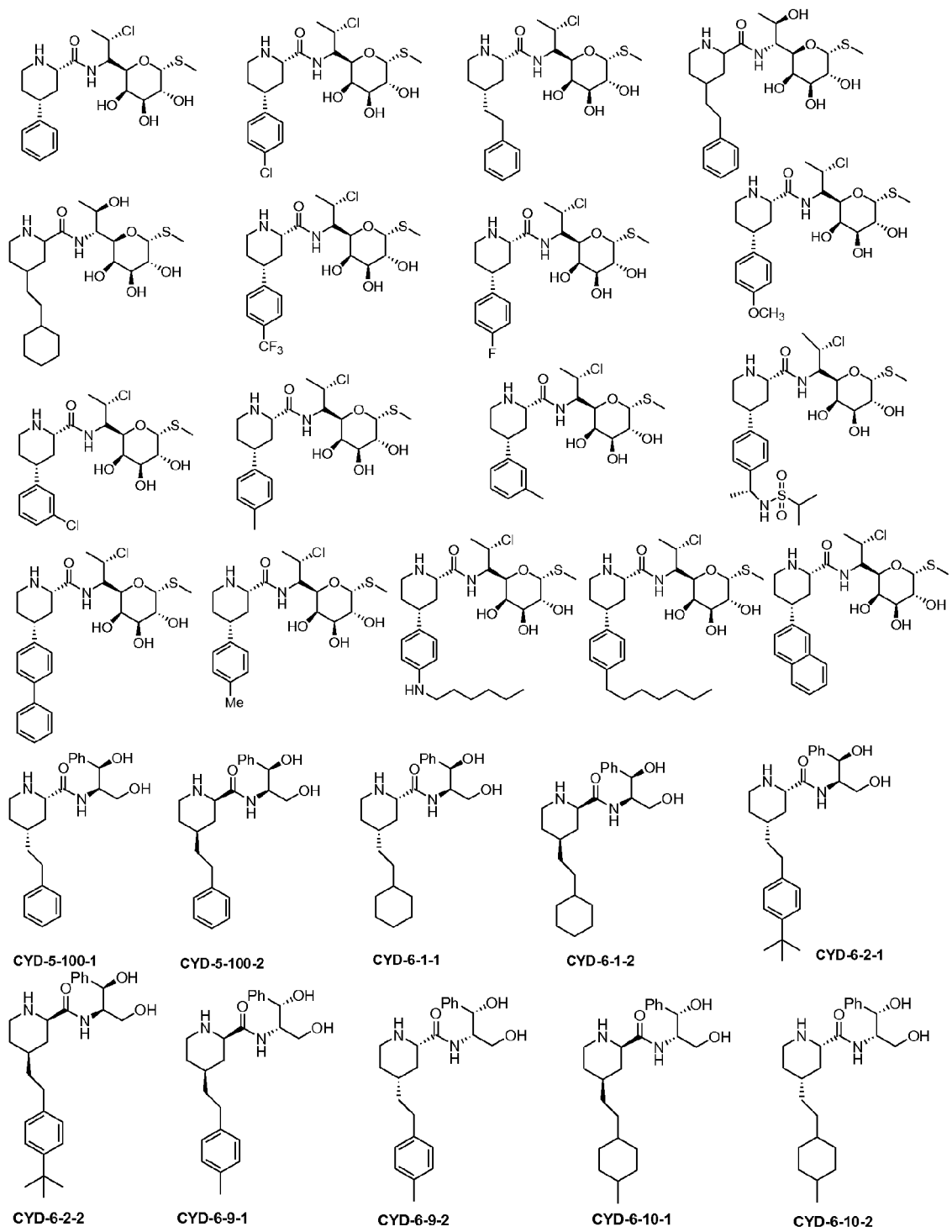
Figure 10B:
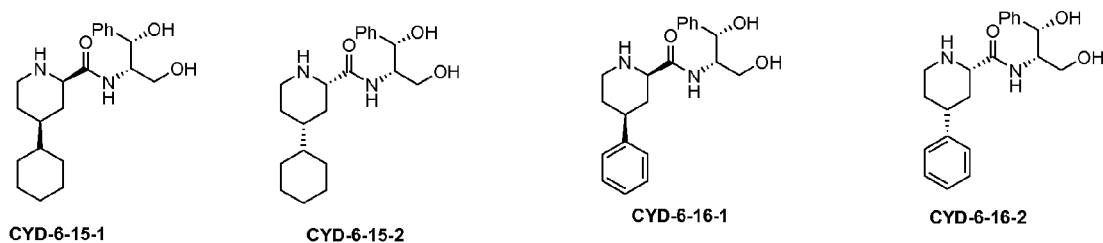
Figure 10C:
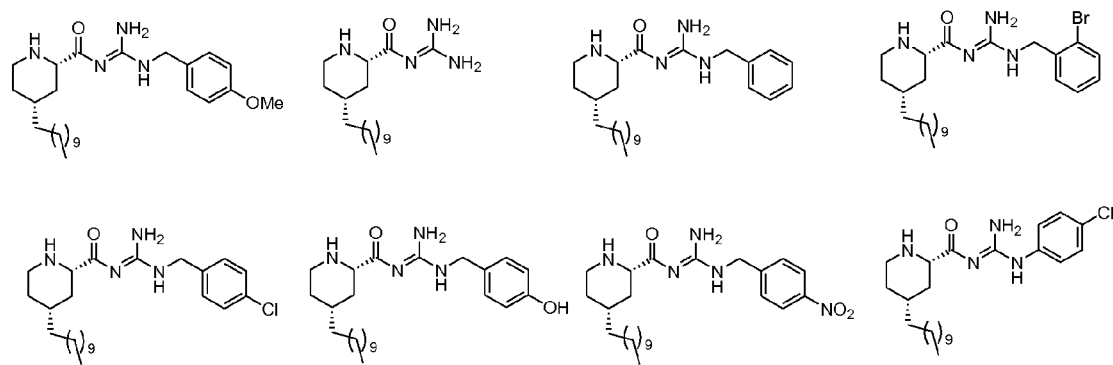
Figure 10D:
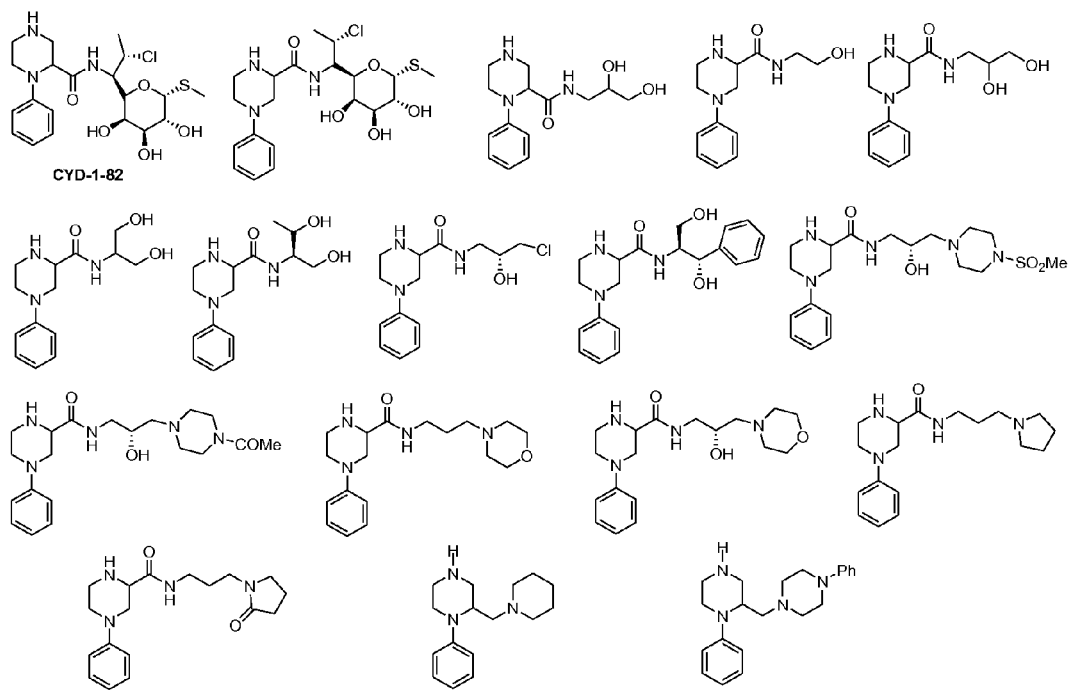
Figure 10E:
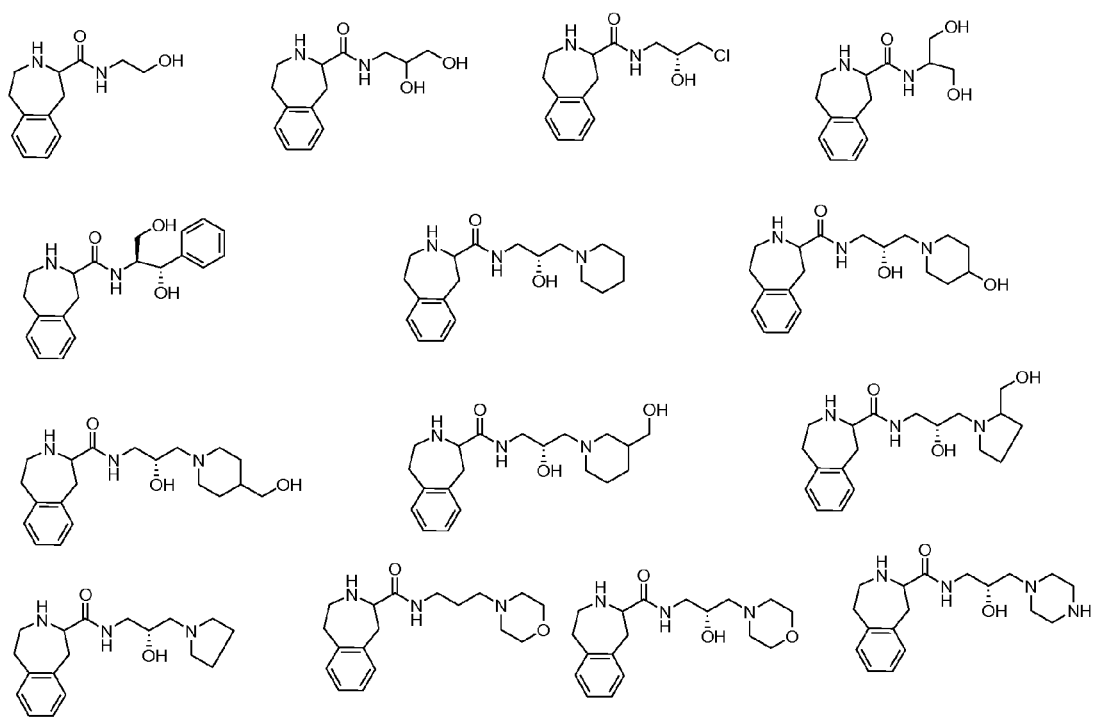
Figure 10F:
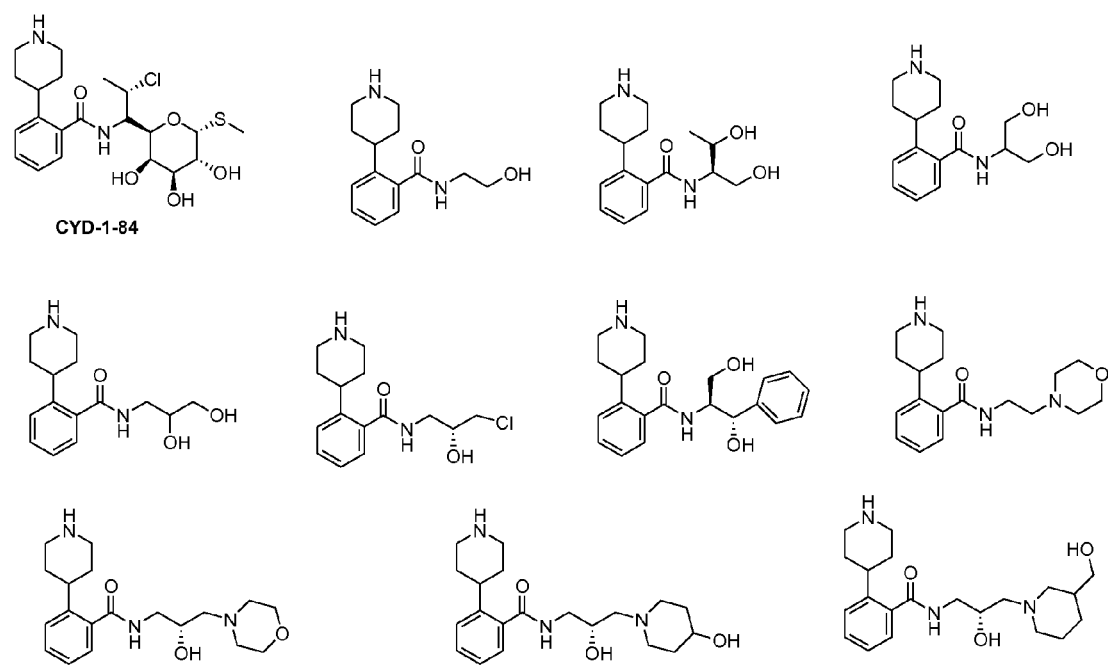

Several 5-$HT_{2C}R$ agonists are reported to suppress ambulation in rodents (Halford et al., 1997 *Pharmacol. Biochem. Behav.* 56:41-46; Halberstadt et al., 2009, *Neuropsychopharmacol.* 34:1958-1967; Cunningham et al., 2011, *Neuropharmacology* 61:513-523; Grottick et al., 2000, *J. Pharmacol. Exp. Ther.* 295:1183-1191; Fletcher et al., 2002, *Neuropsychopharmacol.* 27:576-586; Cunningham et al., *ACS Chem. Neurosci.*, Accepted Aug. 11, 2012). Herein, the inventors assess the effects of CYD-1-78-2 (1 or 3 mg/kg) and CYD-1-79 (0.5, 1, or 1.5 mg/kg) on outcome measures obtained from analyses of spontaneous locomotor activity. For CYD-1-78-2, a main effect of treatment [$F_{(2,342)}$=22.28, p<0.0001], time [$F_{(17,3427)}$=94.10, p<0.0001], and a treatment×time interaction [$F_{(34,342)}$=2.48, p<0.0001], is observed for horizontal ambulation divided into eighteen 5-min intervals (FIG. 8A). CYD-1-78-2 at 1 mg/kg significantly reduces horizontal ambulation versus saline at interval 4, interval 5, and interval 6 (p<0.05; FIG. 8A). CYD-1-78-2 at 3 mg/kg significantly reduces horizontal ambulation versus saline at interval 1, interval 2, interval 3, and interval 11 (p<0.05; FIG. 8A). A main effect of CYD-1-78-2 treatment is observed for total horizontal ambulation totaled across the 90-min test session [$F_{(2,18)}$=14.47, p<0.001; FIG. 8A, inset]; a priori comparisons reveal that 1 and 3 mg/kg of CYD-1-78-2 significantly reduces total horizontal ambulation summed across the 90-min test session versus saline (p<0.05; FIG. 8A, inset). For CYD-1-79, a main effect of treatment [$F_{(3,450)}$=12.03, p<0.0001], time [$F_{(17,450)}$=81.43, p<0.0001], but no treatment×time interaction [$F_{(51,450)}$=0.97, n.s.], is observed for horizontal ambulation divided into eighteen 5-min intervals (FIG. 9A). CYD-1-79 at 5 mg/kg significantly reduces horizontal ambulation versus saline at interval 2, interval 3, and interval 4 (p<0.05; FIG. 9). A trend towards a main effect of CYD-1-79 treatment is observed for total horizontal ambulation totaled across the 90-min test session [$F_{(3,25)}$=2.39, p=0.09; FIG. 9A, inset]; a priori comparisons revealed that 5 mg/kg of CYD-1-79 significantly reduces total horizontal ambulation versus saline (p<0.05; FIG. 9A, inset).

Figure 8B:
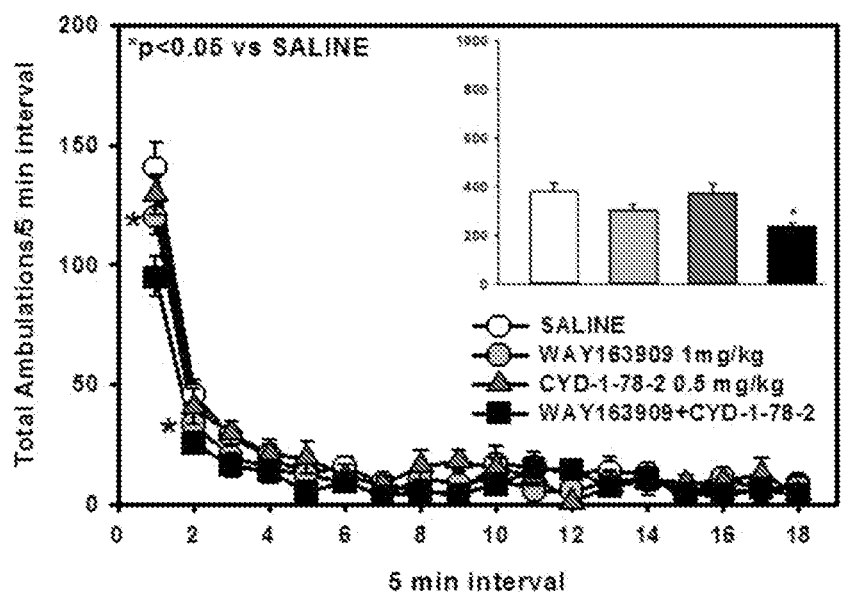

These analysis of motor activity (above) identify 0.5 mg/kg of CYD-1-78-2 or 0.5 mg/kg of CYD-1-79 as ineffective on spontaneous locomotor activity and supports the use of these low doses for analyses of allosteric effects in vivo. FIG. 8B illustrates the allosteric effects of CYD-1-78-2 (0.5 mg/kg) in combination with the selective 5-HT$_{2C}$R agonist WAY163909 (1 mg/kg) on spontaneous locomotor activity. A main effect of treatment [$F_{(3,450)}$=4.53, p<0.001], time [$F_{(17,450)}$=148.04, p<0.0001] and a treatment×time interaction [$F_{(51,643)}$=1.93, p<0.001] is observed for horizontal ambulation divided into eighteen 5-min intervals (FIG. 8B). A priori comparisons indicate that neither CYD-1-78-2 nor WAY163909 at the chosen dose alter horizontal ambulation versus saline at any 5-min interval (n.s.; FIG. 8B), as predicted by our previous observations (Cunningham et al., 2011, *Neuropharmacology* 61:513-523; Cunningham et al., 2012, *ACS Chem. Neurosci*, Accepted Aug. 11, 2012). The combination of CYD-1-78-2 plus WAY163909 significantly reduces horizontal ambulation versus saline at interval 1 and interval 2 (p<0.05; FIG. 8B). A main effect of treatment is observed for horizontal ambulation totaled across the 90-min test session [$F_{(3,49)}$=4.53, p<0.01; FIG. 8B, inset]; a priori comparisons reveal that, while neither ligands tested alone at chosen doses alter total horizontal ambulation, the combination of CYD-1-78-2 plus WAY163909 significantly reduces total horizontal ambulation versus saline (p<0.05; FIG. 8B, inset). FIG. 9B illustrates the allosteric effects of CYD-1-79 (0.5 mg/kg) in combination with the selective 5-HT$_{2C}$R agonist WAY163909 (1 mg/kg) on spontaneous locomotor activity. A main effect of treatment [$F_{(3,648)}$=3.12, p<0.05], time [$F_{(17,648)}$=152.15, p<0.0001] but no treatment×time interaction [$F_{(51,648)}$=1.27, n.s.] is observed for horizontal ambulation divided into eighteen 5-min intervals (FIG. 9B). A priori comparisons indicated that neither CYD-1-79 nor WAY163909 at the chosen dose alters horizontal ambulation versus saline at any 5-min interval (n.s.; FIG. 9B). The combination of CYD-1-79 plus WAY163909 significantly reduces horizontal ambulation versus saline at interval 2 (p<0.05 FIG. 9B). A main effect of treatment is observed for horizontal ambulation totaled across the 90-min test session [$F_{(3,36)}$=3.70, p<0.05; FIG. 9, inset]; a priori comparisons revealed that, while neither ligand tested alone at chosen doses alters total horizontal ambulation, the combination of CYD-1-79 plus WAY163909 significantly reduces total horizontal ambulation versus saline (p<0.05; FIG. 9B, inset). Taken all together, these data demonstrate that both CYD-1-78-2 and CYD-1-79 augment selective 5-HT$_{2C}$R agonist-mediated suppression of spontaneous locomotor activity.

B. Materials and Methods

4-Chloropicolinic acid methyl ester (CYD-1-1)

A mixture of picolinic acid (10.0 g, 81.0 mmol, 1 equiv.) and sodium bromide (16.7 g, 162.0 mmol, 2 equiv.) in thionyl chloride (41 mL) was refluxed for 5 h at 80° C. After that, the solvent was removed under the vacuum at 85° C. to afford the brown residue. 80 mL of anhydrous methanol was slowly added into the residue and the mixture was stirred at room temperature for half an hour. The solvent was evaporated, and the residue was taken up in the saturated sodium bicarbonate and extracted with ethyl acetate (three times). The organic layers were combined, washed with saturated brine, dried over anhydrous Na$_2$SO$_4$ and evaporated. The residue was purified by silica gel column; eluting with 33% EtOAc in hexane afforded 4-chloropicolinic acid methyl ester (CYD-1-1) (8.0 g, 64%) as a brown solid; silica gel TLC R$_f$=0.15 (1:3 EtOAc/hexane); mp 55-56° C.; $^1$H NMR (600 MHz, CDCl$_3$) δ 8.67 (d, 1H, J=4.8 Hz), 8.16 (d, 1H, J=1.8 Hz), 7.51 (m, 1H), 4.04 (s, 3H).

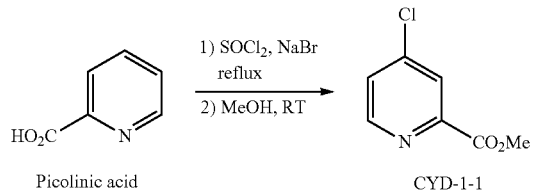 [SMILES: O=C(O)c1ccccn1 ; COC(=O)c1cc(Cl)ccn1]

4-Iodopicolinic acid methyl ester (CYD-1-4)

A mixture of 4-chloropicolinic acid methyl ester CYD-1-1 (4.8 g, 27.9 mmol), 57% hydriodic acid (26.6 mL, 232.2 mmol) and 50% aqueous hypophosphorous acid (1.32 mL, 12.0 mmol) was stirred at 85° C. for 2 h and then was stirred at 107° C. overnight. The mixture was cooled to 95° C. At this temperature 8.4 mL of 10 N sodium hydroxide aqueous solution was added into the reaction mixture slowly. The mixture was cooled to room temperature and stirred for 1 h, and the yellow solid was precipitated. The precipitate was filtered, washed with cold water and dried under the vacuum overnight to give 4-iodopicolinic acid as a yellow solid (6.8 g, 89%). To a solution of 4-iodopicolinic acid (6.73 g, 27.0 mmol) in methanol (101 mL) was added concentrated sulfuric acid (508 µL), and the mixture was refluxed at 80° C. for two days. The solvent was evaporated and the residue was taken up with the saturated sodium bicarbonate and extracted with ethyl acetate (three times). The organic layers were combined, washed with saturated brine, dried over anhydrous Na$_2$SO$_4$ and evaporated. The residue was purified with silica gel column; eluting with 1:3 ethyl acetate-hexane provided 4-iodopicolinic acid methyl ester (CYD-1-4) as a yellow solid (2.88 g, 40% for two steps); mp 73-74° C.; $^1$H NMR (600 MHz, CDCl$_3$) δ 8.50 (d, 1H, J=1.2 Hz), 8.39 (d, 1H, J=5.4 Hz), 7.87 (dd, 1H, J=1.8 Hz and 4.8 Hz), 4.02 (s, 3H).

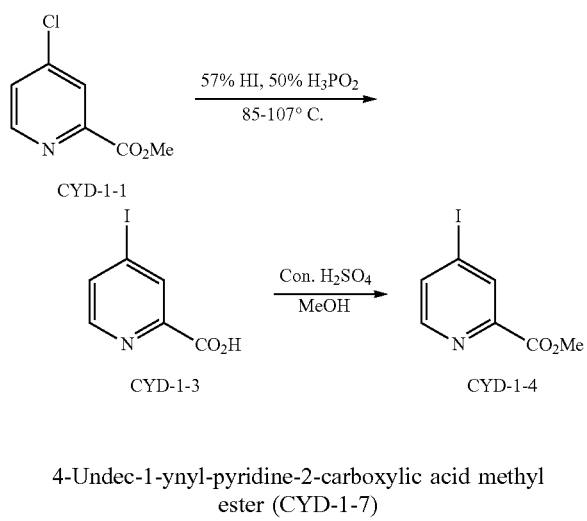

4-Undec-1-ynyl-pyridine-2-carboxylic acid methyl ester (CYD-1-7)

To a dried flask was added CYD-1-4 (2.77 g, 10.55 mmol, 1 equiv.), triphenylphosphine (0.276 g, 1.05 mmol, 0.1 equiv.), copper (I) iodide (0.2 g, 1.05 mmol, 0.1 equiv.), palladium acetate (0.118 g, 0.53 mmol, 0.05 equiv.) and triethylamine (37 mL). The mixture was degassed with nitrogen, followed by addition of 1-undecyne (4.16 mL, 21.1 mmol, 2.0 equiv.). The reaction mixture was stirred at room temperature for 12 h. The insoluble solid was filtered and the filtrate was concentrated under the vacuum, and the dark residue was purified with silica gel chromatography; eluting with 1:3 ethyl acetate-hexane provided the desired product CYD-1-7 as a brown oil (2.85 g, 94%); $^1$H NMR (600 MHz, CDCl$_3$): δ 8.65 (d, 1H, J=4.8 Hz), 8.08 (s, 1H), 7.41 (d, 1H, J=4.2 Hz), 4.00 (s, 3H), 2.44 (t, 2H, J=7.2 Hz), 1.62 (m, 2H), 1.44 (m, 2H), 1.29 (m, 10H), 0.88 (t, 3H, J=7.2 Hz). $^{13}$C NMR (150 MHz, CDCl$_3$): δ 165.4, 149.6, 147.9, 133.8, 128.7, 127.3, 97.7, 77.8, 52.9, 31.8, 29.4, 29.2, 29.1, 28.9, 28.3, 22.7, 19.5, 14.1.

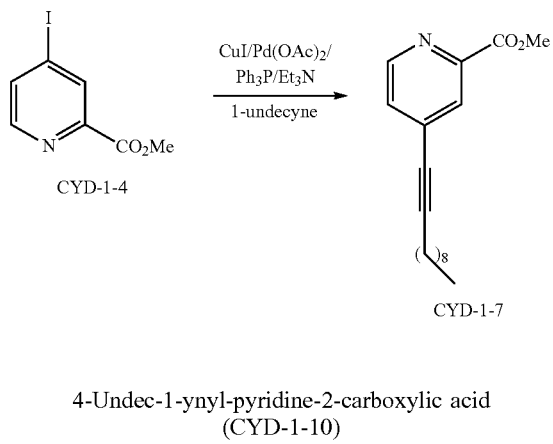

4-Undec-1-ynyl-pyridine-2-carboxylic acid (CYD-1-10)

To a solution of CYD-1-7 (2.5 g, 8.7 mmol, 1 equiv.) in THF (12 mL) and H$_2$O (3 mL) was added lithium hydroxide monohydrate (313 mg, 13.6 mmol, 1.5 equiv.). The reaction mixture was stirred at room temperature overnight, and TLC indicated that the reaction was incomplete. Another portion of lithium monohydrate (627 mg, 27.2 mmol, 3 equiv.) was added into the reaction mixture. The reaction was stirred for another 8 h, and TLC showed the starting material disappeared. The solvent was removed under the vacuum, and the solid appeared. The residue was taken up with 5% HCl (10 mL), and extracted with EtOAc (three times). The organic layers were combined, washed by brine and dried over anhydrous Na$_2$SO$_4$. The solvent was evaporated to afford the desired product CYD-1-10 (2.3 g, 96%) as a white solid; mp 93-94° C. $^1$H NMR (600 MHz, CDCl$_3$): δ 10.05 (br s, 1H), 8.62 (br s, 1H), 8.25 (br s, 1H), 7.56 (m, 1H), 2.44 (t, 2H, J=7.2 Hz), 1.63 (m, 2H), 1.45 (m, 2H), 1.30 (m, 10H), 0.88 (t, 3H, J=7.2 Hz).

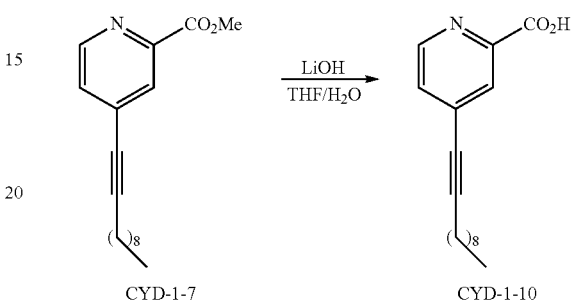

4-Undec-1-ynyl-pyridine-2-carboxylic acid (2-hydroxyethyl)amide (CYD-1-44)

A solution of CYD-1-10 (100 mg, 0.36 mmol) and triethylamine (110 mg, 1.09 mmol) dissolved in 10 mL of dichloromethane was cooled to 10° C., and isobutylchloroformate (60 mg, 0.44 mmol) was added in one portion. The mixture was stirred at 10° C. for one hour. Ethanolamine (28.9 mg, 0.47 mmol) was added into the reaction mixture, and the reaction mixture was stirred at room temperature for 2 hrs. TLC indicated that the starting material was gone. The solvents were removed under vacuum to give an oil residue. The residue was purified by silica gel column; eluting with 50% EtOAc in hexane afforded CYD-1-44 (112.0 mg, 96%) as a colorless solid; silica gel TLC R$_f$=0.15 (1:3 EtOAc/hexane); $^1$H NMR (600 MHz, CDCl$_3$) δ 8.45 (d, 1H, J=4.8 Hz), 8.37 (br s, 1H), 7.36 (m, 1H), 3.85 (dd, 2H, J=5.4 Hz, 9.6 Hz), 3.65 (dd, 2H, J=6.0 Hz, 10.8 Hz), 2.43 (t, 2H, J=7.2 Hz), 1.61 (m, 3H), 1.43 (m, 2H), 1.29 (m, 10H), 0.88 (m, 3H).

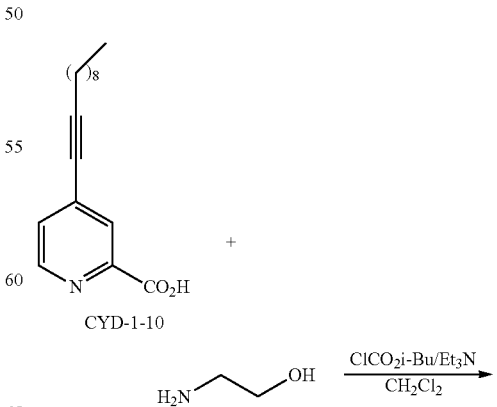

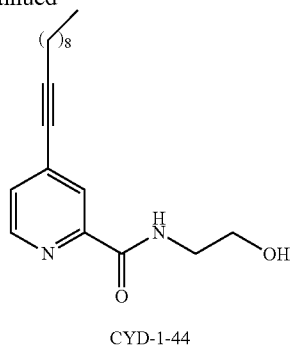

CYD-1-44

2,4-cis-N-(2-hydroxyethyl)-4-undecylpiperidine-2-carboxamide (CYD-1-45)

A solution of CYD-1-44 (100 mg, 0.31 mmol), 75 μL of 37% HCl and PtO$_2$ catalyst (206 mg, 0.91 mmol) in 6 mL of methanol and 4 mL of H$_2$O was reduced on a Parr hydrogenator at 60 p.s.i. for 2 days. TLC indicated that the starting material was gone. The platinum solid was filtered and the filtrate was concentrated on vacuum to give an oil residue. The residue was purified by silica gel column; eluting with 10% MeOH in CH$_2$Cl$_2$ afforded CYD-1-45 (66.0 mg, 64%) as a colorless solid; $^1$H NMR (600 MHz, CDCl$_3$) δ 7.54 (d, 1H, J=4.8 Hz), 4.11 (br s, 2H), 3.71 (s, 2H), 3.46 (d, 2H, J=10.2 Hz), 3.32 (m, 1H), 3.24 (d, 1H, J=12.0 Hz), 2.78 (t, 1H, J=11.4 Hz), 2.09 (d, 1H, J=12.6 Hz), 1.73 (d, 1H, J=13.2 Hz), 1.48 (br s, 1H), 1.25 (m, 22H), 0.88 (t, 3H, J=7.2 Hz).

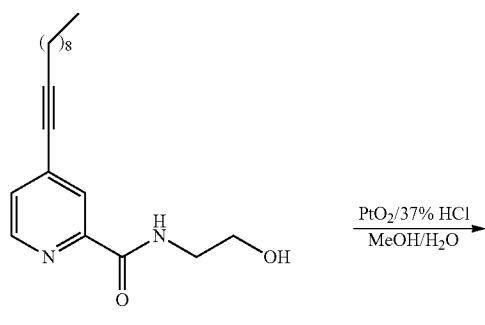

CYD-1-44

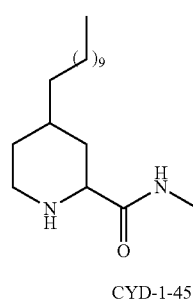

CYD-1-45

N-(3-morpholinopropyl)-4-(undec-1-ynyl)picolinamide (CYD-1-42)

To a solution of CYD-1-10 (100 mg, 0.36 mmol), triethylamine (147 mg, 1.46 mmol) and 3-morpholinopropan-1-amine (68.5 mg, 0.47 mmol) in 10 mL of CH$_2$Cl$_2$ was added HBTU (276 mg, 0.73 mmol) in an ice-water bath. The reaction mixture was stirred at room temperature for 18 hrs. TLC indicated that the starting material was gone, and a less polar product was produced. The reaction mixture was diluted with CH$_2$Cl$_2$, washed with water and brine, and dried with anhydrous Na$_2$SO$_4$. The solvent was removed under vacuum to give an oil residue. The residue was purified by silica gel column; eluting with 2% Et$_3$N in EtOAc afforded CYD-1-42 (125.0 mg, 85%) as a colorless oil; $^1$H NMR (600 MHz, CDCl$_3$) δ 8.94 (s, 1H), 8.46 (d, 1H, J=4.8 Hz), 8.14 (s, 1H), 7.35 (m, 1H), 3.79 (m, 4H), 3.57 (m, 2H), 2.48 (m, 8H), 1.80 (m, 2H), 1.61 (m, 2H), 1.44 (t, 2H, J=7.2 Hz), 1.29 (m, 10H), 0.88 (t, 3H, J=7.2 Hz).

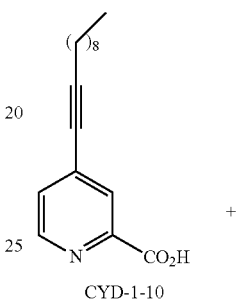

CYD-1-10

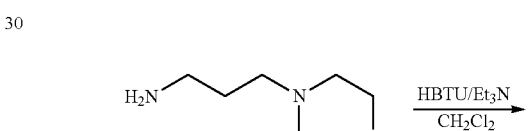

CYD-1-42

2,4-cis-N-(3-morpholinopropyl)-4-undecylpiperidine-2-carboxamide (CYD-1-46)

A solution of CYD-1-42 (100 mg, 0.25 mmol), 150 μL of 37% HCl and PtO$_2$ catalyst (169 mg, 0.744 mmol) in 6 mL of methanol and 4 mL of H$_2$O was reduced on a Parr hydrogenator at 60 p.s.i. for 1 d. TLC indicated that the starting material was gone. The platinum solid was filtered through the celite and the filtrate was concentrated under vacuum to give the HCl salt of CYD-1-46 as colorless gel (108 mg, 90%); $^1$H NMR (600 MHz, CD$_3$OD) δ 4.0 (d, 2H, J=12.6 Hz), 3.79 (m, 3H), 3.48 (d, 2H, J=10.8 Hz), 3.37 (m, 2H), 3.22 (m, 5H), 2.98 (m, 1H), 2.21 (d, 1H, J=13.2 Hz), 1.94 (m, 3H), 1.66 (br s, 1H), 1.25 (m, 22H), 0.84 (t, 3H, J=7.2 Hz).

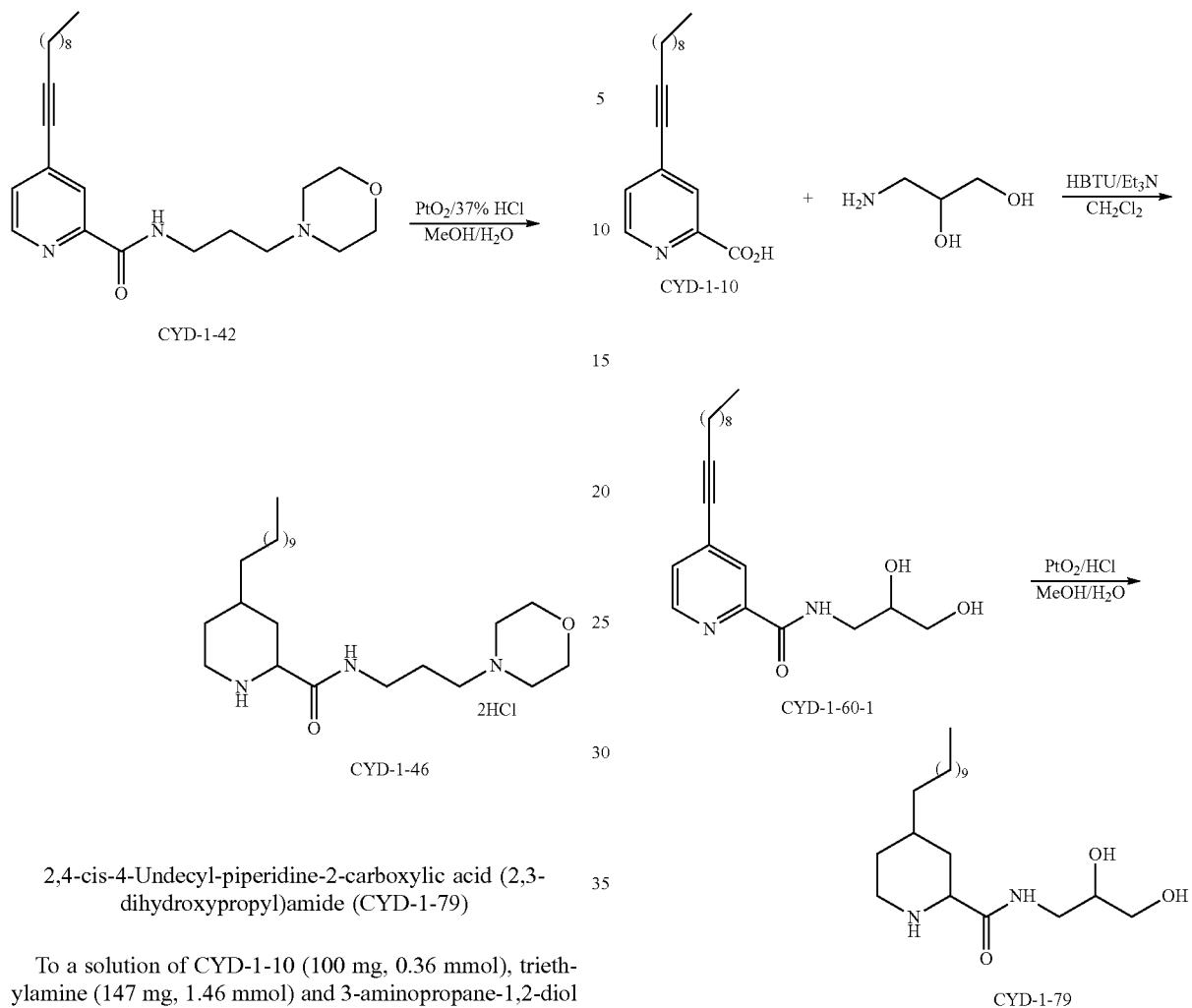

2,4-cis-4-Undecyl-piperidine-2-carboxylic acid (2,3-dihydroxypropyl)amide (CYD-1-79)

To a solution of CYD-1-10 (100 mg, 0.36 mmol), triethylamine (147 mg, 1.46 mmol) and 3-aminopropane-1,2-diol (42.8 mg, 0.47 mmol) in 10 mL of CH$_2$Cl$_2$ was added HBTU (276 mg, 0.73 mmol) in an ice-water bath. The reaction mixture was stirred at room temperature for 18 hrs. TLC indicated that the starting material was gone, and a less polar product was produced. The reaction mixture was diluted with CH$_2$Cl$_2$, washed with water and brine, and dried with anhydrous Na$_2$SO$_4$. The solvent was removed under vacuum to give an oil residue. The residue was purified by silica gel column; eluting with 2% Et$_3$N in EtOAc afforded CYD-1-60-1 (125.0 mg, 85%) as a colorless oil. A solution of CYD-1-60-1 (50 mg, 0.14 mmol), 36 µL of 37% HCl and PtO$_2$ catalyst (79 mg, 0.43 mmol) in 6 mL of methanol and 4 mL of H$_2$O was reduced on a Parr hydrogenator at 60 p.s.i. for 2 days. TLC indicated that the starting material was gone. The platinum solid was filtered and the filtrate was concentrated on vacuum to give an oil residue. The residue was partitioned between CH$_2$Cl$_2$ (30 ml) and saturated aqueous NaHCO$_3$ (10 mL), dried over anhydrous Na$_2$SO$_4$, filtered and concentrated to give an oil residue. The residue was purified by silica gel column; eluting with 17% MeOH in CH$_2$Cl$_2$ afforded CYD-1-79 (28.0 mg, 54%) as a colorless solid; $^1$H NMR (800 MHz, CDCl$_3$) δ 7.44 (d, 1H, J=24.8 Hz), 3.76 (br s, 4H), 3.56 (m, 1H), 3.51 (d, 1H, J=11.2 Hz), 3.44 (m, 1H), 3.36 (s, 1H), 3.27 (d, 1H, J=11.4 Hz), 3.14 (d, 1H, J=12.0 Hz), 2.65 (t, 1H, J=12.0 Hz), 2.03 (s, 1H), 1.69 (d, 1H, J=12.0 Hz), 1.42 (s, 1H), 1.25 (s, 20H), 1.01 (m, 2H), 0.88 (t, 3H, J=7.2 Hz).

2,4-cis-(4-Undecyl-piperidin-2-yl)-methanol (CYD-1-57)

To a solution of CYD-1-7 (1.0 g, 3.5 mmol) in a mixture of MeOH (12 mL), water (12 mL) and acetic acid (0.218 mL, 3.5 mmol) was added platinum oxide (318.0 mg, 1.4 mmol). The reaction mixture was purged and charged with hydrogen, and reduced on a Parr hydrogenator at 60 p.s.i. for 2 days. The platinum oxide was removed by filtration and the filtrate was concentrated to give an oil residue. The residue was dissolved in methanol and basified with the saturated NaHCO$_3$ aqueous solution. The resulting solution was concentrated again under vacuum to give a white solid residue. The residue was purified with silica gel column, eluting with 1:10 methanol-dichloromethane gave the title product CYD-1-57 (843.8 mg, 90%) as colorless gel. $^1$H NMR (600 MHz, CDCl$_3$): δ 3.59 (d, 1H, J=7.8 Hz), 3.39 (t, 1H, J=8.4 Hz), 3.11 (m, 3H), 2.64 (m, 2H), 1.69 (d, 1H, J=10.8 Hz), 1.61 (d, 1H, J=12.0 Hz), 1.37 (m, 1H), 1.26 (s, 20H), 1.05 (m, 1H), 0.89 (t, 3H, J=6.6 Hz), 0.78 (m, 1H). $^{13}$C NMR (150 MHz, CDCl$_3$): δ 66.5, 58.1, 46.3, 37.3, 36.0, 35.4, 33.2, 32.0, 30.0, 29.9, 29.8, 29.7, 29.5, 27.8, 26.6, 22.8, 14.2.

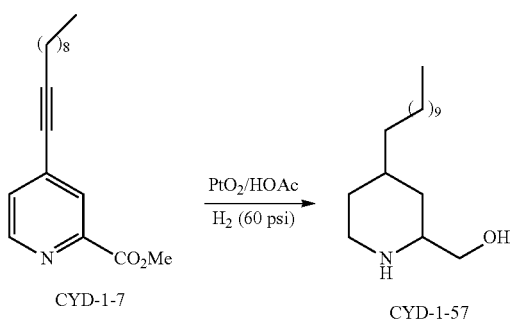

2,4-cis-Methyl 4-undecylpiperidine-2-carboxylate (CYD-1-62)

To a solution of CYD-1-7 (500 mg, 1.74 mmol) in a mixture of MeOH (9 mL), water (6 mL) and hydrochloric acid (0.144 mL, 1.74 mmol) was added platinum oxide (158.0 mg, 0.69 mmol). The reaction mixture was purged and charged with hydrogen (60 psi) for 24 hrs. The platinum oxide was removed by filtration and the filtrate was concentrated to give an oil residue. The residue was diluted with $CH_2Cl_2$ and washed with the saturated $NaHCO_3$ aqueous solution. After drying with anhydrous $Na_2SO_4$, the solvent was removed under vacuum to give a colorless oil residue. The residue was purified with silica gel column; eluting with 1:20 methanol-dichloromethane gave the desired product CYD-1-62 (500 mg, 97%) as a colorless gel. $^1H$ NMR (600 MHz, $CDCl_3$): δ 3.72 (s, 3H), 3.32 (dd, 1H, J=11.4 Hz and 1.8 Hz), 3.15 (d, 1H, J=11.4 Hz), 2.61 (dt, 1H, J=12.0 Hz and 1.8 Hz), 2.04 (d, 1H, J=12.6 Hz), 1.65 (d, 1H, J=13.2 Hz), 1.29 (br s, 1H), 1.26 (s, 20H), 1.03 (q, 2H, J=12.0 Hz), 0.88 (t, 3H, J=7.2 Hz). $^{13}C$ NMR (150 MHz, $CDCl_3$): δ 173.8, 59.0, 51.7, 45.8, 36.9, 36.1 (2C), 32.7, 31.8, 29.7, 29.5 (4C), 29.2, 26.3, 22.6, 14.0.

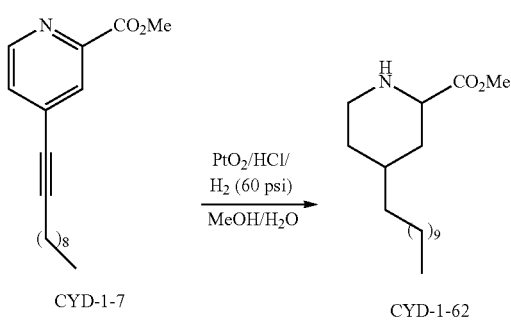

2,4-cis-1-(tert-Butoxycarbonyl)-4-undecylpiperidine-2-carboxylic acid (CYD-1-66)

To a solution of CYD-1-62 (900 mg, 3.02 mmol) in methanol (10 mL) was added $Et_3N$ (0.87 mL, 6.06 mmol) and $(Boc)_2O$ (850 mg, 3.94 mmol). The mixture was stirred at room temperature overnight. The solvent was removed under vacuum to give an oil residue. The residue was purified with silica gel column; eluting with 6:1 hexane-ethyl acetate gave the Boc-protection product CYD-1-63 (1.08 g, 90%) as colorless oil. To a mixture of CYD-1-63 (1.08 g, 2.72 mmol) in 12 mL of THF and 4 mL of water was added lithium hydroxide monohydrate (514 mg, 12.24 mmol). The mixture was stirred at room temperature for 48 hrs. THF was removed under vacuum. The aqueous layer was taken up in ethyl acetate, partitioned with 10% $NaHSO_4$ aqueous solution. The organic layer was washed with water and brine, and then dried with anhydrous $Na_2SO_4$ and concentrated under vacuum to give the desired product CYD-1-66 (1.04 g, 99%) as colorless oil. $^1H$ NMR (800 MHz, $CDCl_3$): δ 4.27 (s, 1H), 3.51 (br s, 1H), 3.40 (s, 1H), 2.01 (m, 1H), 1.75 (s, 2H), 1.59 (s, 1H), 1.36 (s, 9H), 1.35 (m, 1H), 1.28 (s, 20H), 0.88 (t, 3H, J=7.2 Hz). $^{13}C$ NMR (150 MHz, $CDCl_3$): δ 177.1, 175.1, 80.5, 34.0, 31.8 (2C), 31.4 (2C), 29.6 (3C), 29.5 (3C), 29.3, 29.1, 28.2 (3C), 27.0, 22.6, 14.0. MS (−ESI): m/z (%)=382.2231 (100%) $[M-H]^-$.

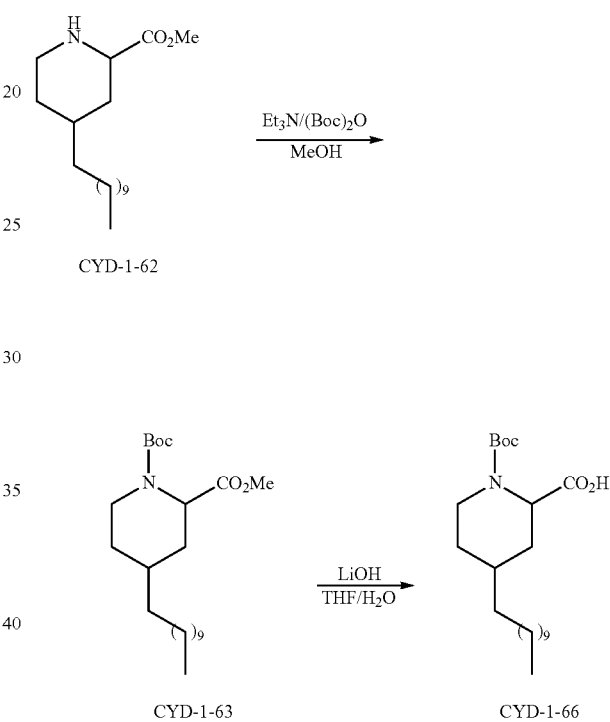

Methyl α-thiolincosaminide (7-OH-MTL) (CYD-1-6)

A solution of lincomycin hydrochloride (4.46 g, 10 mmol) in 40 mL of hydrazine hydrate was refluxed at 120° C. for 24 h. The excess hydrazine was then distilled off under vacuum at 120° C. to afford a white semisolid mush. The residue was stirred with 40 mL of acetonitrile until all of the lumps had broken up. The solid was collected by filtration and washed with acetonitrile and then ether. After being dried under the vacuum, the crude product (2.1 g, 83%) was recrystallized from 18 mL of DMF to afford the desired compound CYD-1-6 as a white crystal (1.5 g, 59%); mp 217-218° C. (decomposition); $[\alpha]_D^{23.2}$=+223.3; $^1H$ NMR (600 MHz, $D_2O$) δ 5.24 (d, 1H, J=6.0 Hz), 4.02 (m, 3H), 3.88 (d, 1H, J=9.6 Hz), 3.57 (dd, 1H, J=3.0 Hz and 10.2 Hz), 3.08 (dd, 1H, J=3.6 Hz and 9.6 Hz), 2.04 (s, 3H), 1.06 (d, 3H, J=6.6 Hz).

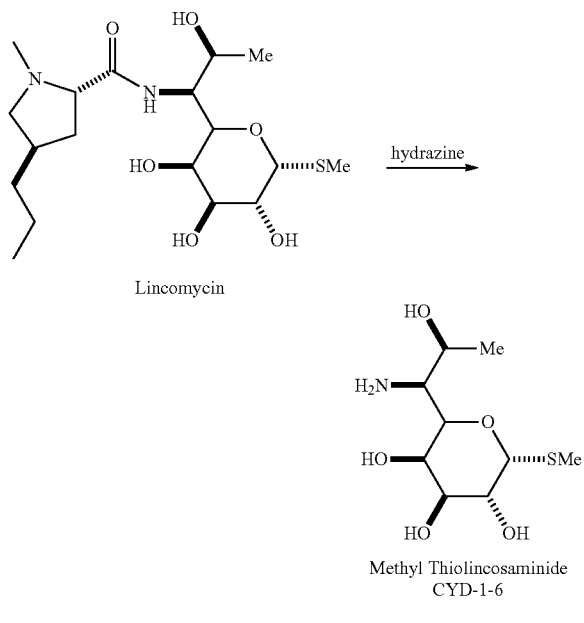

Lincomycin

Methyl Thiolincosaminide
CYD-1-6

2,4-cis-4-Undecyl-piperidine-2-carboxylic acid [2-hydroxy-1-(3,4,5-trihydroxy-6-methylsulfanyl-tetrahydro-pyran-2-yl)-propyl]-amide (CYD-3-27)

To a solution of CYD-1-66 (150 mg, 0.39 mmol) and 7-OH-MTL (CYD-1-6) (99 mg, 0.39 mmol) in 6 mL of DMF was added HBTU (192 mg, 0.51 mmol) and DIPEA (126 mg, 0.97 mmol). The resulting mixture was stirred at room temperature for 16 hrs. After that, TLC showed that the starting material disappeared. The solvent DMF was removed under vacuum to give a dark oil residue. The oil residue was partitioned between $CH_2Cl_2$ (50 ml) and 10% citric aqueous solution (10 mL). The organic layer was separated and washed with saturated aqueous $NaHCO_3$ (10 mL). After drying with anhydrous $Na_2SO_4$, the solvent was removed under vacuum to give an oil residue. This residue was purified with silica gel column; eluting with 10% MeOH in $CH_2Cl_2$ afforded the amide CYD-3-26 (200 mg, 82%). The amide CYD-3-26 (200 mg, 0.32 mmol) was dissolved in $CH_2Cl_2$ (1 mL), and then TFA (250 µL) was added into it. The resulting mixture was stirred at room temperature. After 2 hrs, TLC showed the starting material disappeared. The solvent was removed under vacuum to give an oil residue. The residue was partitioned between $CH_2Cl_2$ (30 mL) and saturated $NaHCO_3$ aqueous solution (10 mL). The organic layer was dried over anhydrous $Na_2SO_4$, filtered and concentrated to give an oil residue. This residue was purified with silica gel column; eluting with 15% MeOH in $CH_2Cl_2$ afforded CYD-3-27 (120 mg, 71%) as a colorless gel. $^1H$ NMR (600 MHz, $CDCl_3$+$CD_3OD$) δ 5.30 (d, 1H, J=5.4 Hz), 4.21 (m, 1H), 4.12 (m, 3H), 4.05 (d, 1H, J=9.6 Hz), 3.88 (dd, 1H, J=3.0 Hz and 10.2 Hz), 3.58 (dd, 1H, J=3.0 Hz and 10.2 Hz), 3.26 (m, 8H), 2.65 (m, 1H), 2.13 (s, 3H), 2.02 (d, 1H, J=11.4 Hz), 1.71 (m, 1H), 1.43 (m, 1H), 1.25 (m, 23H), 1.04 (m, 2H), 0.88 (t, 3H, J=7.2 Hz). $^{13}C$ NMR (150 MHz, $CDCl_3$+$CD_3OD$) δ 175.2, 175.1, 88.5, 88.4, 70.7, 70.6, 70.2, 69.9, 68.7, 68.5, 68.1, 68.0, 66.7, 66.5, 60.2, 59.8, 53.8, 53.2, 49.4, 49.2, 49.0, 48.8, 45.3, 44.9, 36.8, 36.7, 36.3, 36.2, 35.6, 35.4, 31.8 (2C), 31.7 (2C), 31.4, 29.7, 29.5 (2C), 29.4 (3C), 29.2 (3C), 26.3 (2C), 22.5 (2C), 17.4, 16.8, 13.9, 13.6 (2C).

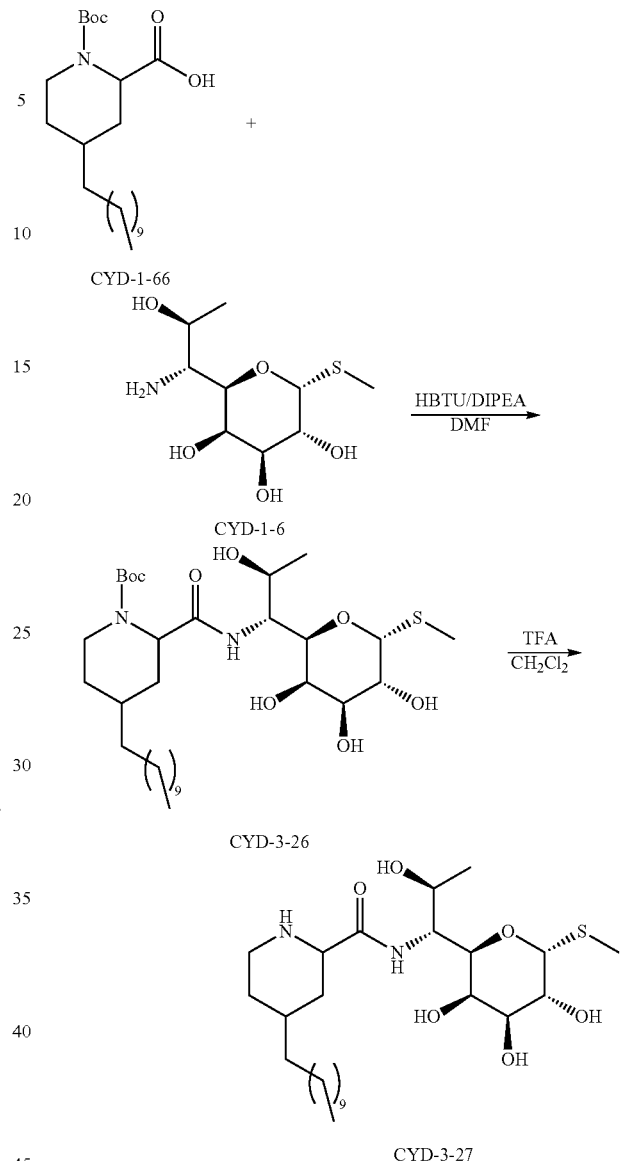

2,4-cis-4-Undecyl-piperidine-2-carboxylic acid (3-chloro-2-hydroxy-propyl)-amide (CYD-3-31)

To a solution of CYD-1-66 (200 mg, 0.52 mmol) and (S)-1-amino-3-chloro-propanol (76 mg, 0.52 mmol) in 6 mL of DMF was added HBTU (256 mg, 0.67 mmol) and DIPEA (235 mg, 1.82 mmol). The resulting mixture was stirred at room temperature for 16 hrs. After that, TLC showed that the starting material disappeared. The solvent DMF was removed under vacuum to give a dark oil residue. The oil residue was partitioned between $CH_2Cl_2$ (50 ml) and 10% citric aqueous solution (10 mL). The organic layer was separated and washed with saturated aqueous $NaHCO_3$ (10 mL). After drying over anhydrous $Na_2SO_4$, the solvent was removed under vacuum to give an oil residue. This residue was purified with silica gel column; eluting with 10% MeOH in $CH_2Cl_2$ afforded the amide CYD-3-15 (200 mg, 80%). The amide CYD-3-15 (80 mg, 0.17 mmol) was dissolved in $CH_2Cl_2$ (1 mL), followed by the addition of TFA (250 μL). The resulting mixture was stirred at room temperature. After 2 hrs, TLC showed the starting material disappeared. The solvent was removed under vacuum to give an oil residue, which was then partitioned between CH$_2$Cl$_2$ (30 mL) and saturated NaHCO$_3$ aqueous solution (10 mL). The organic layer was dried over anhydrous Na$_2$SO$_4$, filtered and concentrated to give an oil residue. This residue was purified with silica gel column; eluting with 15% MeOH in CH$_2$Cl$_2$ afforded CYD-3-31 (35 mg, 55%) as a colorless gel. $^1$H NMR (600 MHz, CDCl$_3$+CD$_3$OD) δ 7.43 (br s, 1H), 3.88 (s, 1H), 3.65 (m, 3H), 3.23 (m, 3H), 2.62 (m, 1H), 1.97 (m, 1H), 1.69 (d, 1H, J=10.2 Hz), 1.41 (m, 1H), 1.23 (m, 20H), 1.02 (m, 2H), 0.85 (t, 3H, J=7.2 Hz). $^{13}$C NMR (150 MHz, CDCl$_3$+CD$_3$OD) δ 174.8, 70.2, 69.8, 60.0, 46.4, 45.2, 42.7, 36.8, 36.3, 35.5, 31.9, 31.8, 29.6, 29.5 (2C), 29.4, 29.2, 26.2, 22.5, 13.9.

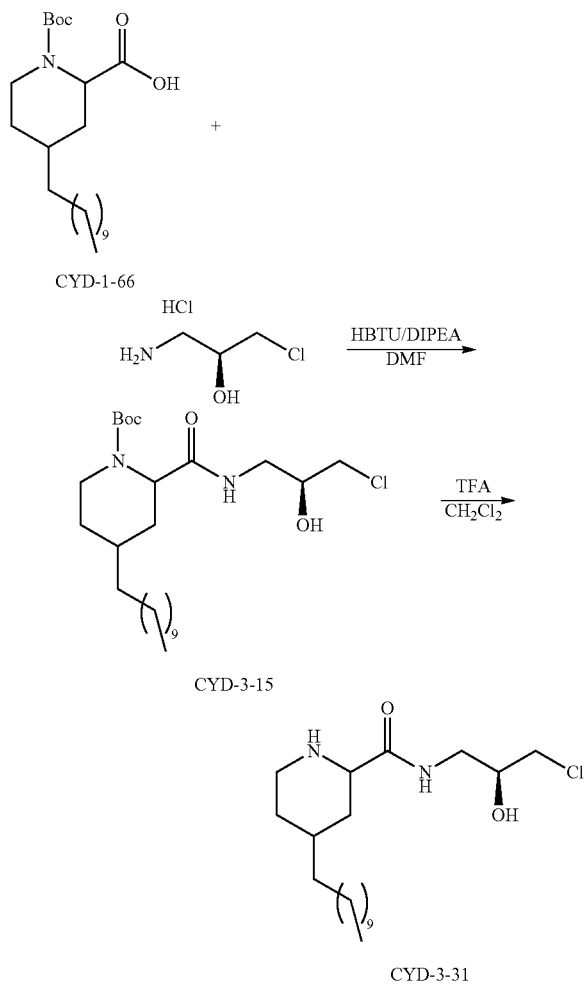

2,4-cis-4-Undecyl-piperidine-2-carboxylic acid (2-hydroxy-1-hydroxymethyl-ethyl)amide (CYD-3-30)

To a solution of CYD-1-66 (50 mg, 0.13 mmol) and 2-aminopropane-1,3-diol (12 mg, 0.13 mmol) in 4 mL of DMF was added HBTU (64 mg, 0.16 mmol) and DIPEA (59 mg, 0.45 mmol). The resulting mixture was stirred at room temperature for 16 hrs. After that, TLC showed that the starting material disappeared. The solvent DMF was removed under vacuum to give a dark oil residue, which was then partitioned between CH$_2$Cl$_2$ (50 ml) and 10% citric aqueous solution (10 mL). The organic layer was separated and washed with saturated aqueous NaHCO$_3$ (10 mL). After drying over anhydrous Na$_2$SO$_4$, the solvent was removed under vacuum to give an oil residue. This residue was purified with silica gel column; eluting with 10% MeOH in CH$_2$Cl$_2$ afforded the amide CYD-3-16 (60 mg, 98%). The amide CYD-3-16 (60 mg, 0.13 mmol) was dissolved in CH$_2$Cl$_2$ (1 mL), followed by the addition of TFA (250 μL). The resulting mixture was stirred at room temperature. After 2 hrs, TLC showed the starting material disappeared. The solvent was removed under vacuum to give an oil residue, which was then partitioned between CH$_2$Cl$_2$ (30 mL) and saturated NaHCO$_3$ aqueous solution (10 mL). The organic layer was dried over anhydrous Na$_2$SO$_4$, filtered and concentrated to give an oil residue. This residue was purified with silica gel column; eluting with 15% MeOH in CH$_2$Cl$_2$ afforded CYD-3-30 (35 mg, 74%) as colorless gel. $^1$H NMR (600 MHz, CDCl$_3$+CD$_3$OD) δ 3.89 (t, 1H, J=4.2 Hz), 3.66 (m, 4H), 3.15 (m, 1H), 2.62 (m, 1H), 1.99 (d, 1H, J=12.0 Hz), 1.71 (d, 1H, J=12.6 Hz), 1.43 (m, 1H), 1.26 (m, 20H), 1.02 (m, 2H), 0.88 (t, 3H, J=6.6 Hz). $^{13}$C NMR (150 MHz, CDCl$_3$+CD$_3$OD) δ 174.5, 60.9, 60.1, 52.1, 45.1, 36.7, 36.4, 35.6, 32.1, 31.5 (2C), 29.4, 29.3 (3C), 29.0 (2C), 26.0, 22.3, 13.5.

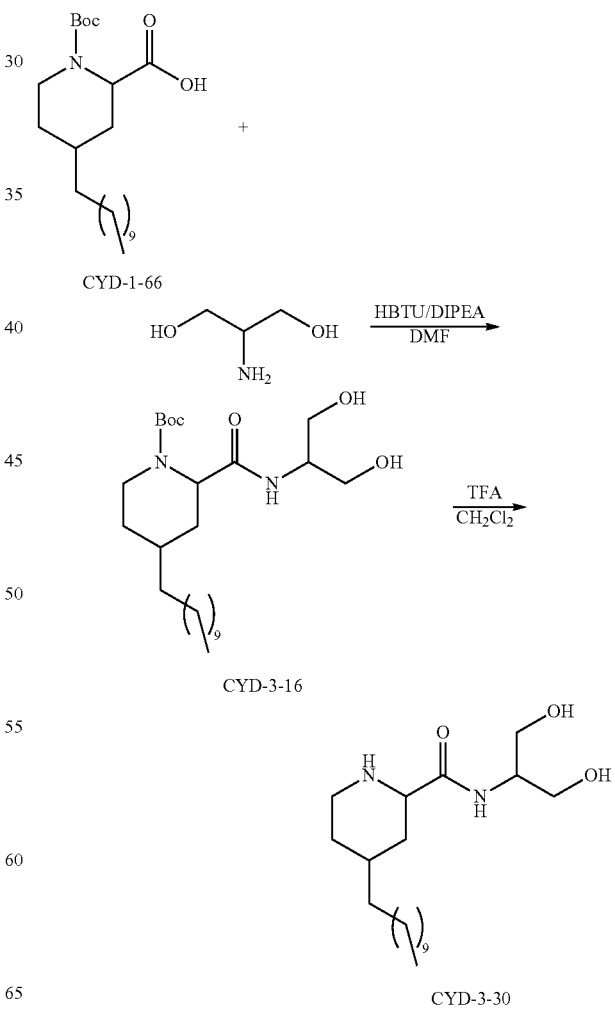

(2R,4S)—N-((1S,2S)-1,3-dihydroxy-1-phenylpropan-2-yl)-4-undecylpiperidine-2-carboxamide (CYD-3-47-1) and (2S,4R)—N-((1S,2S)-1,3-dihydroxy-1-phenylpropan-2-yl)-4-undecylpiperidine-2-carboxamide (CYD-3-47-2)

To a solution of CYD-1-66 (70 mg, 0.18 mmol) and (1S,2S)-2-amino-1-phenylpropane-1,3-diol (30 mg, 0.18 mmol) in 4 mL of DMF was added HBTU (89 mg, 0.23 mmol) and DIPEA (58 mg, 0.45 mmol). The resulting mixture was stirred at room temperature for 16 hrs. The solvent DMF was removed under vacuum to give a dark oil residue, which was then partitioned between $CH_2Cl_2$ (50 ml) and 10% citric aqueous solution (10 mL). The organic layer was separated and washed with saturated aqueous $NaHCO_3$ (10 mL). After drying over anhydrous $Na_2SO_4$, the solvent was removed under vacuum to give an oil residue. This residue was purified with silica gel column; eluting with 10% MeOH in $CH_2Cl_2$ afforded the amide CYD-3-42 (50 mg, 52%). The amide CYD-3-42 (50 mg, 0.13 mmol) was dissolved in $CH_2Cl_2$ (1 mL), followed by the addition of TFA (250 μL). The resulting mixture was stirred at room temperature. After 2 hr, TLC showed the starting material disappeared. The solvent was removed under vacuum to give an oil residue. The residue was partitioned between $CH_2Cl_2$ (30 mL) and saturated $NaHCO_3$ aqueous solution (10 mL). The organic layer was dried with anhydrous $Na_2SO_4$, filtered and concentrated to give an oil residue. This residue was purified with silica gel column; eluting with 15% MeOH in $CH_2Cl_2$ afforded CYD-3-47-1 (14 mg, 35%) and CYD-3-47-2 (15 mg, 37%) as a colorless gel, respectively.

CYD-3-47-1: $^1$H NMR (600 MHz, $CDCl_3$+$CD_3OD$) δ 7.37 (m, 2H), 7.32 (t, 2H, J=7.2 Hz), 7.24 (t, 1H, J=6.6 Hz), 4.98 (m, 1H), 4.03 (d, 1H, J=4.2 Hz), 3.69 (m, 1H), 3.62 (m, 1H), 3.10 (d, 2H, J=11.4 Hz), 2.60 (t, 1H, J=12.0 Hz), 1.78 (d, 1H, J=12.6 Hz), 1.67 (d, 1H, J=12.6 Hz), 1.33 (m, 1H), 1.26 (m, 20H), 1.18 (m, 1H), 1.01 (m, 1H), 0.88 (t, 3H, J=6.6 Hz), 0.75 (t, 1H, J=12.6 Hz). $^{13}$C NMR (150 MHz, $CDCl_3$+$CD_3OD$) δ 174.7, 141.2, 128.0 (2C), 127.3, 125.8 (2C), 72.3, 62.1, 60.2, 56.2, 45.2, 36.7, 36.1, 35.5, 31.9, 31.7, 29.6, 29.5 (2C), 29.4 (2C), 29.1, 26.1, 22.5, 13.8.

CYD-3-47-2: $^1$H NMR (600 MHz, $CDCl_3$) δ 7.41 (m, 1H), 7.38 (m, 1H), 7.31 (t, 2H, J=7.2 Hz), 7.25 (m, 1H), 5.06 (s, 1H), 4.08 (m, 1H), 3.80 (m, 4H), 3.22 (d, 1H, J=10.8), 3.03 (d, 1H, J=12.0 Hz), 2.54 (t, 1H, J=12.0 Hz), 1.77 (d, 1H, J=12.0 Hz), 1.61 (d, 1H, J=12.6 Hz), 1.27 (m, 20H), 1.13 (m, 2H), 0.95 (m, 1H), 0.88 (t, 3H, J=6.6 Hz), 0.81 (m, 1H). $^{13}$C NMR (150 MHz, $CDCl_3$) δ 173.6, 141.4, 128.2 (2C), 127.4, 125.8 (2C), 73.3, 63.2, 60.0, 56.4, 44.9, 36.7, 36.2, 35.2, 31.8, 31.6, 29.7, 29.6 (3C), 29.3 (2C), 26.2, 22.6, 14.0.

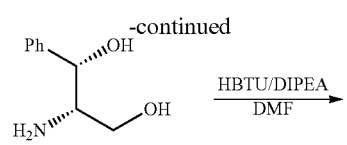

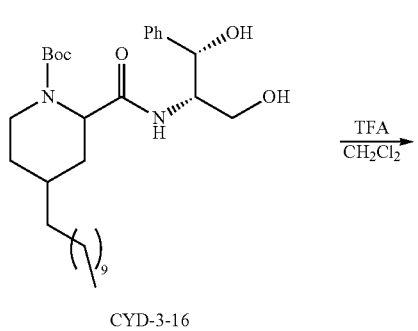

CYD-3-16

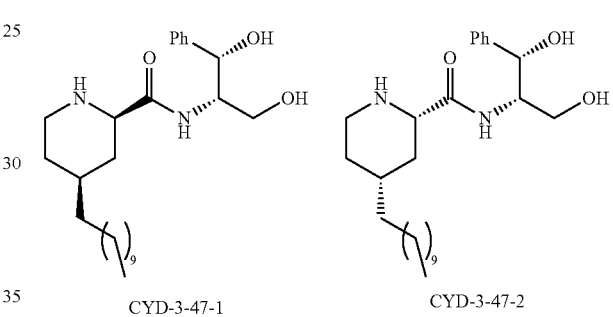

CYD-3-47-1        CYD-3-47-2

Methyl 6-amino-7(S)-chloro-6,7,8-trideoxy-1-thio-L-threo-α-D-galacto-octopyranoside (CYD-1-53)

A solution of methyl α-thiolincosaminide (CYD-1-6) (1.0 g, 3.95 mmol, 1 equiv), triphenylphosphine (3.0 g, 11.45 mmol, 3 equiv.), carbon tetrachloride (10 mL, 103.6 mmol, 25 equiv.) in 100 mL of acetonitrile was refluxed for 3 h. The solvent was removed under hood vacuum at 70° C. The residue was purified with silica gel column; elution with 3:1 chloroform-methanol produced CYD-1-53 (330 mg, 31%) as a yellow solid; mp 168-172° C. (decomposition); $^1$H NMR (600 MHz, $D_2O$) δ 5.20 (d, 1H, J=6.0 Hz), 3.98 (m, 3H), 3.92 (d, 1H, J=9.0 Hz), 3.53 (dd, 1H, J=2.4 Hz and 10.2 Hz), 3.10 (dd, 1H, J=3.6 Hz and 9.0 Hz), 1.99 (s, 3H), 1.04 (d, 3H, J=6.6 Hz).

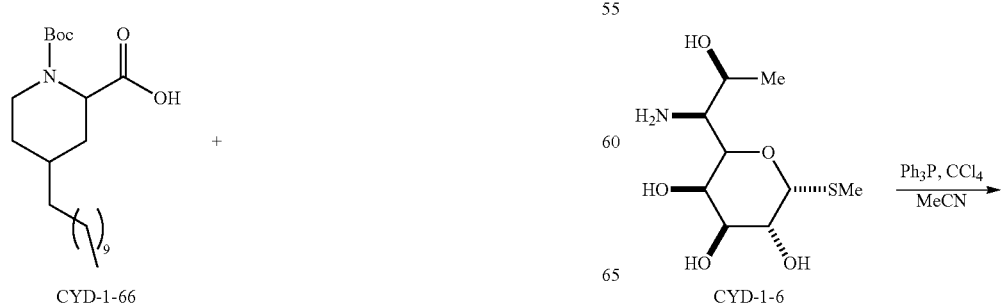

CYD-1-66        CYD-1-6

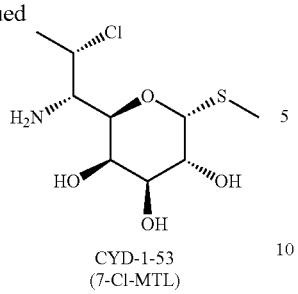

CYD-1-53
(7-Cl-MTL)

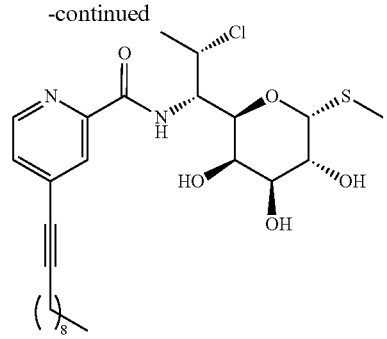

CYD-3-21

4-Undec-1-ynyl-pyridine-2-carboxylic acid [2-chloro-1-(3,4,5-trihydroxy-6-methylsulfanyl-tetrahydro-pyran-2-yl)-propyl]-amide (CYD-3-21)

A solution of CYD-1-10 (201 mg, 0.73 mmol) and triethylamine (186 mg, 1.84 mmol) dissolved in 10 ml of acetonitrile was cooled to 10° C., and isobutylchloroformate (100 mg, 0.73 mmol) was added in one portion. The mixture was stirred at 10° C. for 1 h. Another solution of 7-Cl-MTL (200 mg, 0.73 mmol) dissolved in 3 mL of acetone and 3 mL of H$_2$O was added into the reaction mixture, which was then allowed to stir at room temperature for 18 hrs. After that, the solvents were removed under vacuum to give an oil residue. The residue was purified by silica gel column; eluting with 10% MeOH in CH$_2$Cl$_2$ afforded the desired amide CYD-3-21 (110.0 mg, 45%) as a colorless solid; silica gel TLC R$_f$=0.20 (1:10 MeOH/CH$_2$Cl$_2$); $^1$H NMR (600 MHz, CDCl$_3$): δ 8.57 (d, 1H, J=9.0 Hz), 8.50 (d, 1H, J=4.8 Hz), 8.15 (s, 1H), 7.39 (d, 1H, J=4.2 Hz), 5.45 (d, 1H, J=4.2 Hz), 5.00 (m, 1H), 4.57 (m, 1H), 4.49 (m, 1H), 4.23 (m, 1H), 4.19 (s, 1H), 3.89 (d, 1H, J=8.4 Hz), 2.66 (br s, 2H), 2.46 (m, 2H), 2.17 (s, 3H), 1.74 (br s, 1H), 1.64 (m, 2H), 1.46 (m, 2H), 1.29 (m, 10H), 1.22 (d, 3H, J=6.6 Hz), 0.90 (t, 3H, J=6.0 Hz). $^{13}$C NMR (150 MHz, CDCl$_3$): δ 163.8, 149.3, 148.1, 134.0, 128.1, 124.5, 97.5, 87.6, 78.0, 77.4, 75.6, 71.7, 69.7 (2C), 53.6, 31.8, 29.4, 29.2, 29.0, 28.8, 28.2, 22.6, 19.4, 17.0, 14.0, 13.5.

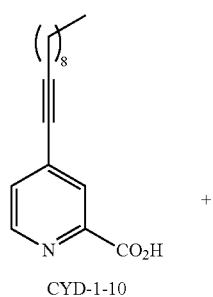

CYD-1-10

+

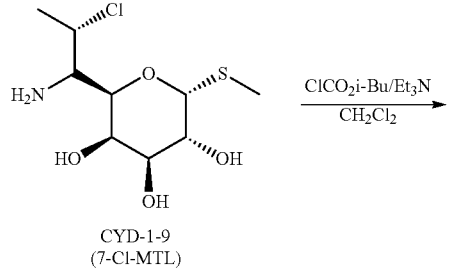

CYD-1-9
(7-Cl-MTL)

N-[2-Chloro-1-(3,4,5-trihydroxy-6-methylsulfanyl-tetrahydro-pyran-2-yl)-propyl]-2-piperidin-4-yl-benzamide (CYD-1-84)

To a solution of 2-(1-(tert-butoxycarbonyl)piperidin-4-yl) benzoic acid (50 mg, 0.16 mmol) and CYD-1-53 (45 mg, 0.16 mmol) in 5 mL of DMF was added HBTU (80 mg, 0.21 mmol) and DIPEA (53 mg, 0.41 mmol). The resulting mixture was stirred at room temperature for 3.5 hrs. After that, TLC showed that the starting material was gone. The solvent DMF was removed under vacuum to give a brown oil residue. The oil residue was partitioned between CH$_2$Cl$_2$ (30 ml) and 10% NaHSO$_4$ solution (8 mL). The organic layer was separated and washed with saturated aqueous NaHCO$_3$ (8 mL), dried over anhydrous Na$_2$SO$_4$, filtered and concentrated to give an oil residue. This residue was purified with silica gel column; eluting with 4% MeOH in CH$_2$Cl$_2$ afforded CYD-1-83 (30 mg, 32%). CYD-1-83 (30 mg, 0.05 mmol) was dissolved in 1 mL of CH$_2$Cl$_2$, and then 250 μL of TFA was added into it. The resulting mixture was stirred at room temperature. After 2 hrs, TLC showed the starting material was gone. The solvent was removed under vacuum. The residue was neutralized with saturated aqueous NaHCO$_3$ (8 mL), and then extracted with CHCl$_3$ (30 ml) for 3 times. TLC indicated that CYD-1-84 was still in water. The water was removed under vacuum. The residue was washed with CHCl$_3$ for 6 times, and then the organic layer was combined and concentrated to afford CYD-1-84 (13 mg, 52%) as a colorless gel. $^1$H NMR (600 MHz, CDCl$_3$) δ 7.42 (m, 2H), 7.31 (m, 1H), 7.25 (m, 1H), 6.43 (d, 1H, J=9.0 Hz), 5.28 (d, 1H, J=4.8 Hz), 4.98 (m, 1H), 4.56 (dd, 1H, J=1.8 Hz, 4.8 Hz), 4.48 (m, 1H), 4.15 (m, 2H), 3.87 (dd, 1H, J=3.6 Hz, 9.6 Hz), 3.18 (d, 2H, J=9.0 Hz), 3.09 (m, 1H), 2.71 (br s, 5H), 2.10 (s, 3H), 1.83 (m, 2H), 1.69 (m, 2H), 1.24 (d, 3H, J=6.0 Hz)

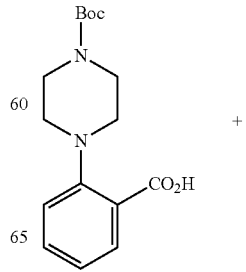

+

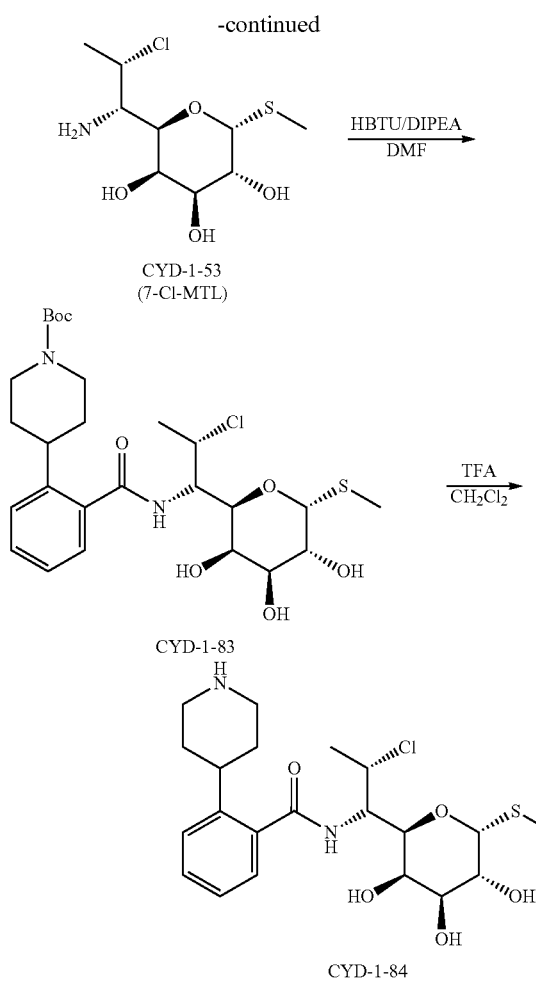

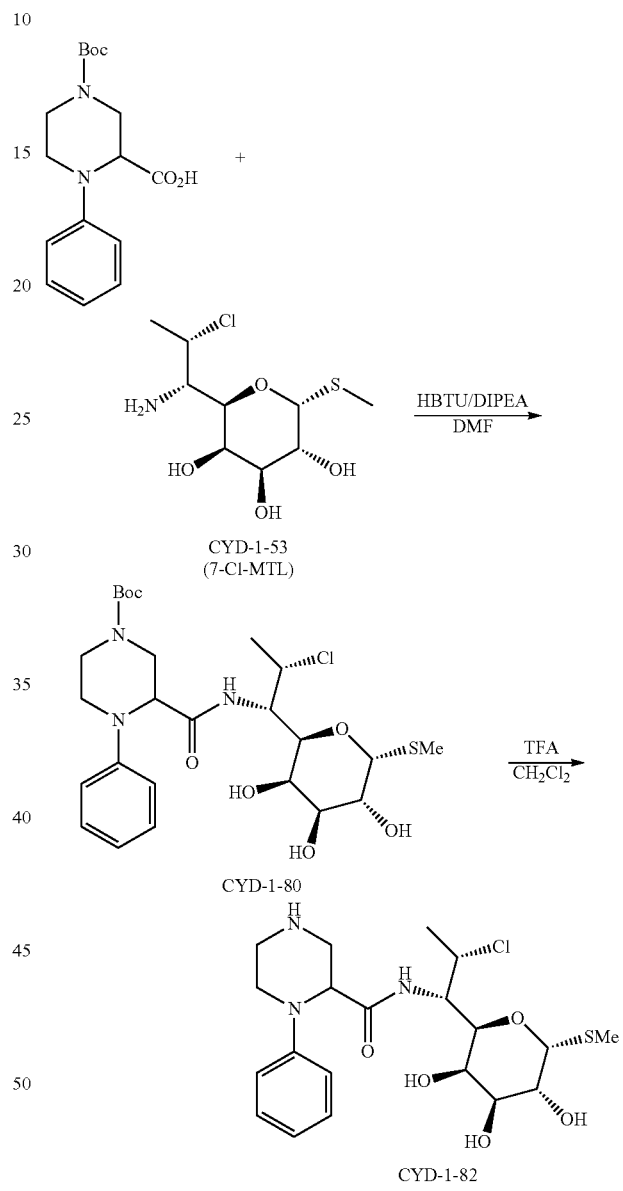

1-Phenyl-piperazine-2-carboxylic acid [2-chloro-1-(3,4,5-trihydroxy-6-methylsulfanyl-tetrahydro-pyran-2-yl)-propyl]amide (CYD-1-82)

To a solution of 4-(tert-butoxycarbonyl)-1-phenylpiperazine-2-carboxylic acid (50 mg, 0.16 mmol) and CYD-1-53 (48 mg, 0.18 mmol) in 5 mL of DMF was added HBTU (80 mg, 0.21 mmol) and DIPEA (52 mg, 0.40 mmol). The resulting mixture was stirred at room temperature for 16 hrs. After that, TLC showed that the starting material was gone. The solvent DMF was removed under vacuum to give a dark oil residue. The oil residue was partitioned between $CH_2Cl_2$ (50 ml) and 10% $NaHSO_4$ solution (10 mL). The organic layer was separated and washed with saturated aqueous $NaHCO_3$ (10 mL), dried over anhydrous $Na_2SO_4$, filtered and concentrated to give an oil residue. This residue was purified with silica gel column; eluting with 3% MeOH in $CH_2Cl_2$ afforded CYD-1-80 (32 mg, 35%) as a colorless gel. CYD-1-80 (32 mg, 0.05 mmol) was dissolved in 1 mL of $CH_2Cl_2$, and then 250 μL of TFA was added into it. The resulting mixture was stirred at room temperature. After 2 hrs, TLC showed the starting material was gone. The solvent was removed under vacuum. The residue was partitioned between $CH_2Cl_2$ (30 ml) and saturated aqueous $NaHCO_3$ (10 mL), dried over anhydrous $Na_2SO_4$, filtered and concentrated to give an oil residue. The residue was purified with preparative TLC; developing with 16% MeOH in $CH_2Cl_2$ afforded the amide CYD-1-82 (21 mg, 80%). $^1H$ NMR (600 MHz, $CDCl_3$) δ 7.26 (m, 5H), 6.90 (m, 6H), 6.82 (d, 1H, J=9.0 Hz), 5.22 (d, 1H, J=4.8 Hz), 5.09 (d, 1H, J=4.8 Hz), 4.74 (m, 1H), 4.88 (m, 1H), 4.39 (d, 1H, J=3.0 Hz), 4.29 (m, 1H), 4.15 (m, 4H), 4.01 (m, 4H), 3.79 (dd, 1H, J=3.6 Hz, 9.6 Hz), 3.74 (dd, 1H, J=3.0 Hz, 9.6 Hz), 3.43 (m, 2H), 3.26 (m, 4H), 3.07 (m, 6H), 2.48 (br s, 8H), 2.12 (s, 3H), 1.80 (s, 3H), 1.10 (d, 3H, J=6.6 Hz), 0.61 (d, 3H, J=6.6 Hz).

N-(1,3-Dihydroxypropan-2-yl)-2-(piperidin-4-yl)benzamide (CYD-3-33)

To a solution of 2-(1-(tert-butoxycarbonyl)piperidin-4-yl) benzoic acid (100 mg, 0.32 mmol) and 2-aminopropane-1,3-diol (34 mg, 0.32 mmol) in 5 mL of DMF was added HBTU (161 mg, 0.42 mmol) and DIPEA (105 mg, 0.82 mmol). The resulting mixture was stirred at room temperature for 16 hrs. The solvent DMF was removed under vacuum to give a dark oil residue, which was then partitioned between $CH_2Cl_2$ (50 mL) and 10% $NaHSO_4$ solution (10 mL). The organic layer was separated and washed with saturated aqueous NaHCO$_3$ (10 mL), dried over anhydrous Na$_2$SO$_4$, filtered and concentrated to give an oil residue. This residue was purified with silica gel column; eluting with 5% MeOH in CH$_2$Cl$_2$ afforded CYD-3-28 (80 mg, 64%). CYD-3-28 (80 mg, 0.21 mmol) was dissolved in 1 mL of CH$_2$Cl$_2$, followed by the addition of 250 µL of TFA. The resulting mixture was stirred at room temperature. After 2 hrs, the solvent was removed under vacuum. The residue was partitioned between CH$_2$Cl$_2$ (30 ml) and saturated aqueous NaHCO$_3$ (10 mL), dried over anhydrous Na$_2$SO$_4$, filtered and concentrated to give an oil residue. The residue was purified with preparative TLC; developing with 18% MeOH in CH$_2$Cl$_2$ afforded the amide CYD-3-33 (20 mg, 34%). $^1$H NMR (600 MHz, CDCl$_3$+CD$_3$OD) δ 7.38 (m, 3H), 7.23 (m, 1H), 4.16 (t, 1H, J=5.4 Hz), 3.73 (m, 4H), 3.16 (d, 2H, J=12.0 Hz), 3.08 (m, 1H), 2.75 (m, 2H), 1.88 (d, 2H, J=12.6 Hz), 1.71 (dq, 2H, J=3.6 Hz and 13.2 Hz). $^{13}$C NMR (150 MHz, CDCl$_3$+CD$_3$OD) δ 172.0, 143.1, 136.5, 129.6, 126.6, 126.1, 125.7, 60.7 (2C), 53.4, 53.3, 45.9, 38.4, 32.9 (2C).

HBTU (161 mg, 0.42 mmol) and DIPEA (105 mg, 0.82 mmol). The resulting mixture was stirred at room temperature for 16 hrs. After that, TLC showed that the starting material was gone. The solvent DMF was removed under vacuum to give a dark oil residue, which was then partitioned between CH$_2$Cl$_2$ (50 ml) and 10% NaHSO$_4$ solution (10 mL). The organic layer was separated and washed with saturated aqueous NaHCO$_3$ (10 mL), dried over anhydrous Na$_2$SO$_4$, filtered and concentrated to give an oil residue. This residue was purified with silica gel column; eluting with 3% MeOH in CH$_2$Cl$_2$ afforded CYD-3-29 (89 mg, 71%) as a colorless gel. CYD-3-29 (89 mg, 0.23 mmol) was dissolved in 1 mL of CH$_2$Cl$_2$, and then 250 µL of TFA was added into it. The resulting mixture was stirred at room temperature. After 2 hrs, the solvent was removed under vacuum. The residue was partitioned between CH$_2$Cl$_2$ (30 ml) and saturated aqueous NaHCO$_3$ (10 mL), dried over anhydrous Na$_2$SO$_4$, filtered and concentrated to give an oil residue. The residue was purified with preparative TLC; developing with 16% MeOH in CH$_2$Cl$_2$ afforded CYD-3-35 (35 mg, 53%) as a colorless gel. $^1$H NMR (600 MHz, CDCl$_3$+CD$_3$OD) δ 7.78 (br s, 1H), 7.46 (m, 2H), 7.39 (d, 1H, J=7.2 Hz), 7.29 (m, 1H), 3.88 (s, 1H), 3.61 (m, 2H), 3.49 (m, 1H), 3.41 (s, 1H), 3.37 (s, 2H), 3.24 (d, 2H, J=11.4 Hz), 3.12 (m, 1H), 2.83 (t, 2H, J=12.0 Hz), 1.93 (m, 2H), 1.98 (q, 2H, J=12.6 Hz).

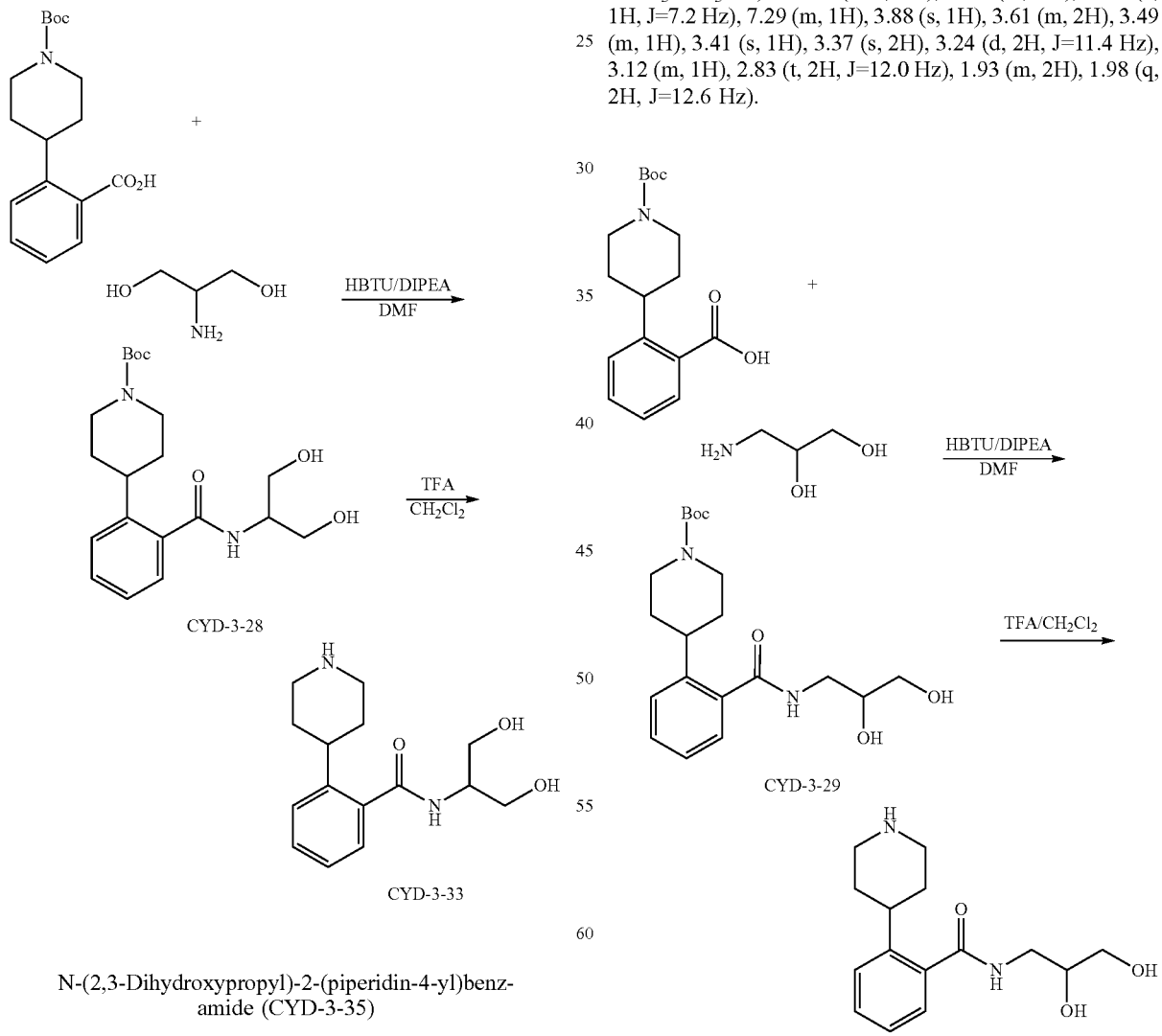

N-(2,3-Dihydroxypropyl)-2-(piperidin-4-yl)benzamide (CYD-3-35)

To a solution of 2-(1-(tert-butoxycarbonyl)piperidin-4-yl)benzoic acid (100 mg, 0.32 mmol) and 3-aminopropane-1,2-diol (30 mg, 0.32 mmol) in 5 mL of DMF was added

N-(2,3-Dihydroxypropyl)-1-phenylpiperazine-2-carboxamide (CYD-3-49)

To a solution of 4-(tert-butoxycarbonyl)-1-phenylpiperazine-2-carboxylic acid (100 mg, 0.32 mmol) and 3-aminopropane-1,2-diol (30 mg, 0.32 mmol) in 5 mL of DMF was added HBTU (161 mg, 0.42 mmol) and DIPEA (105 mg, 0.82 mmol). The resulting mixture was stirred at room temperature for 16 hrs. After that, TLC showed that the starting material was gone. The solvent DMF was removed under vacuum to give a dark oil residue, which was then partitioned between $CH_2Cl_2$ (50 ml) and 10% $NaHSO_4$ solution (10 mL). The organic layer was separated and washed with saturated aqueous $NaHCO_3$ (10 mL), dried over anhydrous $Na_2SO_4$, filtered and concentrated to give an oil residue. This residue was purified with silica gel column; eluting with 5% MeOH in $CH_2Cl_2$ afforded the amide CYD-3-34 (90 mg, 72%) as colorless gel. CYD-3-34 (90 mg, 0.23 mmol) was dissolved in 1 mL of $CH_2Cl_2$, and then 250 μL of TFA was added into it. The resulting mixture was stirred at room temperature. After 2 hr, the solvent was removed under vacuum to afford the TFA salt of the amide CYD-3-49 as a colorless gel (70 mg, 78%). $^1$H NMR (600 MHz, $CDCl_3+CD_3OD$) δ 7.31 (m, 2H), 7.05 (d, 1H, J=7.8 Hz), 6.97 (m, 1H), 4.54 (s, 1H), 3.68 (m, 2H), 3.58 (m, 2H), 3.36 (m, 5H), 3.27 (m, 2H).

N-((1S,2S)-1,3-dihydroxy-1-phenylpropan-2-yl)-2-(piperidin-4-yl)benzamide (CYD-3-50)

To a solution of 2-(1-(tert-butoxycarbonyl)piperidin-4-yl)benzoic acid (100 mg, 0.32 mmol) and (1S,2S)-2-amino-1-phenylpropane-1,3-diol (54 mg, 0.32 mmol) in 5 mL of DMF was added HBTU (161 mg, 0.42 mmol) and DIPEA (105 mg, 0.82 mmol). The resulting mixture was stirred at room temperature for 16 hrs. After that, TLC showed that the starting material was gone. The solvent DMF was removed under vacuum to give a dark oil residue. The oil residue was partitioned between $CH_2Cl_2$ (50 mL) and 10% $NaHSO_4$ solution (10 mL). The organic layer was separated and washed with saturated aqueous $NaHCO_3$ (10 mL), dried over anhydrous $Na_2SO_4$, filtered and concentrated to give an oil residue. This residue was purified with silica gel column; eluting with 5% MeOH in $CH_2Cl_2$ afforded the amide CYD-3-32 (85 mg, 57%). CYD-3-32 (85 mg, 0.18 mmol) was dissolved in 1 mL of $CH_2Cl_2$, and then 250 μL of TFA was added into it. The resulting mixture was stirred at rt. After 2 hrs, the solvent was removed under vacuum to afford the TFA salt of the amide CYD-3-50 as a colorless gel (65 mg, 77%). $^1$H NMR (600 MHz, $CDCl_3+CD_3OD$) δ 7.32 (m, 9H), 4.96 (m, 1H), 4.40 (m, 1H), 3.77 (m, 1H), 3.61 (m, 1H), 3.38 (m, 2H), 2.99 (m, 1H), 2.88 (m, 2H), 2.00 (d, 1H, J=13.2 Hz), 1.84 (m, 3H).

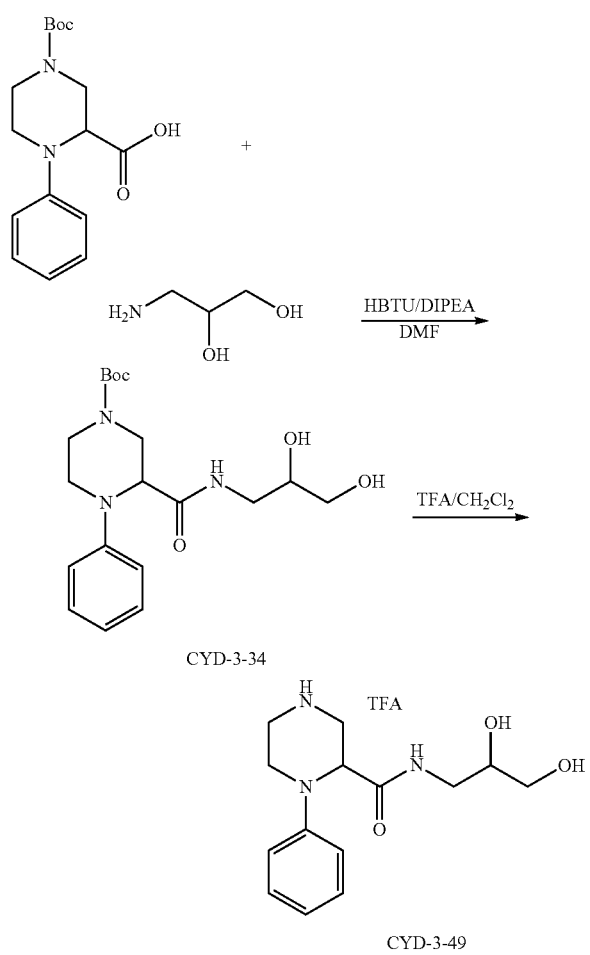

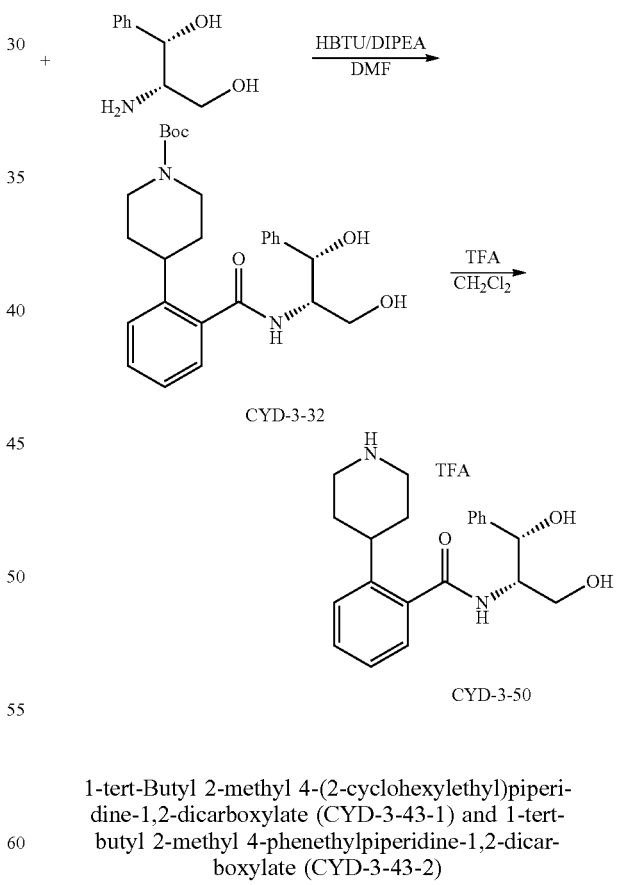

1-tert-Butyl 2-methyl 4-(2-cyclohexylethyl)piperidine-1,2-dicarboxylate (CYD-3-43-1) and 1-tert-butyl 2-methyl 4-phenethylpiperidine-1,2-dicarboxylate (CYD-3-43-2)

To a dried flask was added CYD-1-4 (500 mg, 1.9 mmol, 1 equiv.), triphenylphosphine 50 mg, 0.19 mmol, 0.1 equiv.), copper (I) iodide (36 g, 0.19 mmol, 0.1 equiv), palladium acetate (21 mg, 0.095 mmol, 0.05 equiv) and triethylamine (8 mL). The mixture was degassed with nitrogen, followed by addition of ethynylbenzene (388 mg, 3.8 mmol, 2.0 equiv). The reaction mixture was stirred at room temperature for 12 h. The insoluble solid was filtered and the filtrate was concentrated under the vacuum, and the dark residue was purified with silica gel chromatography; eluting with 1:3 ethyl acetate-hexane provided the desired product CYD-3-37 as a brown oil (400 mg, 88%). To a solution of CYD-3-37 (400 mg, 1.68 mmol) in a mixture of MeOH (9 mL), water (6 mL) and 37% hydrochloric acid (140 µL, 1.68 mol) was added platinum oxide (190 mg, 0.84 mmol). The reaction mixture was purged and charged with hydrogen (60 psi) for 24 hrs. The platinum oxide was removed by filtration and the filtrate was concentrated to give an oil residue. The residue was diluted with $CH_2Cl_2$ and washed with the saturated $NaHCO_3$ aqueous solution. After drying over anhydrous $Na_2SO_4$, the solvent was removed under vacuum to give a colorless oil residue (400 mg, 98%). $^1$H NMR indicated that the residue was a mixture of two products. To a solution of the residue (400 mg) in methanol (10 mL) was added $Et_3N$ (424 mg, 4.2 mmol) and $(Boc)_2O$ (438 mg, 2.01 mmol). The mixture was stirred at room temperature overnight. The solvent was removed under vacuum to give an oil residue. The residue was purified with silica gel column; eluting with 6:1 hexane-ethyl acetate gave the Boc-protection product CYD-3-43-1 (160 mg, 26%) and CYD-3-43-2 (220 mg, 37%) as colorless gel, respectively.

CYD-3-43-1: $^1$H NMR (600 MHz, $CDCl_3$) δ 4.30 (m, 1H), 3.72 (s, 3H), 3.55 (m, 1H), 3.36 (m, 1H), 1.96 (m, 1H), 1.78 (m, 2H), 1.65 (m, 5H), 1.55 (t, 1H, J=5.4 Hz), 1.43 (s, 9H), 1.37 (m, 1H), 1.19 (m, 8H), 0.85 (m, 2H). $^{13}$C NMR (150 MHz, $CDCl_3$) δ 173.4, 155.9, 80.0, 54.4, 51.8, 37.2, 34.9, 33.3 (2C), 31.6, 31.2, 30.6, 29.2, 28.2 (3C), 26.6 (2C), 26.2 (2C).

CYD-3-43-2: $^1$H NMR (600 MHz, $CDCl_3$) δ 7.26 (m, 2H), 7.16 (m, 3H), 4.33 (m, 1H), 3.71 (s, 3H), 3.58 (m, 1H), 3.37 (m, 1H), 2.61 (m, 2H), 2.00 (m, 1H), 1.88 (m, 1H), 1.77 (m, 1H), 1.65 (m, 1H), 1.57 (q, 2H, J=7.8 Hz), 1.43 (s, 10H). $^{13}$C NMR (150 MHz, $CDCl_3$) δ 173.3, 155.8, 142.0, 128.3 (2C), 128.2, 125.7 (2C), 80.1, 54.2, 51.9, 39.5, 35.0, 33.3, 30.9, 30.7, 29.1, 28.2 (3C).

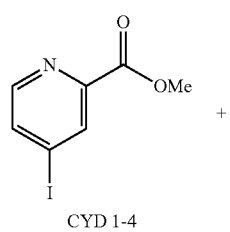
CYD 1-4

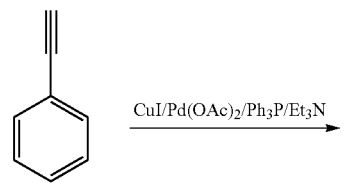

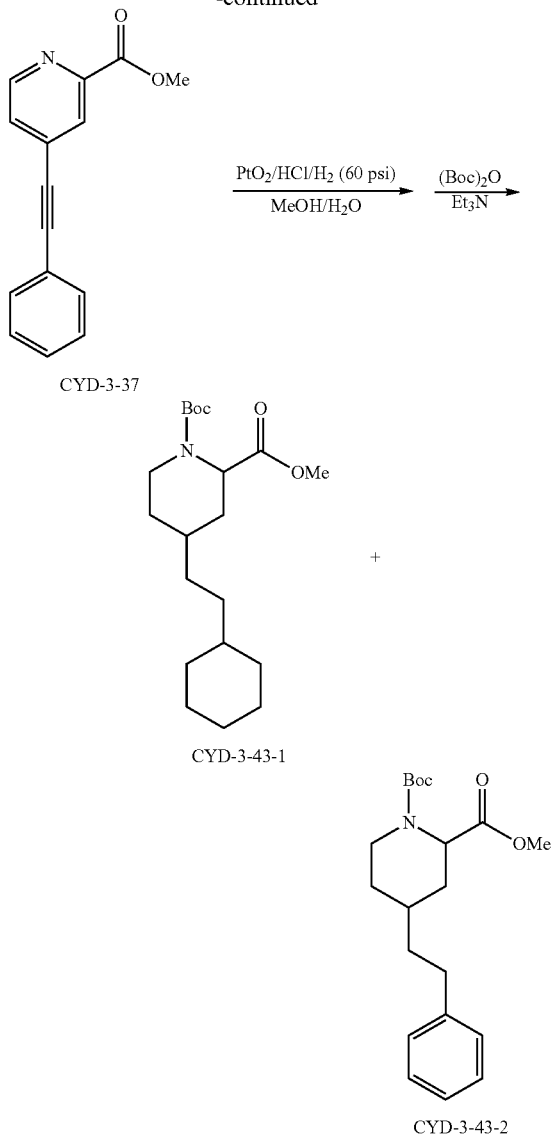

2,4-cis-4-Phenethyl-piperidine-2-carboxylic acid [2-hydroxy-1-(3,4,5-trihydroxy-6-methylsulfanyl-tetrahydro-pyran-2-yl)-propyl]-amide (CYD-3-61)

To solution of CYD-3-43-2 (250 mg, 0.72 mmol) in 12 mL of THF and 4 mL of water was added lithium hydroxide monohydrate (302 mg, 7.20 mmol). The mixture was stirred at room temperature for 48 hrs. THF was removed under vacuum. The aqueous layer was taken up in ethyl acetate, partitioned with 10% $NaHSO_4$ aqueous solution. The organic layer was washed with water and brine, and then dried over anhydrous $Na_2SO_4$ and concentrated under vacuum to give the desired product CYD-3-46 (240 mg, 99%) as a colorless oil. $^1$H NMR (600 MHz, $CDCl_3$) δ 10.6 (br s, 1H), 7.29 (t, 2H, J=6.6 Hz), 7.19 (m, 3H), 4.35 (s, 1H), 3.51 (br s, 1H), 3.43 (s, 1H), 2.64 (s, 2H), 2.07 (m, 1H), 1.85 (m, 2H), 1.67 (m, 3H), 1.46 (m, 10H). $^{13}$C NMR (150 MHz, $CDCl_3$) δ 178.7, 155.8, 141.9, 128.3 (3C), 128.2, 125.7, 80.6, 54.2, 39.5, 35.6, 33.2, 31.0, 30.7, 29.1, 28.2 (3C).

To a solution of CYD-3-46 (143 mg, 0.43 mmol) and 7-OH-MTL (CYD-1-6) (108 mg, 0.43 mmol) in 6 mL of DMF was added HBTU (211 mg, 0.55 mmol) and DIPEA (138 mg, 1.07 mmol). The resulting mixture was stirred at room temperature for 16 hrs. After that, TLC showed that the starting material disappeared. The solvent DMF was removed under vacuum to give a dark oil residue, which was then partitioned between CH₂Cl₂ (50 ml) and 10% citric aqueous solution (10 mL). The organic layer was separated and washed with saturated aqueous NaHCO₃ (10 mL). After drying over anhydrous Na₂SO₄, the solvent was removed under vacuum to give an oil residue. This residue was purified with silica gel column; eluting with 6% MeOH in CH₂Cl₂ afforded the amide CYD-3-52 (140 mg, 57%). Then, the amide CYD-3-52 (120 mg, 0.21 mmol) was dissolved in CH₂Cl₂ (1 mL), then TFA (250 µL) was added into it. The resulting mixture was stirred at room temperature. After 2 hrs, TLC showed the starting material disappeared. The solvent was removed under vacuum to give an oil residue. The residue was partitioned between CH₂Cl₂ (30 mL) and saturated NaHCO₃ aqueous solution (10 mL). The organic layer was dried over anhydrous Na₂SO₄, filtered and concentrated to give an oil residue. This residue was purified with silica gel column; eluting with 15% MeOH in CH₂Cl₂ afforded CYD-3-61 (60 mg, 60%) as a colorless gel. $^1$H NMR (600 MHz, CDCl₃+CD₃OD) δ 7.27 (m, 2H), 7.17 (m, 3H), 5.28 (m, 1H), 4.20 (m, 2H), 4.14 (m, 5H), 3.88 (d, 1H, J=19.8 Hz), 3.58 (d, 1H, J=9.6 Hz), 3.29 (m, 1H), 3.17 (m, 1H), 2.64 (m, 3H), 2.12 (s, 3H), 2.08 (d, 1H, J=7.8 Hz), 1.78 (m, 1H), 1.58 (m, 2H), 1.14 (m, 6H). $^{13}$C NMR (150 MHz, CDCl₃+CD₃OD) δ 175.3, 175.1, 142.1, 142.0, 128.2 (2C), 128.1 (6C), 125.6 (2C), 88.4, 88.3, 70.6 (2C), 70.1, 69.7, 68.7, 68.5, 68.1, 66.5, 66.3, 60.0, 59.7, 53.9, 53.3, 45.2, 44.8, 38.4, 38.3, 36.2, 35.9, 35.1, 35.0, 32.5, 32.4, 31.8, 31.4, 29.5, 17.4, 16.8, 13.6, 13.5.

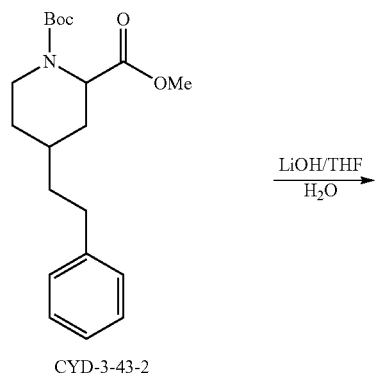

2,4-cis-4-(2-Cyclohexyl-ethyl)-piperidine-2-carboxylic acid [2-hydroxy-1-(3,4,5-trihydroxy-6-methyl-sulfanyl-tetrahydro-pyran-2-yl)-propyl]-amide (CYD-3-62)

To a solution of CYD-3-43-1 (160 mg, 0.45 mmol) in 12 mL of THF and 4 mL of water was added lithium hydroxide monohydrate (84 mg, 2.0 mmol). The mixture was stirred at room temperature for 48 hrs. THF was removed under vacuum. The aqueous layer was taken up in ethyl acetate, and partitioned with 10% NaHSO₄ aqueous solution. The organic layer was washed with water and brine, and then dried over anhydrous Na₂SO₄ and concentrated under vacuum to give the desired product CYD-3-51 (140 mg, 91%) as a colorless oil.

To a solution of CYD-3-51 (114 mg, 0.33 mmol) and 7-OH-MTL (CYD-1-6) (85 mg, 0.33 mmol) in 6 mL of DMF was added HBTU (165 mg, 0.43 mmol) and DIPEA (108 mg, 0.83 mmol). The resulting mixture was stirred at room temperature for 16 hrs. After that, TLC showed that the starting material disappeared. The solvent DMF was removed under vacuum to give an oil residue. The oil residue was partitioned between CH₂Cl₂ (50 ml) and 10% citric aqueous solution (10 mL). The organic layer was separated and washed with saturated aqueous NaHCO₃ (10 mL). After drying over anhydrous Na₂SO₄, the solvent was removed under vacuum to give an oil residue. This residue was purified with silica gel column; eluting with 6% MeOH in CH₂Cl₂ afforded the amide CYD-3-59 (85 mg, 44%). Then, the amide CYD-3-59 (80 mg, 0.14 mmol) was dissolved in CH₂Cl₂ (1 mL), then TFA (250 µL) was added into it. The resulting mixture was stirred at room temperature.

After 2 hrs, TLC showed the starting material disappeared. The solvent was removed under vacuum to give an oil residue. The residue was partitioned between CH$_2$Cl$_2$ (30 mL) and saturated NaHCO$_3$ aqueous solution (10 mL). The organic layer was dried over anhydrous Na$_2$SO$_4$, filtered and concentrated to give an oil residue. This residue was purified with silica gel column; eluting with 15% MeOH in CH$_2$Cl$_2$ afforded CYD-3-62 (40 mg, 60%) as a colorless gel. $^1$H NMR (600 MHz, CDCl$_3$+CD$_3$OD) δ 5.27 (m, 1H), 4.22 (m, 1H), 4.09 (m, 3H), 3.89 (s, 1H), 3.58 (d, 1H, J=9.6 Hz), 3.42 (m, 1H), 3.22 (m, 1H), 2.72 (m, 1H), 2.10 (s, 3H), 2.03 (m, 1H), 1.75 (m, 1H), 1.68 (m, 6H), 1.43 (m, 1H), 1.18 (m, 13H), 0.86 (m, 2H). $^{13}$C NMR (150 MHz, CDCl$_3$+CD$_3$OD) δ 178.2, 178.0, 92.5 (2C), 74.5, 74.2, 73.9, 73.6, 72.7, 72.5, 71.9 (2C), 70.4 (2C), 70.3, 70.2, 63.7, 63.4, 57.6, 57.1, 48.9, 48.6, 41.6, 39.6 (2C), 39.5 39.4, 37.9, 37.7, 37.6, 37.2, 37.1, 36.7, 35.0, 34.6, 33.5, 30.4, 30.1, 20.9, 20.8, 20.4 (2C), 17.6 (3C).

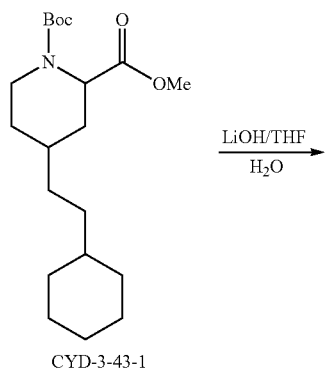

CYD-3-43-1

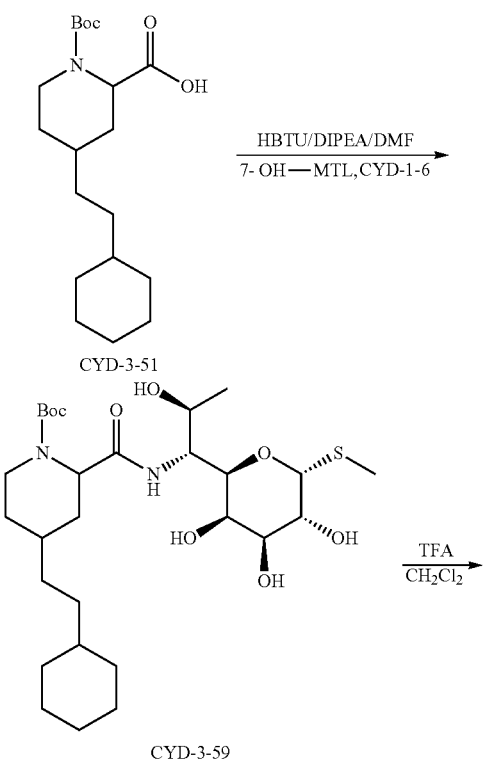

CYD-3-51

CYD-3-59

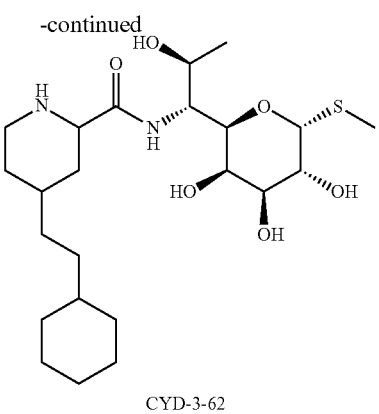

CYD-3-62

(2S,4R)—N-((1R,2R)-1,3-dihydroxy-1-phenylpropan-2-yl)-4-undecylpiperidine-2-carboxamide (CYD-5-68-1) and (2R,4S)—N-((1R,2R)-1,3-dihydroxy-1-phenylpropan-2-yl)-4-undecylpiperidine-2-carboxamide (CYD-5-68-2)

To a solution of CYD-1-66 (140 mg, 0.36 mmol) and (1R,2R)-2-amino-1-phenylpropane-1,3-diol (60 mg, 0.36 mmol) in 6 mL of CH$_2$Cl$_2$ was added HBTU (179 mg, 0.47 mmol) and DIPEA (117 mg, 0.90 mmol). The resulting mixture was stirred at room temperature for 16 h. After that, the reaction was partitioned between CH$_2$Cl$_2$ (50 ml) and 10% citric aqueous solution (10 mL). The organic layer was separated and washed with saturated aqueous NaHCO$_3$ (10 mL). After drying over anhydrous Na$_2$SO$_4$, the solvent was removed under vacuum to give an oily residue. This residue was purified with silica gel column; eluting with 10% MeOH in CH$_2$Cl$_2$ afforded the amide CYD-5-64 (120 mg, 62%). The amide CYD-5-64 (100 mg, 0.18 mmol) was dissolved in CH$_2$Cl$_2$ (2 mL), followed by the addition of TFA (500 μL). The resulting mixture was stirred at room temperature. After 2 h, TLC showed the starting material disappeared. The solvent was removed under vacuum to give an oily residue, which was partitioned between CH$_2$Cl$_2$ (30 mL) and saturated NaHCO$_3$ aqueous solution (10 mL). The organic layer was dried with anhydrous Na$_2$SO$_4$, filtered and concentrated to give an oily residue. This residue was purified with silica gel column; eluting with 15% MeOH in CH$_2$Cl$_2$ afforded CYD-5-68-1 (35 mg, 43%) and CYD-5-68-2 (37 mg, 45%) as a colorless gel, respectively.

CYD-5-68-1: $^1$H NMR (600 MHz, CDCl$_3$+CD$_3$OD) δ 7.67 (br s, 1H), 7.40 (d, 2H, J=7.8 Hz), 7.31 (t, 2H, J=7.8 Hz), 1.24 (t, 1H, J=7.8 Hz), 4.94 (d, 1H, J=4.8 Hz), 4.10 (m, 1H), 3.67 (dd, 1H, J=6.0 Hz, 11.4 Hz), 3.52 (dd, 1H, J=6.0 Hz, 11.4 Hz), 3.17 (d, 1H, J=12.6 Hz), 2.71 (m, 1H), 1.93 (d, 1H, J=13.2 Hz), 1.75 (d, 1H, J=13.8 Hz), 1.46 (br s, 1H), 1.28 (s, 20H), 1.14 (m, 1H), 0.97 (q, 1H, J=12.6 Hz), 0.89 (t, 3H, J=7.2 Hz). $^{13}$C NMR (150 MHz, CDCl$_3$): δ 172.9, 141.8, 128.0 (2C), 127.3, 126.0 (2C), 71.7, 61.4, 59.5, 56.7, 44.5, 36.5, 35.5, 35.1, 31.7, 30.6, 29.6 (4C), 29.4, 29.1, 26.1, 22.4, 13.5.

CYD-5-68-2: $^1$H NMR (600 MHz, CDCl$_3$) δ 7.40 (d, 1H, J=8.4 Hz), 7.35 (d, 2H, J=7.2 Hz), 7.28 (m, 2H), 7.21 (t, 1H, J=7.8 Hz), 5.02 (d, 1H, J=3.0 Hz), 4.52 (br s, 2H), 4.08 (m, 1H), 3.77 (m, 1H), 3.71 (m, 1H), 3.13 (dd, 1H, J=1.8 Hz, 12.0 Hz), 2.94 (d, 1H, J=11.4 Hz), 2.43 (m, 1H), 1.71 (d, 1H, J=12.6 Hz), 1.56 (d, 1H, J=12.0 Hz), 1.26 (m, 20H), 0.99 (m, 2H), 0.88 (t, 3H, J=7.2 Hz), 0.73 (q, 1H, J=12.0 Hz). $^{13}$C NMR (150 MHz, CDCl$_3$): δ 173.8, 141.7, 128.2 (2C), 127.4, 125.9 (2C), 72.9, 63.0, 60.0, 56.3, 44.9, 36.8, 36.4, 35.4, 31.9, 31.8, 29.8, 29.7 (4C), 29.4, 26.3, 22.7, 14.1.

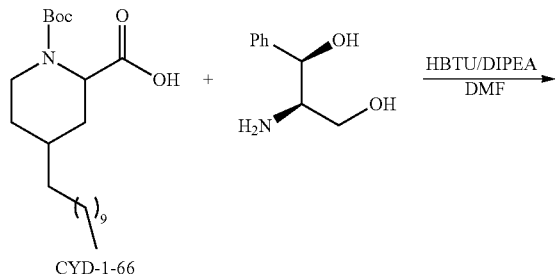

CYD-1-66

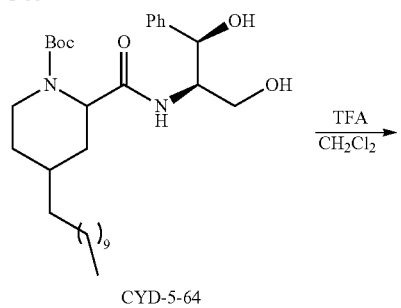

CYD-5-64

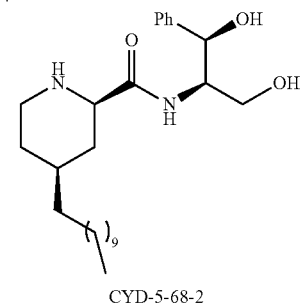

CYD-5-68-2

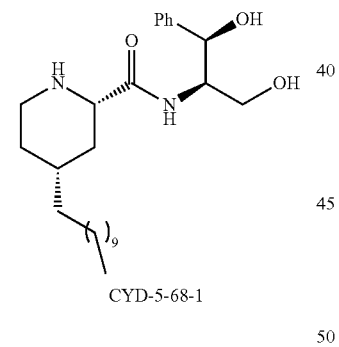

CYD-5-68-1

N-((2R,3R)-1,3-dihydroxybutan-2-yl)-4-undecylpiperidine-2-carboxamide (CYD-5-69)

To a solution of CYD-1-66 (70 mg, 0.18 mmol) and L-threoninol (20 mg, 0.18 mmol) in 4 mL of DMF was added HBTU (89 mg, 0.23 mmol) and DIPEA (58 mg, 0.45 mmol). The resulting mixture was stirred at room temperature for 16 h. The solvent DMF was removed under vacuum to give a brown oily residue, which was then partitioned between $CH_2Cl_2$ (50 ml) and 10% citric aqueous solution (10 mL). The organic layer was separated and washed with saturated aqueous $NaHCO_3$ (10 mL). After drying over anhydrous $Na_2SO_4$, the solvent was removed under vacuum to give an oily residue. This residue was purified with silica gel column; eluting with 5% MeOH in $CH_2Cl_2$ afforded the amide CYD-5-62 (45 mg, 50%). The amide CYD-5-62 (45 mg, 0.09 mmol) was dissolved in $CH_2Cl_2$ (1 mL), followed by the addition of TFA (250 μL). The resulting mixture was stirred at room temperature. After 2 h, TLC showed the starting material disappeared. The solvent was removed under vacuum to give an oily residue. The residue was partitioned between $CH_2Cl_2$ (30 mL) and saturated $NaHCO_3$ aqueous solution (10 mL). The organic layer was dried over anhydrous $Na_2SO_4$, filtered and concentrated to give an oily residue. This residue was purified with silica gel column; eluting with 10% MeOH in $CH_2Cl_2$ afforded CYD-5-69 (30 mg, 84%) as a colorless gel. $^1$H NMR (600 MHz, CDCl$_3$) δ 7.27 (m, 1H), 4.10 (m, 1H), 3.77 (m, 6H), 3.31 (dd, 1H, J=2.4 Hz, 12.0 Hz), 3.25 (dd, 1H, J=2.4 Hz, 11.4 Hz), 3.15 (m, 1H), 2.65 (t, 1H, J=12.6 Hz), 2.05 (m, 1H), 1.68 (m, 1H), 1.43 (m, 1H), 1.25 (m, 19H), 1.17 (m, 3H), 1.08 (m, 2H), 0.88 (t, 3H, J=7.2 Hz). $^{13}$C NMR (150 MHz, CDCl$_3$): δ 174.8, 174.1, 67.8, 67.6, 63.7, 60.9, 60.4, 54.9, 45.7, 45.3, 37.0, 36.8, 35.9, 35.7, 32.2, 31.9, 29.8, 29.6, 29.3, 26.5, 26.4, 22.6, 20.4 (2C), 14.1.

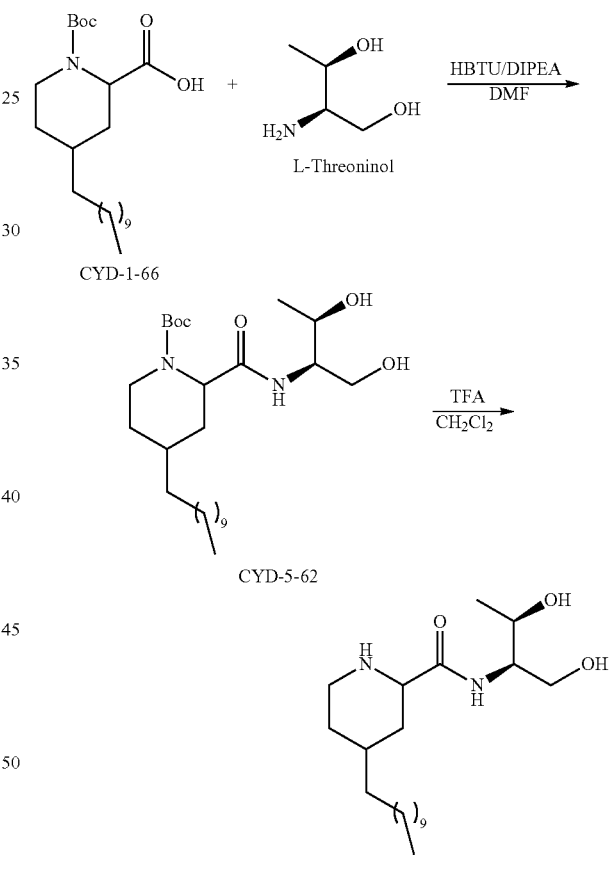

N-((2S,3S)-1,3-dihydroxybutan-2-yl)-4-undecylpiperidine-2-carboxamide (CYD-5-73)

To a solution of CYD-1-66 (70 mg, 0.18 mmol) and D-threoninol (20 mg, 0.18 mmol) in 4 mL of DMF was added HBTU (89 mg, 0.23 mmol) and DIPEA (58 mg, 0.45 mmol). The resulting mixture was stirred at room temperature for 16 h. The solvent DMF was removed under vacuum to give an oily residue, which was then partitioned between $CH_2Cl_2$ (50 mL) and 10% citric aqueous solution (10 mL).

The organic layer was separated and washed with saturated aqueous NaHCO$_3$ (10 mL). After drying over anhydrous Na$_2$SO$_4$, the solvent was removed under vacuum to give an oily residue. This residue was purified with silica gel column; eluting with 5% MeOH in CH$_2$Cl$_2$ afforded the amide CYD-5-63 (60 mg, 67%). The amide CYD-5-63 (60 mg, 0.12 mmol) was dissolved in CH$_2$Cl$_2$ (4 mL), followed by the addition of TFA (1 mL). The resulting mixture was stirred at room temperature. After 2 h, TLC showed the starting material disappeared. The solvent was removed under vacuum to give an oily residue, which was partitioned between CH$_2$Cl$_2$ (30 mL) and saturated NaHCO$_3$ aqueous solution (10 mL). The organic layer was dried over anhydrous Na$_2$SO$_4$, filtered and concentrated to give an oily residue. This residue was purified with silica gel column; eluting with 10% MeOH in CH$_2$Cl$_2$ afforded CYD-5-73 (45 mg, 95%) as a colorless gel. $^1$H NMR (600 MHz, CDCl$_3$) δ 7.59 (m, 1H), 4.78 (br s, 3H), 4.06 (m, 1H), 3.74 (m, 3H), 3.5 (m, 1H), (m, 1H), 2.73 (q, 1H, J=13.8 Hz), 2.06 (m, 1H), 1.74 (t, 1H, J=13.8 Hz), 1.47 (m, 1H), 1.25 (m, 19H), 1.15 (m, 5H), 0.87 (t, 3H, J=7.2 Hz). $^{13}$C NMR (150 MHz, CDCl$_3$): δ 173.7, 172.9, 67.6, 67.4, 63.3, 60.3, 59.7, 55.5, 45.2, 44.7, 36.7, 36.2, 36.0, 35.5, 35.2, 31.9, 31.2, 30.9, 29.8, 29.6, 29.3, 26.4 (2C), 22.6, 20.3, 14.1.

(2R,4S)—N-((1S,2S)-1,3-dihydroxy-1-(4-(methylthio)phenyl)propan-2-yl)-4-undecylpiperidine-2-carboxamide (CYD-5-77-1) and (2S,4R)—N-((1S,2S)-1,3-dihydroxy-1-(4-(methylthio)phenyl)propan-2-yl)-4-undecylpiperidine-2-carboxamide (CYD-5-77-2)

To a solution of CYD-1-66 (105 mg, 0.27 mmol) and (1S,2S)-(+)-thiomicamine (58 mg, 0.27 mmol) in 6 mL of CH$_2$Cl$_2$ was added HBTU (134 mg, 0.35 mmol) and DIPEA (88 mg, 0.68 mmol). The resulting mixture was stirred at room temperature for 4 h. After that, the reaction mixture was partitioned between CH$_2$Cl$_2$ (50 mL) and 10% citric aqueous solution (10 mL). The organic layer was separated and washed with saturated aqueous NaHCO$_3$ (10 mL). After drying over anhydrous Na$_2$SO$_4$, the solvent was removed under vacuum to give an oily residue. This residue was purified with silica gel column; eluting with 5% MeOH in CH$_2$Cl$_2$ afforded the amide CYD-5-65 (100 mg, 63%). The amide CYD-5-65 (100 mg, 0.17 mmol) was dissolved in CH$_2$Cl$_2$ (4 mL), followed by the addition of TFA (1 mL). The resulting mixture was stirred at room temperature. After 2 h, TLC showed the starting material disappeared. The solvent was removed under vacuum to give an oily residue, which was partitioned between CH$_2$Cl$_2$ (30 mL) and saturated NaHCO$_3$ aqueous solution (10 mL). The organic layer was dried with anhydrous Na$_2$SO$_4$, filtered and concentrated to give an oily residue. This residue was purified with silica gel column; eluting with 10% MeOH in CH$_2$Cl$_2$ afforded CYD-5-77-1 (40 mg, 48%) and CYD-5-77-2 (32 mg, 39%) as a colorless gel, respectively.

CYD-5-77-1: $^1$H NMR (600 MHz, CDCl$_3$+CD$_3$OD) δ 7.47 (br s, 1H), 7.31 (m, 2H), 7.23 (t, 2H, J=9.0 Hz), 4.94 and 4.84 (m, 1H), 4.05 (m, 1H), 3.76 and 3.69 (m, 1H), 3.60 (m, 1H), 3.12 (m, 2H), 2.61 (m, 1H), 2.45 (m, 3H), 1.81 (m, 1H), 1.68 (d, 1H, J=13.2 Hz), 1.39 (m, 1H), 1.27 (m, 20H), 1.02 (m, 1H), 0.88 (t, 3H, J=7.2 Hz), 0.77 (m, 1H). $^{13}$C NMR (150 MHz, CDCl$_3$): δ 174.8, 174.2, 138.6, 138.2, 137.6, 137.5, 126.8, 126.5, 126.4, 73.6, 71.8, 62.0, 60.7, 60.3, 56.3, 55.5, 45.2, 36.8, 36.4, 36.3, 35.7, 32.0, 31.8, 29.7, 29.5, 29.2, 26.3, 22.5, 15.5, 13.7.

CYD-5-77-2: $^1$H NMR (600 MHz, CDCl$_3$+CD$_3$OD) δ 7.55 (d, 1H, J=7.8 Hz), 7.44 (d, 1H, J=7.8 Hz), 7.27 (m, 4H), 7.19 (m, 4H), 4.96 (m, 1H), 4.86 (m, 1H), 4.48 (br s, 6H), 4.06 (m, 2H), 3.68 (m, 4H), 3.25 (m, 2H), 3.05 (m, 2H), 2.55 (m, 2H), 2.45 (s, 3H), 2.43 (s, 3H), 1.82 (m, 1H), 1.75 (d, 1H, J=12.6 Hz), 1.64 (m, 2H), 1.26 (m, 40H), 1.15 (m, 2H), 0.96 (m, 2H), 0.88 (t, 6H, J=7.2 Hz). $^{13}$C NMR (150 MHz, CDCl$_3$+CD$_3$OD): δ 173.4, 173.0, 138.5, 138.1, 137.9, 137.6, 126.8, 126.5, 74.2, 72.8, 63.0, 61.1, 59.9, 56.4, 55.6, 45.0, 44.8, 36.7, 36.1, 35.9, 35.2, 31.9, 31.3 (2C), 29.8, 29.6, 29.3, 26.3, 22.6, 15.8, 14.0.

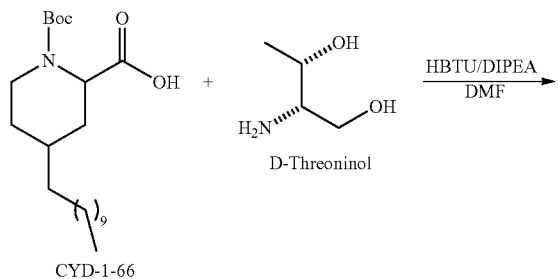

CYD-1-66 + D-Threoninol → (HBTU/DIPEA, DMF)

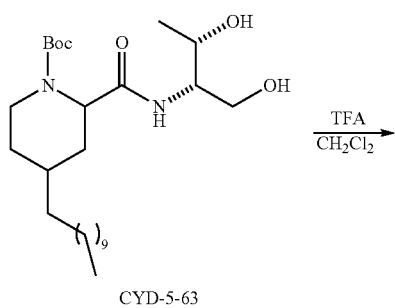

CYD-5-63 → (TFA, CH$_2$Cl$_2$)

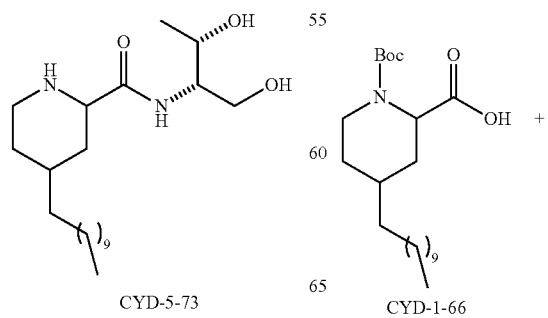

CYD-5-73

CYD-1-66

-continued

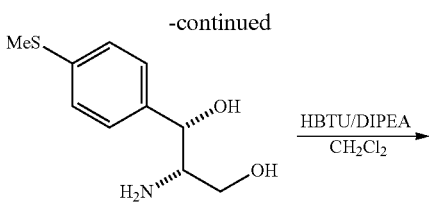

D-Threoninol

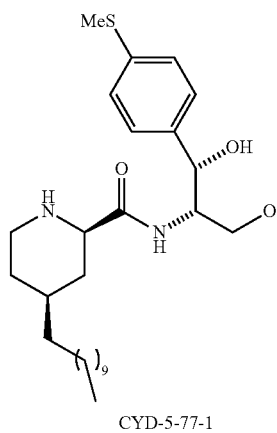

CYD-5-65

CYD-5-77-1

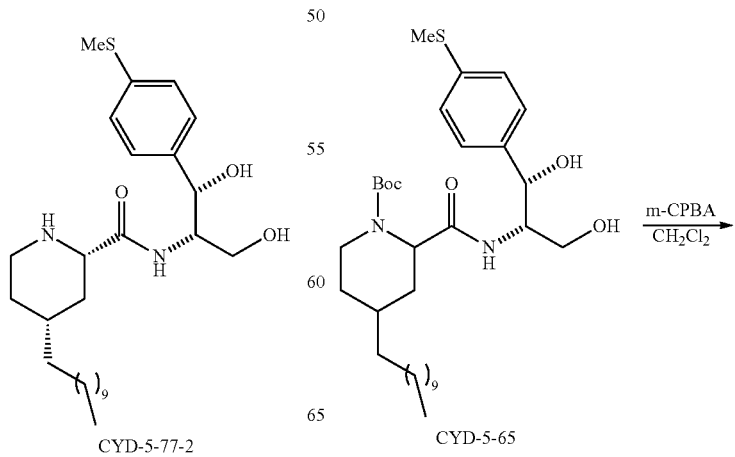

CYD-5-77-2

(2R,4S)—N-((1S,2S)-1,3-dihydroxy-1-(4-(methylsulfonyl)phenyl)propan-2-yl)-4-undecylpiperidine-2-carboxamide (CYD-5-80-1) and (2S,4R)—N-((1S,2S)-1,3-dihydroxy-1-(4-(methylsulfonyl)phenyl)propan-2-yl)-4-undecylpiperidine-2-carboxamide (CYD-5-80-2)

To a solution of CYD-5-65 (80 mg, 0.14 mmol) in 6 mL of $CH_2Cl_2$ was added m-CPBA (85 mg, 0.49 mmol). The resulting mixture was stirred at room temperature for 6 h. After that, the reaction mixture was diluted with $CH_2Cl_2$ (20 ml) and washed with saturated $NaHCO_3$ aqueous solution (10 mL). After drying over anhydrous $Na_2SO_4$, the solvent was removed under vacuum to give an oily residue. This residue was purified with silica gel column; eluting with 5% MeOH in $CH_2Cl_2$ afforded the amide CYD-5-71 (80 mg, 96%). The amide CYD-5-71 (80 mg, 0.13 mmol) was dissolved in $CH_2Cl_2$ (4 mL), followed by the addition of TFA (1 mL). The resulting mixture was stirred at rt. After 2 h, TLC showed the starting material disappeared. The solvent was removed under vacuum to give an oily residue, which was partitioned between $CH_2Cl_2$ (30 mL) and saturated $NaHCO_3$ aqueous solution (10 mL). The organic layer was dried over anhydrous $Na_2SO_4$, filtered and concentrated to give an oily residue. This residue was purified with silica gel column; eluting with 10% MeOH in $CH_2Cl_2$ afforded CYD-5-80-1 (26 mg, 39%) and CYD-5-80-2 (27 mg, 40%) as a colorless gel, respectively.

CYD-5-80-1: $^1$H NMR (600 MHz, $CDCl_3$) δ 7.87 (d, 1H, J=8.4 Hz), 7.62 (d, 1H, J=8.4 Hz), 7.38 (d, 1H, J=9.4 Hz), 5.13 (d, 1H, J=3.0 Hz), 4.09 (m, 1H), 3.73 (m, 1H), 3.66 (m, 1H), 3.12 (dd, 1H, J=1.8 Hz, 12.0 Hz), 3.05 (s, 3H), 2.56 (t, 3H, J=9.6 Hz), 1.78 (d, 1H, J=12.0 Hz), 1.66 (d, 1H, J=12.0 Hz), 1.28 (m, 20H), 1.18 (m, 2H), 0.97 (m, 1H), 0.89 (t, 3H, J=7.2 Hz), 0.73 (q, 1H, J=12.0 Hz). $^{13}$C NMR (150 MHz, $CDCl_3$): δ 174.6, 148.3, 139.3, 127.6 (4C), 72.1, 62.5, 60.6, 56.1, 45.5, 44.4, 36.9, 36.6, 35.7, 31.9, 29.7 (6C), 29.3, 26.4, 22.7, 14.1.

CYD-5-80-2: $^1$H NMR (600 MHz, $CDCl_3$) δ 7.84 (d, 1H, J=8.4 Hz), 7.57 (d, 1H, J=7.8 Hz), 7.43 (d, 1H, J=7.8 Hz), 5.09 (s, 1H), 4.49 (br s, 3H), 4.12 (m, 1H), 3.75 (m, 1H), 3.68 (m, 1H), 3.19 (d, 1H, J=11.4 Hz), 3.03 (s, 3H), 2.52 (t, 1H, J=12.0 Hz), 1.71 (d, 1H, J=10.8 Hz), 1.65 (d, 1H, J=11.4 Hz), 1.25 (m, 20H), 1.13 (m, 2H), 0.93 (m, 1H), 0.87 (t, 3H, J=7.2 Hz), 0.71 (q, 1H, J=12.0 Hz). $^{13}$C NMR (150 MHz, $CDCl_3$): δ 173.6, 148.4, 139.3, 127.2 (2C), 127.0 (2C), 71.8, 62.5, 59.8, 56.0, 44.9, 44.4, 36.8, 36.4, 35.3, 31.9, 31.3, 29.7 (5C), 29.3, 26.4, 22.7, 14.1.

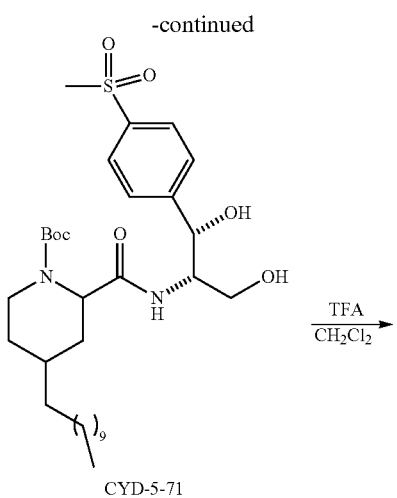

CYD-5-71

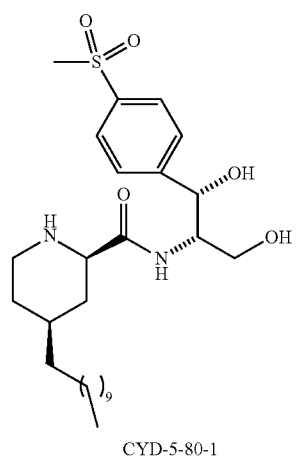

CYD-5-80-1

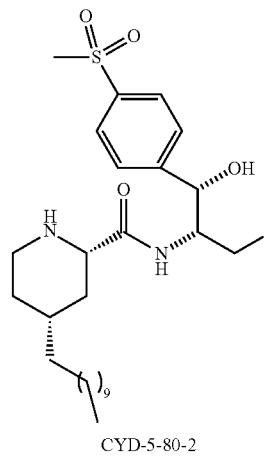

CYD-5-80-2

(2S,4R)—N-((1R,2R)-1,3-dihydroxy-1-phenylpropan-2-yl)-4-phenethylpiperidine-2-carboxamide (CYD-5-100-1) and (2R,4S)—N-((1R,2R)-1,3-dihydroxy-1-phenylpropan-2-yl)-4-phenethylpiperidine-2-carboxamide (CYD-5-100-2)

To a solution of CYD-3-46 (170 mg, 0.51 mmol) and (1R,2R)-(−)-2-amino-1-phenyl-1,3-propanediol (85 mg, 0.51 mmol) in 6 mL of CH₂Cl₂ was added HBTU (251 mg, 0.66 mmol) and DIPEA (165 mg, 1.27 mmol). The resulting mixture was stirred at room temperature for 4 h. After that, TLC showed that the starting material disappeared. The reaction mixture was partitioned between CH₂Cl₂ (50 ml) and 10% citric aqueous solution (10 mL). The organic layer was separated and washed with saturated aqueous NaHCO₃ (10 mL). After drying over anhydrous Na₂SO₄, the solvent was removed under vacuum to give an oily residue. This residue was purified with silica gel column; eluting with 2.5% MeOH in CH₂Cl₂ afforded the amide CYD-5-95 (160 mg, 65%). The amide CYD-5-95 (160 mg, 0.33 mmol) was then dissolved in CH₂Cl₂ (4 mL), followed by the addition of TFA (1 mL). The resulting mixture was stirred at room temperature. After 2 h, TLC showed the starting material disappeared. The solvent was removed under vacuum to give an oily residue. The residue was partitioned between CH₂Cl₂ (30 mL) and saturated NaHCO₃ aqueous solution (10 mL). The organic layer was dried over anhydrous Na₂SO₄, filtered and concentrated to give an oil residue. This residue was purified with silica gel column; eluting with 3% MeOH in CH₂Cl₂ afforded CYD-5-100-1 (45 mg, 35%) and CYD-5-100-2 (50 mg, 39%) as a colorless gel, respectively.

CYD-5-100-1: $^1$H NMR (600 MHz, CDCl$_3$) δ 7.54 (br s, 1H), 7.39 (d, 2H, J=7.2 Hz), 7.32 (m, 2H), 7.26 (m, 3H), 7.17 (m, 3H), 4.91 (d, 1H), 4.12 (dd, 1H, J=5.4 Hz), 3.64 (dd, 1H, J=5.4 Hz), 3.51 (dd, 1H, J=5.4 Hz), 3.48 (m, 1H), 3.25 (m, 1H), 2.76 (m, 1H), 2.63 (t, 2H, J=7.8 Hz), 2.08 (d, 1H, J=12.6 Hz), 1.85 (d, 1H, J=13.8 Hz), 1.26 (m, 1H), 1.16 (q, 1H, J=12.6 Hz). $^{13}$C NMR (150 MHz, CDCl$_3$): δ 171.6, 141.8, 141.5, 128.2, 128.1 (3C), 127.5, 126.1 (2C), 125.7, 72.1, 61.4, 58.9, 57.0, 48.0, 44.1, 38.0, 34.7, 34.2, 32.4, 29.6.

CYD-5-100-2: $^1$H NMR (600 MHz, CDCl$_3$) δ 7.74 (br s, 1H), 7.32 (d, 2H, J=7.8 Hz), 7.24 (m, 4H), 7.14 (m, 4H), 5.04 (br s, 2H), 4.97 (s, 1H), 4.12 (s, 1H), 3.77 (m, 1H), 3.70 (m, 1H), 3.38 (s, 2H), 3.34 (m, 1H), 3.02 (d, 1H, J=9.6 Hz), 2.50 (m, 3H), 1.72 (d, 1H, J=10.2 Hz), 1.61 (d, 1H, J=10.2 Hz), 1.39 (m, 2H), 1.01 (m, 1H), 0.81 (m, 1H). $^{13}$C NMR (150 MHz, CDCl$_3$): δ 172.2, 142.0, 141.6, 128.4 (2C), 128.2 (2C), 127.4, 125.9 (3C), 72.6, 62.7, 59.1, 56.6, 50.4, 44.2, 38.2, 35.1, 34.3, 32.5, 30.2.

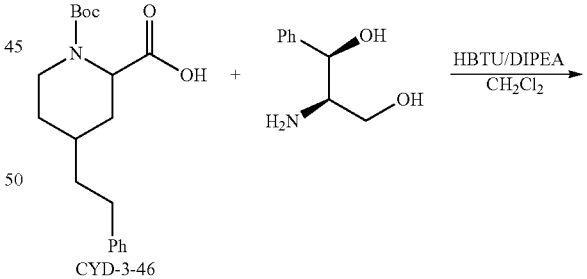

CYD-3-46

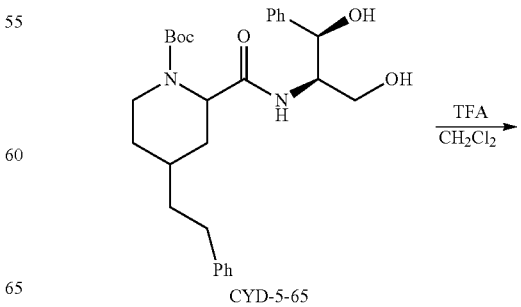

CYD-5-65

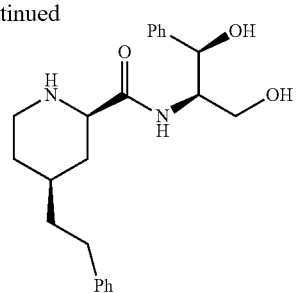

CYD-5-100-2

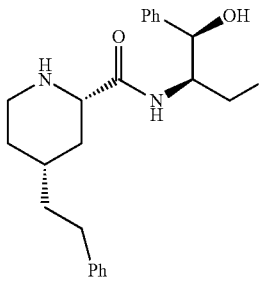

CYD-5-100-1

(2S,4R)-4-(2-cyclohexylethyl)-N-((1R,2R)-1,3-dihydroxy-1-phenylpropan-2-yl)piperidine-2-carboxamide (CYD-6-1-1) and (2R,4S)-4-(2-cyclohexylethyl)-N-((1R,2R)-1,3-dihydroxy-1-phenylpropan-2-yl)piperidine-2-carboxamide (CYD-6-1-2)

To a solution of CYD-3-51 (176 mg, 0.52 mmol) and (1R,2R)-(−)-2-amino-1-phenyl-1,3-propanediol (87 mg, 0.52 mmol) in 6 mL of $CH_2Cl_2$ was added HBTU (255 mg, 0.67 mmol) and DIPEA (167 mg, 1.29 mmol). The resulting mixture was stirred at room temperature for 4 h. After that, TLC showed that the starting material disappeared. The reaction mixture was partitioned between $CH_2Cl_2$ (50 ml) and 10% citric aqueous solution (10 mL). The organic layer was separated and washed with saturated aqueous $NaHCO_3$ (10 mL). After drying over anhydrous $Na_2SO_4$, the solvent was removed under vacuum to give an oily residue. This residue was purified with silica gel column; eluting with 2.5% MeOH in $CH_2Cl_2$ afforded the amide CYD-5-97 (180 mg, 70%). The amide CYD-5-97 (150 mg, 0.30 mmol) was then dissolved in $CH_2Cl_2$ (4 mL), followed by the addition of TFA (1 mL). The resulting mixture was stirred at rt. After 2 h, TLC showed the starting material disappeared. The solvent was removed under vacuum to give an oily residue, which was partitioned between $CH_2Cl_2$ (30 mL) and saturated $NaHCO_3$ aqueous solution (10 mL). The organic layer was dried over anhydrous $Na_2SO_4$, filtered and concentrated to give an oily residue. This residue was purified with silica gel column; eluting with 3% MeOH in $CH_2Cl_2$ afforded CYD-6-1-1 (50 mg, 42%) and CYD-6-1-2 (53 mg, 44%) as a colorless gel, respectively.

CYD-6-1-1: $^1$H NMR (600 MHz, $CDCl_3+CD_3OD$) δ 7.69 (br s, 1H), 7.39 (d, 2H, J=7.8 Hz), 7.31 (t, 2H, J=7.8 Hz), 7.23 (t, 1H, J=7.8 Hz), 4.97 (d, 1H, J=4.2 Hz), 4.09 (m, 1H), 3.70 (m, 1H), 3.5 (m, 1H), 3.15 (dd, 1H, J=2.4 Hz, 12.0 Hz), 3.11 (d, 1H, J=12.0 Hz), 2.63 (m, 1H), 1.80 (m, 1H), 1.69 (m, 7H), 1.20 (m, 10H), 0.89 (m, 1H), 0.82 (q, 1H, J=12.6 Hz). $^{13}$C NMR (150 MHz, $CDCl_3$): δ 174.5, 141.9, 127.9 (2C), 127.2, 125.9 (2C), 71.5, 61.5, 60.1, 56.2, 45.0, 37.7, 36.3, 35.8, 33.9, 33.2 (2C), 31.7, 29.3, 26.5, 26.2 (2C).

CYD-6-1-2: $^1$H NMR (600 MHz, $CDCl_3$) δ 7.77 (d, 1H, J=6.0 Hz), 7.32 (d, 2H, J=7.2 Hz), 7.26 (m, 2H), 7.19 (t, 1H, J=7.2 Hz), 5.50 (br s, 2H), 4.97 (d, 1H), 4.12 (d, 1H, J=3.0 Hz), 3.74 (m, 2H), 3.39 (d, 1H, J=11.4 Hz), 3.03 (d, 1H, J=9.0 Hz), 2.50 (m, 1H), 1.69 (m, 6H), 1.58 (d, 1H, J=9.6 Hz), 1.19 (m, 10H), 0.97 (m, 1H), 0.86 (m, 2H), 0.74 (q, 1H, J=12.0 Hz). $^{13}$C NMR (150 MHz, $CDCl_3$): δ 172.3, 141.5, 128.1 (2C), 127.3, 125.8 (2C), 72.6, 62.7, 59.2, 56.5, 44.3, 37.8, 35.2, 34.9, 34.0, 33.7, 33.4 (2C), 30.3, 26.7, 26.4 (2C).

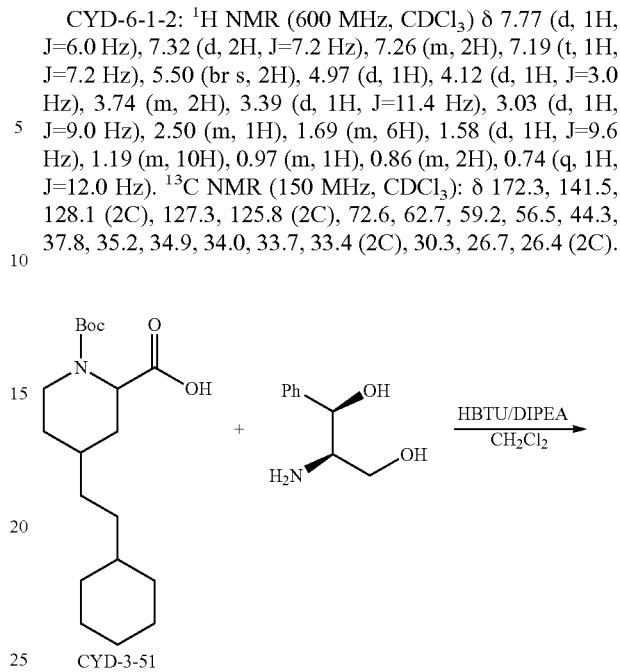

CYD-3-51

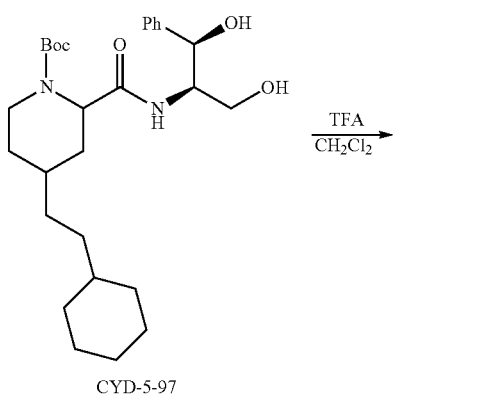

CYD-5-97

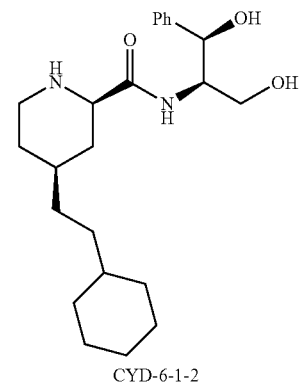

CYD-6-1-2

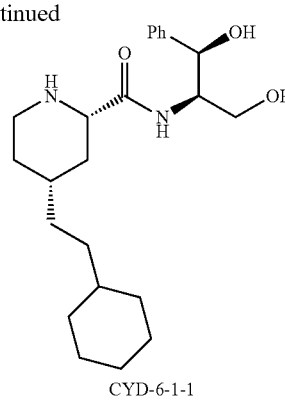

CYD-6-1-1

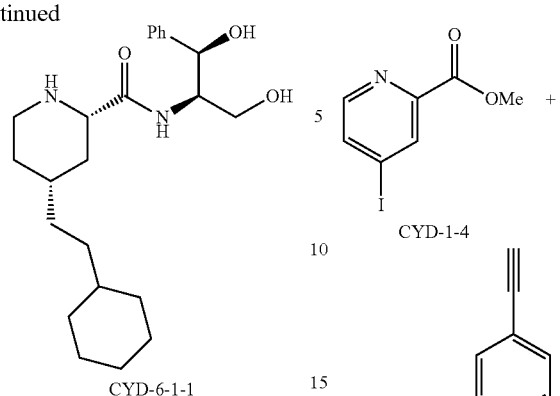

CYD-1-4

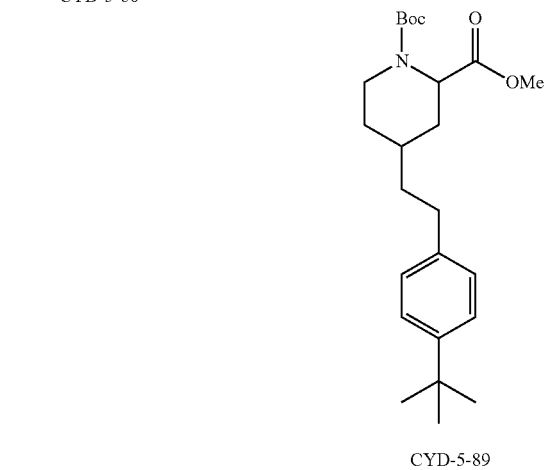

CYD-5-86

4-[2-(4-tert-Butyl-phenyl)-ethyl]-piperidine-1,2-dicarboxylic acid 1-tert-butyl ester 2-methyl ester (CYD-5-89)

To a dried flask was added CYD-1-4 (600 mg, 2.2 mmol, 1 equiv.), triphenylphosphine (60 mg, 0.22 mmol, 0.1 equiv.), copper (I) iodide (43 g, 0.22 mmol, 0.1 equiv.), palladium acetate (25 mg, 0.11 mmol, 0.05 equiv.) and triethylamine (8 mL). The mixture was degassed with nitrogen, followed by addition of 4-tert-butylphenylacetylene (721 mg, 4.56 mmol, 2.0 equiv.). The reaction mixture was stirred at room temperature for 12 h. The insoluble solid was filtered and the filtrate was concentrated under the vacuum, and the brown residue was purified with silica gel chromatography; eluting with 1:3 ethyl acetate-hexane provided the desired product CYD-5-86 as a brown oil (750 mg, 82%). To a solution of CYD-5-86 (500 mg, 1.7 mmol) in a mixture of MeOH (9 mL), water (6 mL) and 37% hydrochloric acid (160 μL) was added platinum oxide (193 mg, 0.85 mmol). The reaction mixture was purged and charged with hydrogen (55 psi) for 3 hrs. The platinum oxide was removed by filtration and the filtrate was concentrated to give an oily residue. The residue was diluted with $CH_2Cl_2$ and washed with the saturated $NaHCO_3$ aqueous solution. After drying over anhydrous $Na_2SO_4$, the solvent was removed under vacuum to give a colorless oil residue. $^1H$ NMR indicated that the residue was a mixture of two products. To a solution of the residue (500 mg) in methanol (10 mL) was added $Et_3N$ (345 mg, 3.4 mmol) and $(Boc)_2O$ (445 mg, 2.04 mmol). The mixture was stirred at room temperature overnight. The solvent was removed under vacuum to give an oily residue. The residue was purified with silica gel column; eluting with 5:1 hexane-ethyl acetate gave the Boc-protected product CYD-5-89 (600 mg, 87%) as a colorless gel. $^1H$ NMR (600 MHz, $CDCl_3$) δ 7.28 (d, 2H, J=8.4 Hz), 7.07 (d, 2H, J=8.4 Hz), 4.34 (m, 1H), 3.70 (s, 3H), 3.57 (m, 1H), 3.37 (m, 1H), 2.57 (m, 2H), 1.99 (m, 1H), 1.88 (m, 1H), 1.76 (m, 1H), 1.66 (m, 1H), 1.56 (m, 2H), 1.43 (m, 10H), 1.30 (m, 9H). $^{13}C$ NMR (150 MHz, $CDCl_3$): δ 173.3, 155.7, 148.5, 138.9, 127.9 (2C), 125.2 (2C), 80.6, 54.3, 51.9, 35.1, 34.3, 32.8, 31.4 (2C), 30.9, 30.8, 29.3, 28.3 (2C), 27.4.

(2S,4R)-4-(4-(tert-butyl)phenethyl)-N-((1R,2R)-1,3-dihydroxy-1-phenylpropan-2-yl)piperidine-2-carboxamide (CYD-6-2-1) and (2R,4S)-4-(4-(tert-butyl)phenethyl)-N-((1R,2R)-1,3-dihydroxy-1-phenylpropan-2-yl)piperidine-2-carboxamide (CYD-6-2-2)

To a solution of CYD-5-89 (600 mg, 1.47 mmol) in 12 mL of THF and 4 mL of water was added lithium hydroxide monohydrate (275 mg, 2.0 mmol). The mixture was stirred at room temperature for 72 h. THF was removed under vacuum. The aqueous layer was taken up in ethyl acetate, and partitioned with 10% NaHSO$_4$ aqueous solution. The organic layer was washed with water and brine, and then dried over anhydrous Na$_2$SO$_4$ and concentrated under vacuum to give the desired product CYD-5-99 (550 mg, 95%) as a colorless oil. To a solution of CYD-5-99 (200 mg, 0.51 mmol) and (1R,2R)-(–)-2-amino-1-phenyl-1,3-propanediol (86 mg, 0.51 mmol) in 6 mL of CH$_2$Cl$_2$ was added HBTU (253 mg, 0.66 mmol) and DIPEA (165 mg, 1.28 mmol). The resulting mixture was stirred at room temperature for 4 h. After that, TLC showed that the starting material disappeared. The reaction mixture was partitioned between CH$_2$Cl$_2$ (50 mL) and 10% citric aqueous solution (10 mL). The organic layer was separated and washed with saturated aqueous NaHCO$_3$ (10 mL). After drying over anhydrous Na$_2$SO$_4$, the solvent was removed under vacuum to give an oily residue. This residue was purified with silica gel column; eluting with 3% MeOH in CH$_2$Cl$_2$ afforded the amide CYD-5-98 (220 mg, 79%). The amide CYD-5-98 (170 mg, 0.31 mmol) was then dissolved in CH$_2$Cl$_2$ (4 mL), followed by the addition of TFA (1 mL). The resulting mixture was stirred at room temperature. After 2 h, and TLC showed the starting material disappeared. The solvent was removed under vacuum to give an oily residue, which was partitioned between CH$_2$Cl$_2$ (30 mL) and saturated NaHCO$_3$ aqueous solution (10 mL). The organic layer was dried over anhydrous Na$_2$SO$_4$, filtered and concentrated to give an oily residue. This residue was purified with silica gel column; eluting with 10% MeOH in CH$_2$Cl$_2$ afforded CYD-6-2-1 (40 mg, 28%) and CYD-6-2-2 (50 mg, 36%) as a colorless gel, respectively.

CYD-6-2-1: $^1$H NMR (600 MHz, CDCl$_3$+CD$_3$OD) δ 7.46 (br s, 1H), 7.39 (d, 2H, J=7.2 Hz), 7.31 (m, 4H), 7.24 (t, 1H, J=7.2 Hz), 7.10 (d, 1H, J=8.4 Hz), 4.96 (d, 1H, J=4.8 Hz), 4.09 (q, 1H, J=5.4 Hz), 3.68 (m, 1H), 3.57 (m, 1H), 3.21 (dd, 1H, J=3.0 Hz, 12.0 Hz), 3.12 (m, 1H), 2.63 (m, 1H), 2.57 (t, 2H, J=7.8 Hz), 1.91 (d, 1H, J=13.2 Hz), 1.76 (d, 1H, J=12.6 Hz), 1.54 (m, 2H), 1.46 (m, 1H), 1.30 (s, 9H), 1.12 (qd, 1H, J=3.6 Hz, 12.0 Hz), 0.91 (q, 1H, J=12.6 Hz). $^{13}$C NMR (150 MHz, CDCl$_3$+CD$_3$OD): δ 174.0, 148.5, 141.6, 139.0, 128.1 (2C), 127.8 (2C), 127.4, 126.0, 125.9, 125.1 (2C), 72.0, 61.8, 59.9, 56.6, 44.9, 38.5, 35.8, 34.9, 34.2, 31.9, 31.3, 31.1 (3C).

CYD-6-2-2: $^1$H NMR (600 MHz, CDCl$_3$+CD$_3$OD) δ 7.68 (br s, 1H), 7.38 (d, 2H, J=7.8 Hz), 7.31 (m, 4H), 7.22 (t, 1H, J=7.2 Hz), 7.11 (d, 2H, J=8.4 Hz), 4.99 (d, 1H, J=4.2 Hz), 4.11 (m, 1H), 3.75 (m, 1H), 3.66 (m, 1H), 3.47 (dd, 1H, J=2.4 Hz, 12.6 Hz), 3.20 (d, 1H, J=11.4 Hz), 2.72 (m, 1H), 2.56 (m, 2H), 1.87 (d, 1H, J=13.2 Hz), 1.78 (d, 1H, J=13.8 Hz), 1.52 (m, 3H), 1.31 (s, 9H), 1.18 (m, 1H), 0.96 (q, 1H, J=12.0 Hz). $^{13}$C NMR (150 MHz, CDCl$_3$+CD$_3$OD): δ 171.7, 148.7, 141.5, 138.8, 128.1 (2C), 127.8 (2C), 127.4, 125.9 (2C), 125.2 (2C), 72.4, 62.3, 59.0, 56.6, 44.2, 38.2, 34.8, 34.2, 31.9, 31.3 (4C), 30.1.

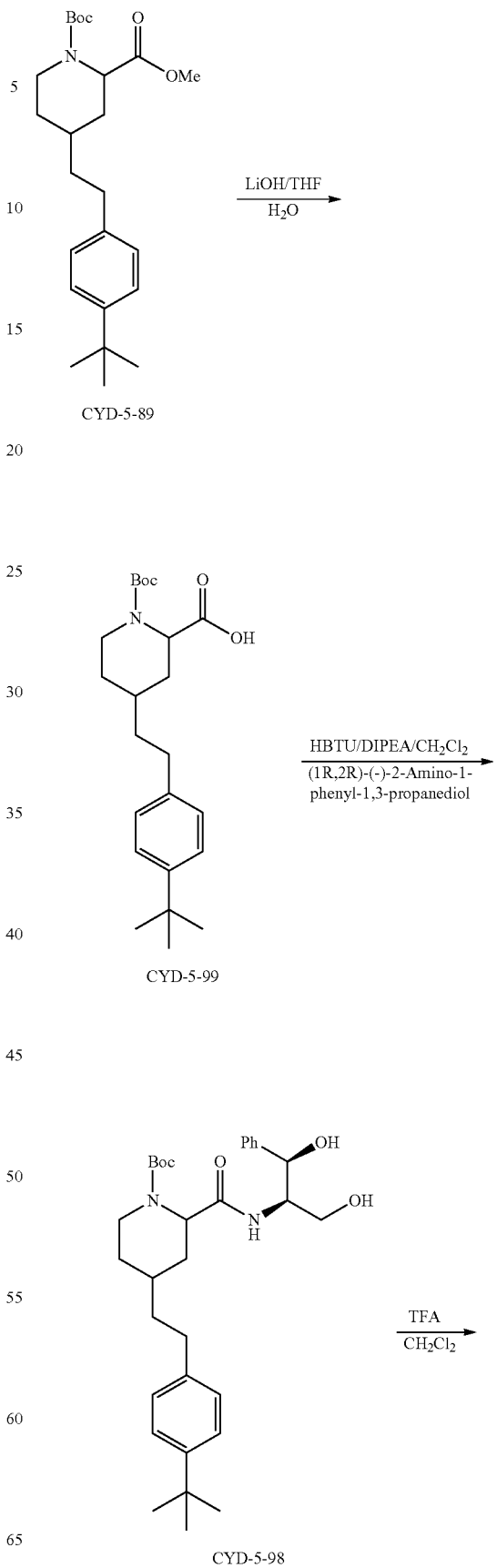

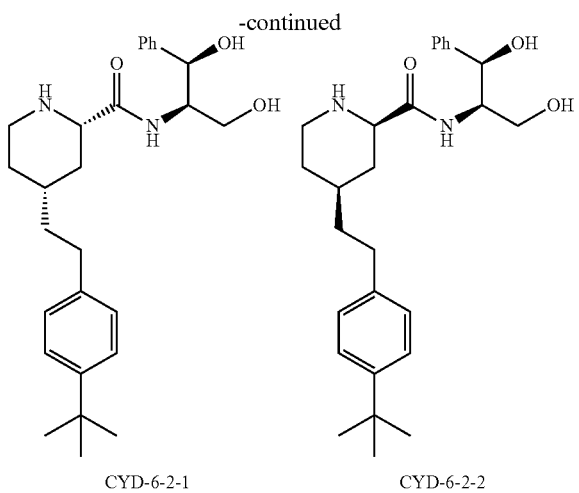

1H), 2.50 (m, 2H), 2.06 (s, 3H), 2.02 (m, 1H), 1.84 (m, 2H), 1.60 (m, 3H), 1.42 (s, 9H), 1.40 (m, 1H). $^{13}$C NMR (150 MHz, CDCl$_3$): δ 173.5, 155.8, 80.1, 54.5, 51.9, 39.3, 37.5, 35.4, 35.3, 34.9, 33.3, 32.8, 31.7 (2C), 31.5, 31.3, 30.8 (2C), 30.1, 29.3, 28.8, 28.7, 28.3, 22.7, 20.2.

4-[2-(4-Methyl-cyclohexyl)-ethyl]-piperidine-1,2-dicarboxylic acid 1-tert-butyl ester 2-methyl ester (CYD-5-96-1) and 4-(2-p-Tolyl-ethyl)-piperidine-1,2-dicarboxylic acid 1-tert-butyl ester 2-methyl ester (CYD-5-96-2)

To a dried flask was added CYD-1-4 (600 mg, 2.2 mmol, 1 equiv.), triphenylphosphine (60 mg, 0.22 mmol, 0.1 equiv.), copper (I) iodide (43 g, 0.22 mmol, 0.1 equiv), palladium acetate (25 mg, 0.11 mmol, 0.05 equiv) and triethylamine (8 mL). The mixture was degassed with nitrogen, followed by addition of 4-methylphenylacetylene (529 mg, 4.56 mmol, 2.0 equiv). The reaction mixture was stirred at room temperature for 3 h. The insoluble solid was filtered and the filtrate was concentrated under the vacuum, and the dark residue was purified with silica gel chromatography; eluting with 1:3 ethyl acetate-hexane provided the desired product CYD-5-90 as a brown oil (560 mg, 97%). To a solution of CYD-5-90 (550 mg, 2.19 mmol) in a mixture of MeOH (12 mL), water (4 mL) and 37% hydrochloric acid (181 μL) was added platinum oxide (248 mg, 1.09 mmol). The reaction mixture was purged and charged with hydrogen (55 psi) for 18 h. The platinum oxide was removed by filtration and the filtrate was concentrated to give an oily residue. The residue was diluted with CH$_2$Cl$_2$ and washed with the saturated NaHCO$_3$ aqueous solution. After drying over anhydrous Na$_2$SO$_4$, the solvent was removed under vacuum to give a colorless oily residue. $^1$H NMR indicated that the residue was a mixture of two products. To a solution of the residue (572 mg) in methanol (20 mL) was added Et$_3$N (445 mg, 4.38 mmol) and (Boc)$_2$O (573 mg, 2.62 mmol). The mixture was stirred at room temperature overnight. The solvent was removed under vacuum to give an oily residue. The residue was purified with silica gel column; eluting with 5:1 hexane-ethyl acetate gave the Boc-protected product CYD-5-96-1 (240 mg, 28%) and CYD-5-96-2 (280 mg, 34%) as a colorless gel, respectively. CYD-5-96-1: $^1$H NMR (600 MHz, CDCl$_3$) δ 4.30 (m, 1H), 3.71 (s, 3H), 3.55 (br s, 1H), 3.36 (br s, 1H), 1.97 (m, 1H), 1.80 (m, 2H), 1.66 (m, 1H), 1.57 (m, 1H), 1.52 (s, 3H), 1.45 (m, 11H), 1.37 (m, 3H), 1.25 (m, 5H), 1.15 (m, 1H), 0.89 (d, 3H, J=6.6 Hz), 0.86 (m, 4H). $^{13}$C NMR (150 MHz, CDCl$_3$): δ 173.4, 155.8, 80.0, 54.4, 51.8, 38.4, 37.5, 35.2, 34.9, 33.3, 32.8, 31.6, 31.4, 31.2, 30.7, 30.1, 29.3, 28.7, 28.6, 28.2, 27.3, 22.6, 20.1. CYD-5-96-2: $^1$H NMR (600 MHz, CDCl$_3$) δ 7.07 (m, 4H), 4.35 (t, 1H, J=6.6 Hz), 3.73 (s, 3H), 3.58 (m, 1H), 3.40 (m,

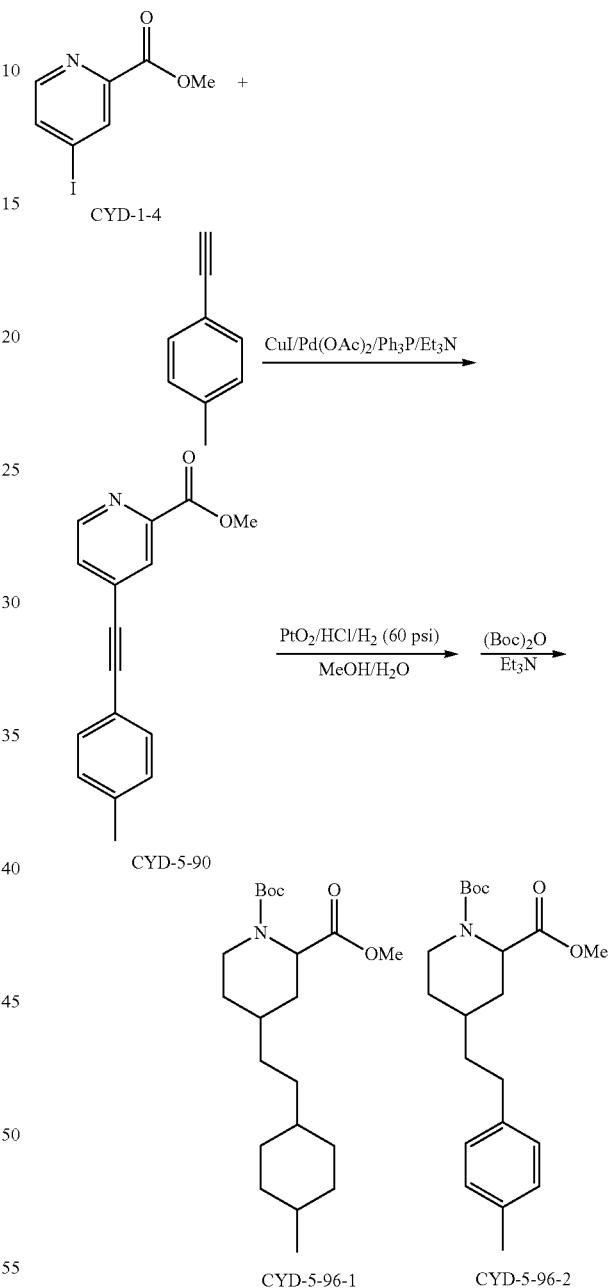

(2S,4S)—N-((1S,2S)-1,3-dihydroxy-1-phenylpropan-2-yl)-4-(4-methylphenethyl)piperidine-2-carboxamide (CYD-6-9-1) and (2S,4R)—N-((1S,2S)-1,3-dihydroxy-1-phenylpropan-2-yl)-4-(4-methylphenethyl) piperidine-2-carboxamide (CYD-6-9-2)

To a solution of CYD-5-96-2 (240 mg, 0.66 mmol) in 3 mL of THF and 1 mL of water was added lithium hydroxide monohydrate (122 mg, 2.92 mmol). The mixture was stirred at room temperature for 72 h. THF was removed under vacuum. The aqueous layer was taken up in ethyl acetate, and partitioned with 10% NaHSO₄ aqueous solution. The organic layer was washed with water and brine, and then dried over anhydrous Na₂SO₄ and concentrated under vacuum to give the desired product CYD-6-4 as a colorless oil. To a solution of CYD-6-4 (190 mg, 0.54 mmol) and (1S,2S)-(+)-2-amino-1-phenyl-1,3-propanediol (91 mg, 0.54 mmol) in 6 mL of CH₂Cl₂ was added HBTU (253 mg, 0.66 mmol) and DIPEA (165 mg, 1.28 mmol). The resulting mixture was stirred at room temperature for 4 h. After that, TLC showed that the starting material disappeared. The reaction mixture was partitioned between CH₂Cl₂ (50 ml) and 10% citric aqueous solution (10 mL). The organic layer was separated and washed with saturated aqueous NaHCO₃ (10 mL). After drying over anhydrous Na₂SO₄, the solvent was removed under vacuum to give an oil residue. This residue was purified with silica gel column; eluting with 3% MeOH in CH₂Cl₂ afforded the amide CYD-6-7 (200 mg, 73%). The amide CYD-6-7 (180 mg, 0.36 mmol) was then dissolved in CH₂Cl₂ (4 mL), followed by TFA (1 mL). The resulting mixture was stirred at room temperature. After 2 h, and TLC showed the starting material disappeared. The solvent was removed under vacuum to give an oily residue. The residue was partitioned between CH₂Cl₂ (30 mL) and saturated NaHCO₃ aqueous solution (10 mL). The organic layer was dried over anhydrous Na₂SO₄, filtered and concentrated to give an oily residue. This residue was purified with silica gel column; eluting with 10% MeOH in CH₂Cl₂ afforded CYD-6-9-1 (50 mg, 34%) and CYD-6-9-2 (53 mg, 37%) as a colorless gel, respectively.

CYD-6-9-1: ¹H NMR (600 MHz, CDCl₃+CD₃OD) δ 7.46 (br s, 1H), 7.39 (d, 2H, J=7.8 Hz), 7.31 (t, 2H, J=7.8 Hz), 7.25 (t, 1H, J=7.2 Hz), 7.09 (d, 2H, J=8.4 Hz), 7.05 (d, 2H, J=7.8 Hz), 4.97 (d, 1H, J=4.2 Hz), 4.08 (d, 1H, J=4.8 Hz), 3.69 (m, 1H), 3.58 (m, 1H), 3.15 (dd, 1H, J=3.0 Hz, 12.0 Hz), 3.11 (m, 1H), 2.60 (m, 1H), 2.55 (t, 2H, J=7.8 Hz), 2.31 (s, 3H), 1.86 (d, 1H, J=13.2 Hz), 1.73 (d, 1H, J=13.2 Hz), 1.50 (m, 2H), 1.42 (m, 1H), 1.09 (dq, 1H, J=4.2 Hz, 12.6 Hz), 0.86 (q, 1H, J=12.0 Hz). ¹³C NMR (150 MHz, CDCl₃+CD₃OD): δ 174.3, 141.6, 139.1, 135.1, 128.9 (2C), 128.1 (2C), 128.0 (2C), 127.4, 126.0 (2C), 72.0, 61.9, 60.0, 56.5, 45.0, 38.6, 36.0, 35.0, 32.0, 31.5, 20.6.

CYD-6-9-2: ¹H NMR (600 MHz, CDCl₃) δ 7.45 (d, 1H, J=8.4 Hz), 7.35 (d, 2H, J=7.2 Hz), 7.25 (m, 2H), 7.18 (t, 1H, J=7.2 Hz), 7.08 (d, 2H, J=7.8 Hz), 7.02 (d, 1H, J=8.4 Hz), 5.02 (d, 1H, J=3.0 Hz), 4.65 (br s, 3H), 4.10 (m, 1H), 3.78 (m, 1H), 3.71 (m, 1H), 3.13 (d, 1H, J=13.8 Hz), 2.94 (d, 1H, J=12.0 Hz), 2.48 (t, 2H, J=7.8 Hz), 2.41 (m, 1H), 2.31 (s, 3H), 1.74 (d, 1H, J=12.0 Hz), 1.59 (d, 1H, J=12.0 Hz), 1.39 (m, 2H), 1.31 (m, 1H), 0.90 (m, 1H), 0.78 (q, 1H, J=12.6 Hz). ¹³C NMR (150 MHz, CDCl₃): δ 173.5, 141.8, 139.1, 135.2, 129.1 (3C), 128.1 (3C), 127.4, 125.9 (2C), 72.7, 62.9, 59.8, 56.4, 44.7, 38.7, 36.1, 34.8, 32.1, 31.5, 21.0.

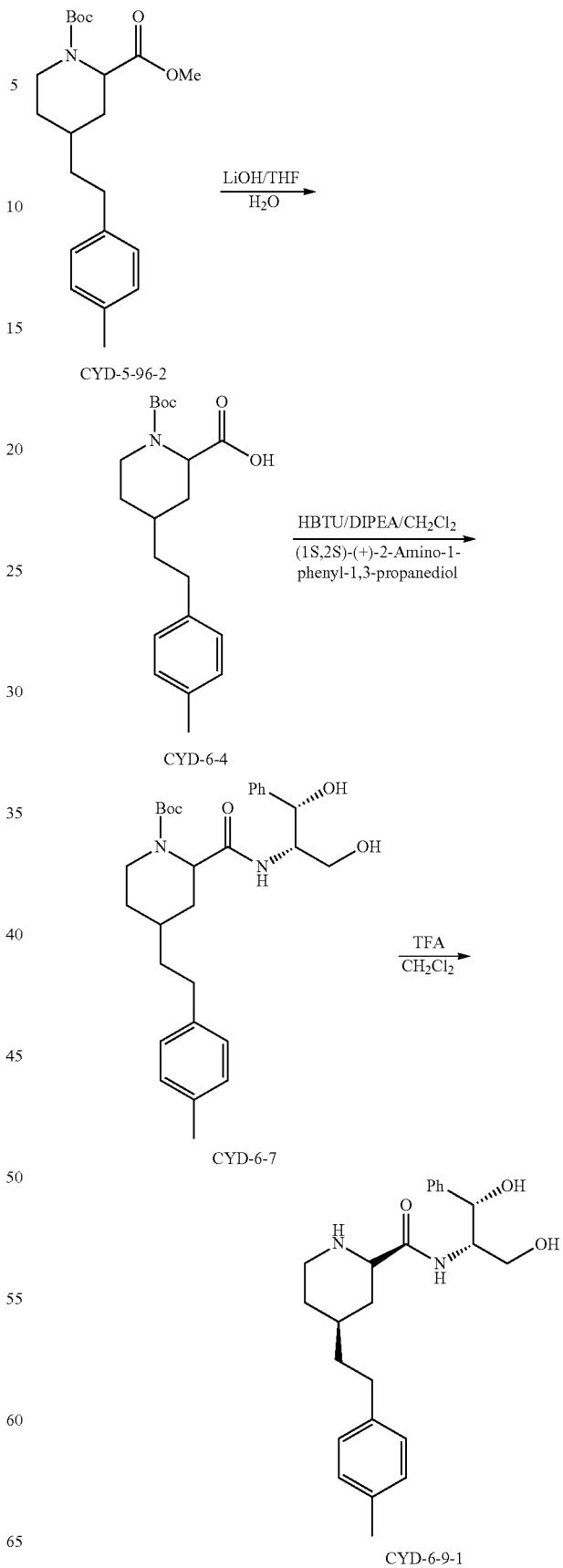

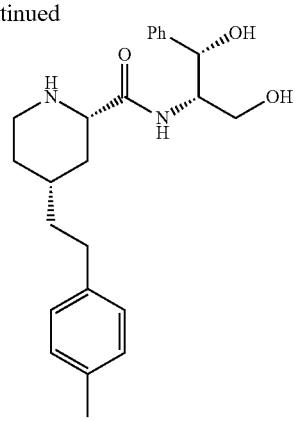

CYD-6-9-2

(2S,4S)—N-((1S,2S)-1,3-dihydroxy-1-phenylpropan-2-yl)-4-(2-(4-methylcyclohexyl)ethyl)piperidine-2-carboxamide (CYD-6-10-1) and (2S,4R)—N-((1R,2S)-1,3-dihydroxy-1-phenylpropan-2-yl)-4-(2-(4-methylcyclohexyl)ethyl)piperidine-2-carboxamide (CYD-6-10-2)

To a solution of CYD-5-96-1 (280 mg, 0.76 mmol) in 3 mL of THF and 1 mL of water was added lithium hydroxide monohydrate (140 mg, 3.35 mmol). The mixture was stirred at room temperature for 72 h. THF was removed under vacuum. The aqueous layer was taken up in ethyl acetate, and partitioned with 10% $NaHSO_4$ aqueous solution. The organic layer was washed with water and brine, and then dried over anhydrous $Na_2SO_4$ and concentrated under vacuum to give the desired product CYD-6-3 as a colorless oil. To a solution of CYD-6-3 (136 mg, 0.38 mmol) and (1S,2S)-(+)-2-amino-1-phenyl-1,3-propanediol (67 mg, 0.40 mmol) in 6 mL of $CH_2Cl_2$ was added HBTU (189 mg, 0.49 mmol) and DIPEA (123 mg, 0.96 mmol). The resulting mixture was stirred at room temperature for 4 h. After that, TLC showed that the starting material disappeared. The reaction mixture was partitioned between $CH_2Cl_2$ (50 mL) and 10% citric aqueous solution (10 mL). The organic layer was separated and washed with saturated aqueous $NaHCO_3$ (10 mL). After drying over anhydrous $Na_2SO_4$, the solvent was removed under vacuum to give an oily residue. This residue was purified with silica gel column; eluting with 5% MeOH in $CH_2Cl_2$ afforded the amide CYD-6-8 (120 mg, 62%). The amide CYD-6-8 (120 mg, 0.24 mmol) was then dissolved in $CH_2Cl_2$ (4 mL), followed by TFA (1 mL). The resulting mixture was stirred at room temperature. After 2 h, TLC showed the starting material disappeared. The solvent was removed under vacuum to give an oily residue. The residue was partitioned between $CH_2Cl_2$ (30 mL) and saturated $NaHCO_3$ aqueous solution (10 mL). The organic layer was dried over anhydrous $Na_2SO_4$, filtered and concentrated to give an oily residue. This residue was purified with silica gel column; eluting with 10% MeOH in $CH_2Cl_2$ afforded CYD-6-10-1 (40 mg, 41%) and CYD-6-10-2 (42 mg, 43%) as a colorless gel, respectively.

CYD-6-10-1: $^1$H NMR (300 MHz, $CDCl_3$) δ 7.32 (m, 5H), 4.99 (d, 1H, J=7.2 Hz), 4.08 (m, 1H), 3.70 (m, 1H), 3.62 (m, 1H), 3.34 (m, 1H), 3.09 (m, 2H), 2.61 (m, 1H), 1.46 (m, 4H), 1.27 (m, 13H), 0.89 (m, 3H), 0.76 (q, 1H, J=12.6 Hz). $^{13}$C NMR (75 MHz, $CDCl_3$): δ 175.6, 142.2, 128.5, 127.8, 126.4, 72.4, 62.4, 60.9, 56.9, 45.8, 38.0, 37.0, 36.5, 35.7, 35.1, 34.7, 33.8, 33.7, 33.3, 32.7, 31.1 (2C), 30.7, 29.2, 29.1, 22.8, 20.4.

CYD-6-10-2: $^1$H NMR (600 MHz, $CDCl_3$) δ 7.31 (m, 5H), 7.22 (t, 1H, J=7.2 Hz), 5.03 (d, 1H, J=3.6 Hz), 4.08 (m, 1H), 3.93 (br s, 3H), 3.78 (m, 1H), 3.72 (m, 1H), 3.13 (dd, 1H, J=2.4 Hz, 12.0 Hz), 2.99 (d, 1H, J=10.8 Hz), 2.48 (m, 1H), 1.74 (m, 1H), 1.67 (m, 1H), 1.60 (m, 2H), 1.44 (m, 3H), 1.20 (m, 10H), 0.91 (d, 3H, J=6.6 Hz), 0.87 (m, 2H), 0.78 (q, 1H, J=12.6 Hz). $^{13}$C NMR (150 MHz, $CDCl_3$): δ 174.0, 141.6, 128.2, 127.4, 125.9, 73.1, 63.1, 60.2, 56.4, 50.5, 45.1, 37.5, 36.4, 35.7, 35.3, 34.6, 34.2, 34.0, 33.3, 32.9, 32.0, 30.8, 30.1, 28.7, 22.6, 20.2.

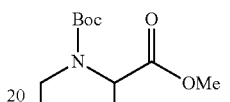

CYD-5-96-1

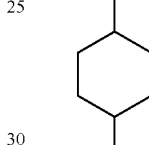

LiOH/THF
$H_2O$

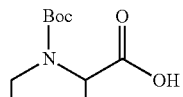

CYD-6-3

HBTU/DIPEA/$CH_2Cl_2$
(1S,2S)-(+)-2-Amino-1-phenyl-1,3-propanediol

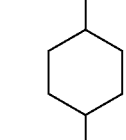

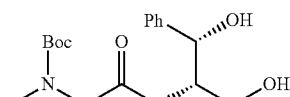

TFA
$CH_2Cl_2$

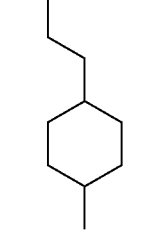

CYD-6-8

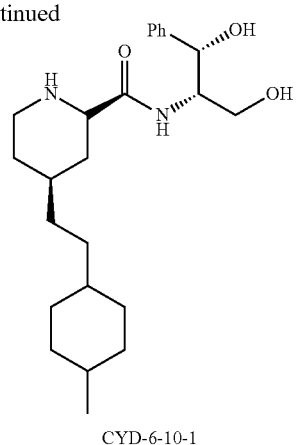

CYD-6-10-1

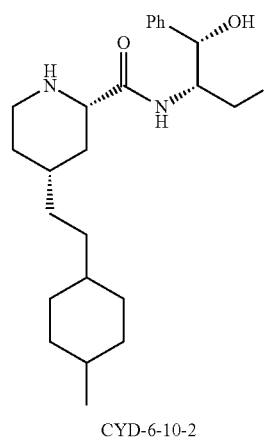

CYD-6-10-2

4-Cyclohexyl-piperidine-1,2-dicarboxylic acid 1-tert-butyl ester 2-methyl ester (CYD-6-6-1) and 4-Phenyl-piperidine-1,2-dicarboxylic acid 1-tert-butyl ester 2-methyl ester (CYD-6-6-2)

To a solution of CYD-1-4 (1000 mg, 3.8 mmol, 1 equiv.) in a mixture of ethanol (50 mL), water (25 mL) and toluene (25 mL) was added $Na_2CO_3$ (1005 mg, 9.5 mmol, 2.5 equiv.), $Pd(PPh_3)_4$ (215 g, 0.38 mmol, 0.05 equiv) and phenyl boronic acid (555 mg, 4.57 mmol, 1.2 equiv.). The reaction mixture was stirred at 80° C. for 12 h. After that, the reaction mixture was concentrated under vacuum to give a solid residue, which was dissolved in water (80 mL) and neutralized with 5% HCl aqueous solution. The mixture was extracted with $CH_2Cl_2$ for five times. The combined organic phases were washed with brine. After drying over anhydrous $Na_2SO_4$, the solvent was removed under vacuum to give an oily residue. To the solution of this residue in methanol was added 50 μL of $H_2SO_4$. The resulting mixture was refluxed at 85° C. for 36 h. After that, the reaction mixture was concentrated under the vacuum, and the dark residue was purified with silica gel chromatography; eluting with 1:3 ethyl acetate-hexane provided the desired product CYD-5-93 as a brown oil (800 mg, 98%). $^1H$ NMR (600 MHz, $CDCl_3$) δ 8.77 (m, 1H), 8.37 (s, 1H), 7.68 (m, 3H), 7.49 (m, 3H), 4.03 (s, 3H). $^{13}C$ NMR (150 MHz, $CDCl_3$): δ 165.8, 150.2, 149.7, 148.4, 137.0, 129.6, 129.2, 127.0, 124.6, 123.1, 53.0. To a solution of CYD-5-93 (210 mg, 0.98 mmol) in a mixture of MeOH (9 mL), water (3 mL) and 37% hydrochloric acid (181 μL) was added platinum oxide (112 mg, 0.49 mmol). The reaction mixture was purged and charged with hydrogen (55 psi) for 16 h. The platinum oxide was removed by filtration and the filtrate was concentrated to give an oily residue. The residue was diluted with $CH_2Cl_2$ and washed with the saturated $NaHCO_3$ aqueous solution. After drying over anhydrous $Na_2SO_4$, the solvent was removed under vacuum to give a colorless oil residue. $^1H$ NMR indicated that the residue was a mixture of two products. To a solution of the residue (215 mg) in dichloromethane (20 mL) was added $Et_3N$ (250 mg, 2.46 mmol) and $(Boc)_2O$ (247 mg, 1.13 mmol). The mixture was stirred at room temperature overnight. The solvent was removed under vacuum to give an oily residue. The residue was purified with silica gel column; eluting with 5:1 hexane-ethyl acetate gave the Boc-protected product CYD-6-6-1 (100 mg, 31%) and CYD-6-6-2 (105 mg, 32%) as colorless gel, respectively.

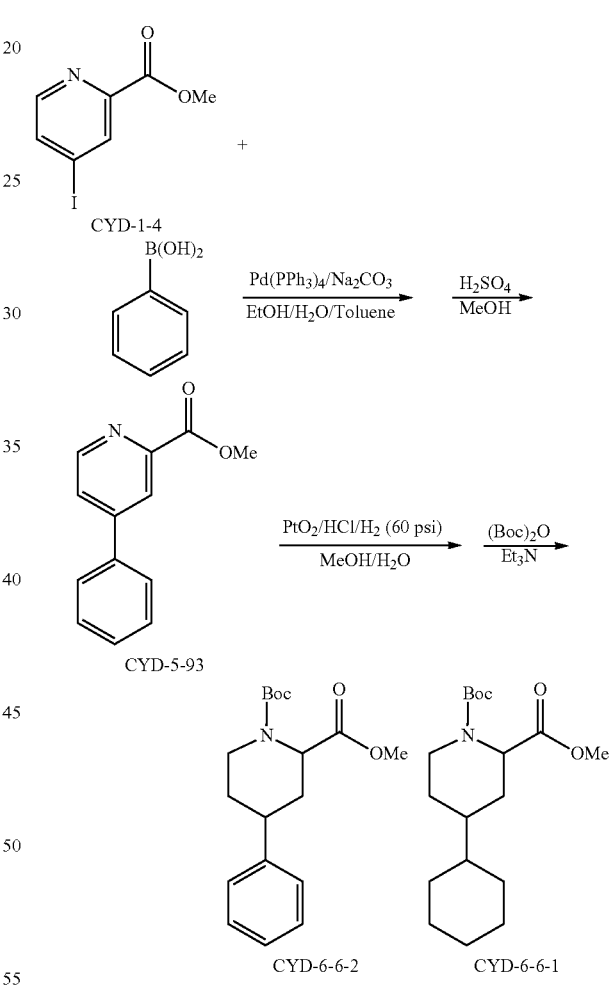

(2S,4S)-4-cyclohexyl-N-((1S,2S)-1,3-dihydroxy-1-phenylpropan-2-yl)piperidine-2-carboxamide (CYD-6-15-1) and (2S,4R)-4-cyclohexyl-N-((1S,2S)-1,3-dihydroxy-1-phenylpropan-2-yl)piperidine-2-carboxamide (CYD-6-15-2)

To a solution of CYD-6-6-1 (360 mg, 1.1 mmol) in 3 mL of THF and 1 mL of water was added lithium hydroxide monohydrate (204 mg, 4.86 mmol). The mixture was stirred at room temperature for 72 h, and then the solvent was removed under vacuum. The aqueous layer was taken up in ethyl acetate, and partitioned with 10% NaHSO₄ aqueous solution. The organic layer was washed with water and brine, and then dried over anhydrous Na₂SO₄ and concentrated under vacuum to give the desired product CYD-6-12 as a colorless oil. To a solution of CYD-6-12 (230 mg, 0.73 mmol) and (1S,2S)-(+)-2-amino-1-phenyl-1,3-propanediol (129 mg, 0.77 mmol) in 6 mL of CH₂Cl₂ was added HBTU (364 mg, 0.96 mmol) and DIPEA (238 mg, 1.8 mmol). The resulting mixture was stirred at room temperature for 4 hrs. After that, TLC showed that the starting material disappeared. The reaction mixture was partitioned between CH₂Cl₂ (50 ml) and 10% citric aqueous solution (10 mL). The organic layer was separated and washed with saturated aqueous NaHCO₃ (10 mL). After drying over anhydrous Na₂SO₄, the solvent was removed under vacuum to give an oily residue. This residue was purified with silica gel column; eluting with 3% MeOH in CH₂Cl₂ afforded the amide CYD-6-13 (220 mg, 64%). The amide CYD-6-13 (220 mg, 0.47 mmol) was then dissolved in CH₂Cl₂ (4 mL), followed by TFA (1 mL). The resulting mixture was stirred at room temperature. After 2 h, TLC showed the starting material disappeared. The solvent was removed under vacuum to give an oily residue. The residue was partitioned between CH₂Cl₂ (30 mL) and saturated NaHCO₃ aqueous solution (10 mL). The organic layer was dried over anhydrous Na₂SO₄, filtered and concentrated to give an oily residue. This residue was purified with silica gel column; eluting with 10% MeOH in CH₂Cl₂ afforded CYD-6-15-1 (70 mg, 40%) and CYD-6-15-2 (74 mg, 43%) as a colorless gel, respectively.

CYD-6-15-1: ¹H NMR (600 MHz, CDCl₃) δ 7.48 (d, 1H, J=8.4 Hz), 7.38 (d, 2H, J=7.2 Hz), 7.28 (m, 2H), 7.22 (t, 1H, J=7.8 Hz), 4.98 (d, 1H, J=4.8 Hz), 4.30 (br s, 3H), 4.08 (m, 1H), 3.70 (m, 1H), 3.62 (m, 1H), 3.11 (dd, 1H, J=2.4 Hz, 12.0 Hz), 2.97 (m, 1H), 2.46 (m, 1H), 1.72 (m, 2H), 1.59 (m, 4H), 1.13 (m, 5H), 0.99 (m, 2H), 0.84 (m, 3H). ¹³C NMR (150 MHz, CDCl₃): δ 174.5, 141.7, 128.2 (2C), 127.4, 126.2 (2C), 72.9, 62.7, 61.0, 56.6, 45.5, 42.7, 41.0, 33.3, 29.8, 28.6 (2C), 26.6, 26.5 (2C).

CYD-6-15-2: ¹H NMR (600 MHz, CDCl₃+CD₃OD) δ 7.48 (s, 1H), 7.37 (d, 2H, J=7.2 Hz), 7.30 (m, 2H), 7.23 (t, 1H, J=7.2 Hz), 4.99 (d, 1H, J=3.6 Hz), 4.10 (m, 1H), 3.72 (m, 1H), 3.62 (m, 1H), 3.13 (m, 2H), 2.58 (dt, 1H, J=3.0 Hz, 12.6 Hz), 1.75 (m, 3H), 1.66 (m, 4H), 1.15 (m, 6H), 0.93 (m, 2H), 0.87 (q, 1H, J=12.0 Hz). ¹³C NMR (150 MHz, CDCl₃): δ 173.9, 141.7, 128.0 (2C), 127.2, 125.8 (2C), 71.9, 62.0, 60.0, 56.3, 45.1, 42.7, 41.0, 33.5, 29.8, 29.7, 28.7, 26.5, 26.4 (2C).

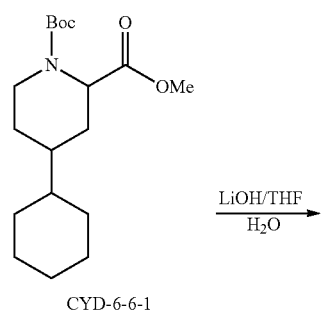

CYD-6-6-1

LiOH/THF
——→
H₂O

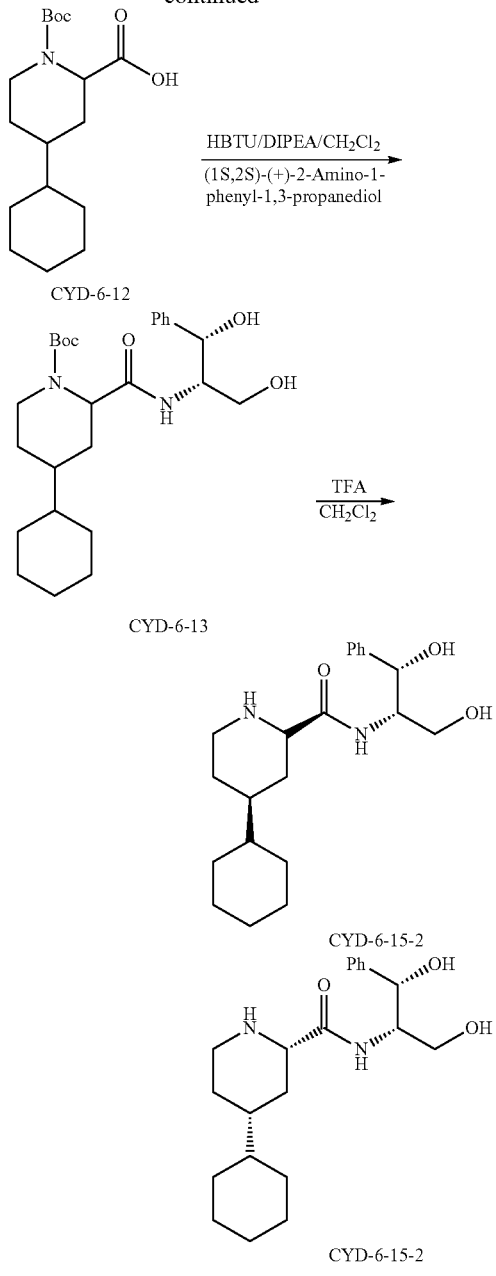

(2S,4S)—N-((1S,2S)-1,3-dihydroxy-1-phenylpropan-2-yl)-4-phenylpiperidine-2-carboxamide (CYD-6-16-1) and (2S,4R)—N-((1S,2S)-1,3-dihydroxy-1-phenylpropan-2-yl)-4-phenylpiperidine-2-carboxamide (CYD-6-16-2)

To a solution of CYD-6-6-2 (105 mg, 0.33 mmol) in 3 mL of THF and 1 mL of water was added lithium hydroxide monohydrate (61 mg, 1.44 mmol). The mixture was stirred at room temperature for 72 h. THF was removed under vacuum. The aqueous layer was taken up in ethyl acetate, and partitioned with 10% NaHSO₄ aqueous solution. The organic layer was washed with water and brine, and then dried over anhydrous Na₂SO₄ and concentrated under vacuum to give the desired product CYD-6-11 as a colorless oil. To a solution of CYD-6-11 (104 mg, 0.34 mmol) and (1S,2S)-(+)-2-amino-1-phenyl-1,3-propanediol (60 mg, 0.35 mmol) in 6 mL of CH$_2$Cl$_2$ was added HBTU (168 mg, 0.44 mmol) and DIPEA (110 mg, 0.85 mmol). The resulting mixture was stirred at room temperature for 4 hrs. After that, TLC showed that the starting material disappeared. The reaction mixture was partitioned between CH$_2$Cl$_2$ (50 ml) and 10% citric aqueous solution (10 mL). The organic layer was separated and washed with saturated aqueous NaHCO$_3$ (10 mL). After drying over anhydrous Na$_2$SO$_4$, the solvent was removed under vacuum to give an oily residue. This residue was purified with silica gel column; eluting with 3% MeOH in CH$_2$Cl$_2$ afforded the amide CYD-6-14 (115 mg, 74%). The amide CYD-6-13 (115 mg, 0.25 mmol) was then dissolved in CH$_2$Cl$_2$ (4 mL), followed by TFA (1 mL). The resulting mixture was stirred at room temperature. After 2 h, TLC showed the starting material disappeared. The solvent was removed under vacuum to give an oily residue. The residue was partitioned between CH$_2$Cl$_2$ (30 mL) and saturated NaHCO$_3$ aqueous solution (10 mL). The organic layer was dried over anhydrous Na$_2$SO$_4$, filtered and concentrated to give an oily residue. This residue was purified with silica gel column; eluting with 10% MeOH in CH$_2$Cl$_2$ afforded CYD-6-16-1 (36 mg, 40%) and CYD-6-16-2 (38 mg, 43%) as a colorless gel, respectively.

CYD-6-16-1: $^1$H NMR (600 MHz, CDCl$_3$) δ 7.42 (m, 2H), 7.30 (m, 4H), 7.22 (m, 2H), 7.12 (d, 2H, J=7.2 Hz), 5.06 (d, 1H, J=4.2 Hz), 4.12 (m, 1H), 3.80 (m, 1H), 3.72 (m, 1H), 3.25 (dd, 1H, J=3.0 Hz, 12.0 Hz), 3.10 (d, 1H, J=12.0 Hz), 2.65 (m, 1H), 2.55 (m, 1H), 1.95 (d, 1H, J=12.6 Hz), 1.75 (d, 1H, J=12.6 Hz), 1.75 (m, 1H), 1.28 (q, 1H, J=12.6 Hz). $^{13}$C NMR (150 MHz, CDCl$_3$): δ 174.5, 145.2, 141.4, 128.4, 128.3 (2C), 127.7, 126.7 (2C), 126.4, 126.1 (2C), 125.9, 73.1, 62.9, 61.0, 56.5, 45.7, 42.0, 37.1, 32.9.

CYD-6-16-2: $^1$H NMR (600 MHz, CDCl$_3$) δ 7.56 (d, 1H, J=7.8 Hz), 7.26 (m, 4H), 7.17 (m, 3H), 7.09 (t, 1H, J=7.2 Hz), 7.04 (d, 1H, J=7.8 Hz), 4.96 (d, 1H, J=1.8 Hz), 4.63 (br s, 3H), 4.12 (m, 1H), 3.77 (m, 1H), 3.69 (m, 1H), 3.38 (d, 1H, J=12.0 Hz), 3.06 (d, 1H, J=10.8 Hz), 2.59 (m, 1H), 2.54 (m, 1H), 1.87 (d, 1H, J=10.8 Hz), 1.70 (d, 1H, J=10.8 Hz), 1.44 (m, 1H), 1.27 (q, 1H, J=13.2 Hz). $^{13}$C NMR (150 MHz, CDCl$_3$): δ 173.2, 144.6, 141.5, 128.5 (2C), 128.2 (2C), 127.5, 126.6 (3C), 125.8 (2C), 72.8, 62.8, 59.8, 56.5, 44.9, 41.3, 36.7, 32.1.

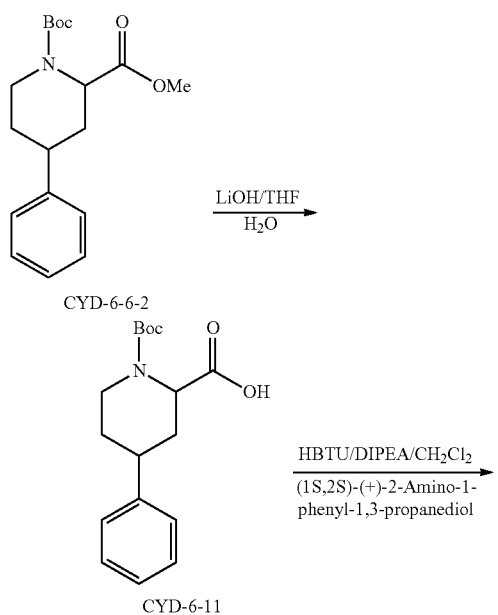

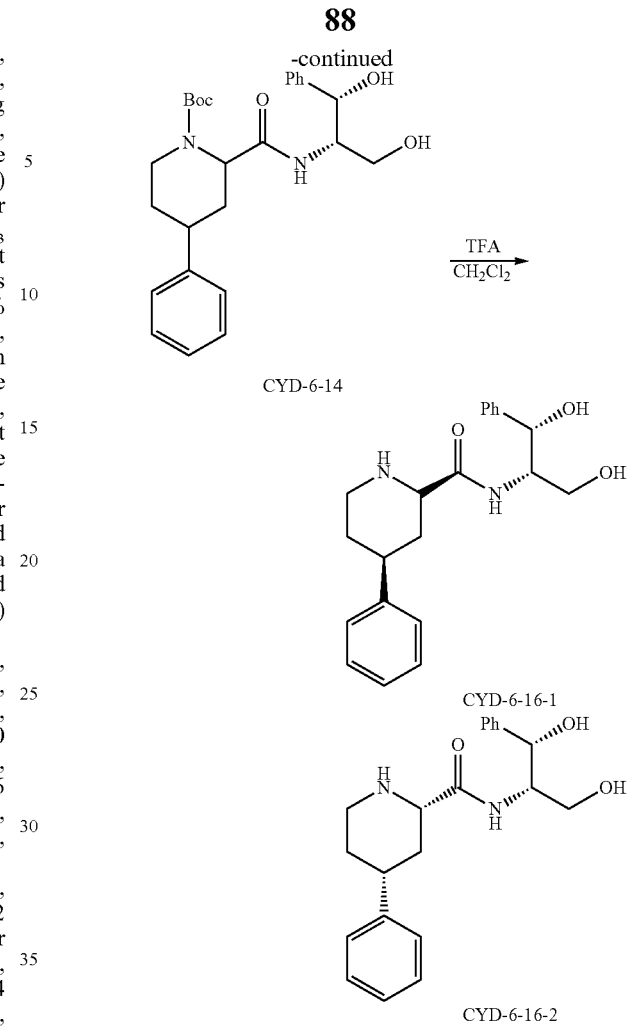

In Vitro Pharmacological Assessment of Synthesized Molecules.

The Chinese hamster ovary (CHO) cell line stably transfected with 5-HT$_{2C}$R was a generous gift of K. Berg and W. Clarke (University of Texas Health Science Center, San Antonio) (K. A. Berg, W. P. Clarke, C. Sailstad, A. Saltzman and S. Maayani, *Mol. Pharmacol.* 1994, 46 (3), 477-484; Ding et al., *ACS Chem. Neurosci.* 3, 538-545, 2012). Cells were grown at 37° C., 5% CO$_2$ and 85% relative humidity in GlutaMax α-MEM (Invitrogen, Carlsbad Calif.), 5% fetal bovine serum (Atlanta Biologicals, Atlanta Ga.), 100 μg/mL hygromycin (Mediatech, Manassas Va.) and were passaged when they reached 80% confluence.

Changes in Ca$_i^{++}$ levels were determined using the calcium sensitive dye Calcium 4 (FLIPR No-wash kit, Molecular Devices, Sunnyvale, Calif., part #R8142). Cells were plated in serum-replete medium at 20,000 cells/well in black-sided, clear bottom 96-well tissue culture plates and were fed ~24 hrs later with serum-free medium. Following overnight incubation, medium was removed and replaced with 40 μL of fresh serum-free medium plus 40 μL Calcium 4 dye solution in Hank's balanced saline solution (HBSS, without CaCl$_2$ or MgCl$_2$) supplemented with 2.5 mM water soluble probenicid (Invitrogen) to inhibit extracellular transport of the dye. Plates were incubated for 60 min at 37° C. and 60 min at room temperature in the dark. Fluorescence ($\lambda_{ex}$=485 nm, $\lambda_{em}$=525 nm) was measured with a FlexStation3 (Molecular Devices). A baseline was established for each well during the initial segment of each run. Addition of 20 μL of 5× concentrated tested compound occurred at 17 sec and fluorescence was recorded every 1.7 sec for 90 sec to determine any innate agonist activity. This first round of 90 sec recordings provided a 20 min preincubation period. Following another 17 sec baseline recording, 25 μL of 5 nM 5-HT (yielding a final concentration of 1 nM) was added and fluorescence was again measured every 1.7 sec for 90 sec. Maximum peak height was determined by the FlexStation software (SoftMax Pro 5.2) for each well and was normalized to vehicle control.

In Vivo Pharmacological Assessment of Synthesized Molecules.

Locomotor activity was monitored and quantified under low light conditions using a modified open field activity system (San Diego Instruments, San Diego, Calif.) according to previous publications with minor modifications (Cunningham et al., 2011, *Neuropharmacology* 61:513-523). Clear Plexiglass chambers (40×40×40 cm) were surrounded by a 4×4 photobeam matrix positioned 4 cm from the chamber floor. Consecutive photobeam breaks within the 16×16 cm of the activity monitor were recorded as central ambulation. Peripheral ambulation was counted as consecutive beam breaks in the surrounding perimeter. Central and peripheral ambulations were summed to provide a measure of total horizontal ambulation. Rats were acclimated to the colony room and following 1 week of handling, were habituated to the activity monitors for 30 min. The effects of CYD-1-78-2 and CYD-1-79 alone or in combination with the selective 5-HT$_{2C}$R agonist WAY163909 were established in a within-subjects design. To control for order effects, drug doses and vehicles were administered in random sequence to individual rats across sessions such that all rats received all treatment combinations and were tested every three days. Rats received vehicle (saline, 1 mL/kg, i.p.), CYD-1-78-2 (0.5, 1, or 3 mg/kg, i.p.) or the combination of CYD-1-78-2 (0.5 mg/kg, i.p.) plus WAY163909 (1 mg/kg, i.p.) immediately prior to placement in activity monitors on each test day; locomotor activity was assessed for 90 min. In a separate cohort of rats, rats received vehicle (saline, 1 mL/kg, i.p.), CYD-1-79 (0.5, 1, or 5 mg/kg, i.p.) or the combination of CYD-1-79 (0.5 mg/kg, i.p.) plus WAY163909 (1 mg/kg, i.p.) immediately prior to placement in activity monitors on each test day; locomotor activity was assessed for 90 min. The combination of CYD-1-78-2 plus WAY163909 or CYD-1-79 plus WAY163909 was administered simultaneously.

Locomotor activity data are presented as mean total horizontal ambulation (±SEM) over the entire 90-min session or within 5 min time bins across the session. A two-way ANOVA for repeated measures for the factors of treatment and time was conducted. The main effect of treatment on total horizontal ambulation was analyzed with a repeated measures, one-way analysis of variance using the GLM procedure (SAS for Windows). Subsequent a priori comparisons between means for total horizontal ambulation were made using the Dunnett's procedure, with vehicle (saline) as the comparator.

The invention claimed is:

1. A compound having the general formula of Formula I

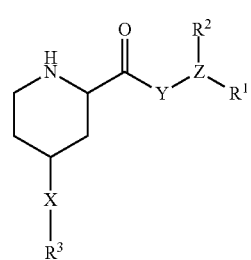

Formula I wherein, Y is —NH;
Z is a linear or branched $C_1$, $C_2$, $C_3$, or $C_4$, alkyl;
$R^1$ is hydroxy, or hydroxy substituted $C_{1-4}$alkyl;
$R^2$ is hydrogen, hydroxy, or hydroxy substituted $C_{1-4}$alkyl;
X is a linear, saturated $C_{10-15}$alkyl; and
$R^3$ is hydrogen, methyl, or ethyl.

2. The compound of claim 1, wherein $R^1$ is a hydroxy substituted $C_1$ alkyl.

3. The compound of claim 1, wherein $R^2$ is hydroxy.

4. The compound of claim 1, wherein the compound is

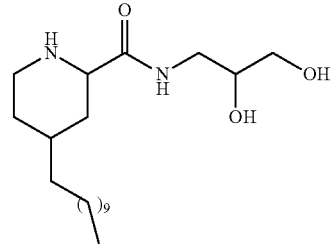

(2,4-cis-4-undecyl-piperidine-2-carboxylic acid (2,3-dihydroxypropyl)amide); or

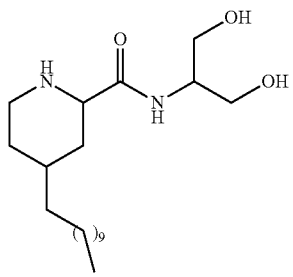

(2,4-cis-4-undecyl-piperidine-2-carboxylic acid (2-hydroxy-1-hydroxymethyl-ethyl)amide).

* * * * *